US008741938B2

(12) United States Patent  
Kempf et al.

(10) Patent No.: US 8,741,938 B2  
(45) Date of Patent: Jun. 3, 2014

(54) COMPOUNDS THAT ARE USEFUL FOR IMPROVING PHARMACOKINETICS

(71) Applicant: AbbVie Inc., North Chicago, IL (US)

(72) Inventors: Dale J. Kempf, Libertyville, IL (US); Charles A. Flentge, Salem, WI (US); John T. Randolph, Libertyville, IL (US); Peggy Huang, Lake Bluff, IL (US); Larry L. Klein, Lake Forest, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/954,100

(22) Filed: Jul. 30, 2013

(65) Prior Publication Data

US 2013/0317071 A1 Nov. 28, 2013

Related U.S. Application Data

(60) Continuation of application No. 13/362,833, filed on Jan. 31, 2012, now Pat. No. 8,524,753, which is a division of application No. 12/834,315, filed on Jul. 12, 2010, now Pat. No. 8,133,892, which is a division of application No. 11/366,172, filed on Mar. 2, 2006, now Pat. No. 7,786,153.

(60) Provisional application No. 60/658,002, filed on Mar. 2, 2005.

(51) Int. Cl.  
*A61K 31/426* (2006.01)  
*C07D 277/30* (2006.01)

(52) U.S. Cl.  
CPC .......... *C07D 277/30* (2013.01); *A61K 31/426* (2013.01)  
USPC .......................................... 514/365; 548/204

(58) Field of Classification Search  
CPC ........................... C07D 277/30; A61K 31/426  
USPC .......................................... 514/365; 548/204  
See application file for complete search history.

(56) References Cited

U.S. PATENT DOCUMENTS

| 5,142,056 | A | 8/1992 | Kempe et al. |
| 6,017,928 | A | 1/2000 | Kempf et al. |
| 6,703,403 | B2 | 3/2004 | Norbeck et al. |
| 2004/0039029 | A1 | 2/2004 | Askew et al. |
| 2006/0199851 | A1 | 9/2006 | Kempf et al. |
| 2008/0161246 | A1 | 7/2008 | Klein et al. |

FOREIGN PATENT DOCUMENTS

| CN | 1554647 | A | 12/2004 |
| EP | 486948 | A2 | 5/1992 |
| JP | 8041006 | A | 2/1996 |
| WO | 9414436 | A1 | 7/1994 |
| WO | 9507696 | A1 | 3/1995 |
| WO | 9929311 | A1 | 6/1999 |
| WO | 2005058841 | A2 | 6/2005 |
| WO | 2005058841 | A3 | 6/2005 |
| WO | 2005061487 | A1 | 7/2005 |
| WO | 2006055754 | A1 | 5/2006 |
| WO | 2007103670 | A2 | 9/2007 |
| WO | 2007103670 | A3 | 9/2007 |
| WO | 2008010921 | A2 | 1/2008 |
| WO | 2008027932 | A2 | 3/2008 |
| WO | 2008027932 | A3 | 3/2008 |

OTHER PUBLICATIONS

Jubert et al. "Equilibrium and structural studies of complexes with a hexadentate ligand containing amide, amine and pyridyl nitrogen donors. Crystal structures of copper(II), nickel(II) and cobalt(III) complexes" Journal of the Chemical Society, Dalton Transactions (2002), (13), 2660-2669.*  
Bai J.P., et al., "Use of Classification Regression Tree in Predicting Oral Absorption in Humans," Journal of Chemical Information and Computer Sciences, 2004, vol. 44 (6), pp. 2061-2069.  
Berge, S. M. et al., "Pharmaceutical Salts," Journal of Pharmaceutical Sciences, 1977, vol. 66 (1), pp. 1-19.  
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.  
Flentge C.A. et al., "Synthesis and Evaluation of Bifunctional Inhibitors of Cytochrome P-450 3A," poster presented at the 236TH ACS National Meeting (Philadelphia, PA), 2008.  
Flentge C.A., et al., "Synthesis and Evaluation of Inhibitors of Cytochrome P450 3A (CYP3A) for Pharmacokinetic Enhancement of Drugs," Bioorganic & Medicinal Chemistry Letters, 2009, vol. 19 (18), pp. 5444-5448.  
Gamage S.A., et al., "Dicationic Bis(9-Methylphenazine-1-Carboxamides): Relationships Between Biological Activity and Linker Chain Structure for a Series of Potent Topoisomerase Targeted Anticancer Drugs," Journal of Medicinal Chemistry, 2001, vol. 44 (9), pp. 1407-1415.  
Greene T.W., et al., in: Protective Groups in Organic Synthesis, 3rd Edition, John Wiley and Sons, Inc., 1999, Preface, Table of Contents, Abbreviations.

(Continued)

Primary Examiner — Joseph Kosack  
(74) Attorney, Agent, or Firm — Bradley E. Davis

(57) ABSTRACT

Novel compounds of formula 1

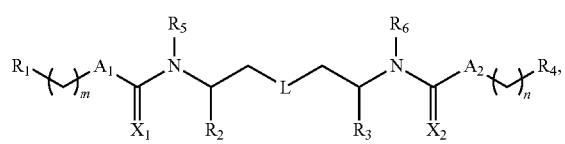

or a pharmaceutically acceptable salt thereof inhibit cytochrome P450 monooxygenase.

20 Claims, No Drawings

(56) References Cited

OTHER PUBLICATIONS

Greene T.W., et al., "Protective Groups in Organic Synthesis" 2nd Edition, John Wiley and Sons., Inc., 1991, Table of Contents.

Hamada Y., et al., "New Water-soluble Prodrugs of HIV Protease Inhibitors Based on O->N Intramolecular acyl Migration," Bioorganic & Medicinal Chemistry, 2002, vol. 10 (12), pp. 4155-4167.

Jacques et al., "Enantiomers, Racemates, and Resolutions," J. Wiley & Sons, Chapter 3, pp. 197-213, 1981.

Kawanishi M., et al., "Structure-Activity Relationship of Anti-Malarial Spongean Peroxides Having a 3-Methoxy-1,2-Dioxane Structure," Bioorganic and Medicinal Chemistry, 2004, vol. 12 (20), pp. 5297-5307.

Kempf D.J., et al., "Discovery of Ritonavir, a Potent Inhibitor of HIV Protease with High Oral Bioavailability and Clinical Efficacy," Journal of Medicinal Chemistry, 1998, vol. 41 (4), pp. 602-617.

Kempf D.J., et al., "Pharmacokinetic Enhancement of Inhibitors of the Human Immunodeficiency Virus Protease by Coadministration With Ritonavir," Antimicrobial Agents and Chemotherapy, 1997, vol. 41 (3), pp. 654-660.

Kempf D.J., et al., "Structure-Based, C2 Symmetric Inhibitors of HIV Protease," Journal of Medicinal Chemistry, 1990, vol. 33 (10), pp. 2687-2689.

Kumar G.N., et al., "Cytochrome P450-Mediated Metabolism of the HIV-1 Protease Inhibitor Ritonavir (Abt-538) in Human Liver Microsomes," Journal of Pharmacology and Experimental Therapeutics, 1996, vol. 277 (1), pp. 423-431.

Prescott D.M., "Methods in Cell Biology", Academic Press, 1976, Table of Contents.

Yun C.H., et al., "Oxidation of the Antihistaminic Drug Terfenadine in Human Liver Microsomes," Drug Metabolism and Disposition, 1993, vol. 21 (3), pp. 403-409.

Zinic, et al., "N-Benzyloxycarbonylaziridine in the Syntheses of 2-Aminoethyl Armed Lariats and Selectively N-Protected Polyazacrown Ether," Journal of the Chemical Society Perkin Transactions, 1993, pp. 21-26.

* cited by examiner

COMPOUNDS THAT ARE USEFUL FOR IMPROVING PHARMACOKINETICS

This application is a continuation of U.S. application Ser. No. 13/362,833 filed Jan. 31, 2012 which is a divisional of U.S. patent application Ser. No. 12/834,315, filed Jul. 12, 2010 which is a divisional of U.S. patent application Ser. No. 11/366,172, filed Mar. 2, 2006, which claims priority from U.S. Patent Application Ser. No. 60/658,002, filed Mar. 2, 2005.

TECHNICAL FIELD

The present invention relates to novel compounds of formula I, pharmaceutical compositions containing compounds of formula I and a method for improving the pharmacokinetics of drugs which are metabolized by cytochrome P450 monooxygenase.

BACKGROUND OF THE INVENTION

Some drugs are metabolized by cytochrome P450 monooxygenase, leading to unfavorable pharmacokinetics and the need for more frequent and higher doses than are most desirable. Administration of such drugs with an agent that inhibits metabolism by cytochrome P450 monooxygenase will improve the pharmacokinetics (i.e., increase half-life, increase the time to peak plasma concentration, increase blood levels) of the drug.

It has been discovered that coadministration of compounds of formula I with a drug which is metabolized by cytochrome P450 monooxygenase, especially the P450 3A4 isozyme, causes an improvement in the pharmacokinetics of such a drug.

DISCLOSURE OF THE INVENTION

In accordance with the present invention, there is disclosed novel compounds of formula I that inhibit cytochrome P450 monooxygenase, especially the P450 3A4 isozyme, a method of improving the pharmacokinetics of a drug (or a pharmaceutically acceptable salt thereof) which is metabolized by cytochrome P450 monooxygenase in mammals, and pharmaceutical compositions including compounds of formula I. More particularly, the present invention is directed to compounds of formula I

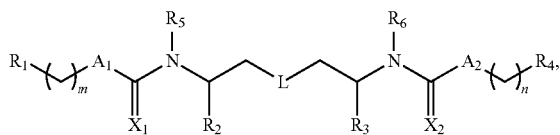

or a pharmaceutically acceptable salt, prodrug, salt of a prodrug, or a combination thereof, wherein $R_1$ is selected from the group consisting of aryl, heteroaryl and heterocycle;

$R_2$ and $R_3$ are each independently selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_CR_D)$alkyl;

$R_4$ is selected from the group consisting of aryl, heteroaryl, and heterocycle;

$R_5$ and $R_6$ are each independently selected from the group consisting of hydrogen, lower alkyl and arylalkyl;

m is 0-3;

n is 0-3;

$A_1$ is absent or selected from the group consisting of O and $NR_{A1}$ wherein $R_{A1}$ is selected from the group consisting of hydrogen and lower alkyl;

$A_2$ is absent or selected from the group consisting of O and $NR_{A2}$ wherein $R_{A2}$ is selected from the group consisting of hydrogen and lower alkyl;

$X_1$ and $X_2$ are each independently selected from the group consisting of O and S;

L is selected from the group consisting of

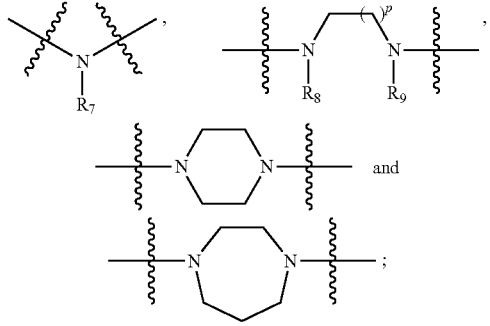

p is 1-5;

$R_7$, $R_8$ and $R_9$ are each independently selected from the group consisting of hydrogen, alkenyl, alkenylcarbonyl, alkoxyalkyl, alkoxycarbonyl, alkoxycarbonylalkyl, alkyl, alkylcarbonyl, alkylcarbonylalkyl, alkylcarbonyloxyalkyl, alkynyl, alkynylcarbonyl, arylalkoxycarbonyl, arylalkyl, arylalkylcarbonyl, arylcarbonyl, aryloxyalkyl, arylthioalkoxyalkyl, arylthioalkyl, carboxyalkyl, cyanoalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocyclethioalkoxyalkyl, heterocyclethioalkyl, hydroxyalkyl, $(NR_CR_D)$alkyl and

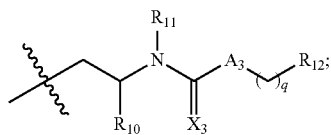

$R_{10}$ is selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_AR_B)$alkyl;

$R_{11}$ is selected from the group consisting of hydrogen, lower alkyl and arylalkyl;

$R_{12}$ is selected from the group consisting of aryl, heteroaryl and heterocycle;

q is 0-3;

$X_3$ is selected from the group consisting of O and S; and $A_3$ is absent or selected from the group consisting of O and $NR_{A3}$ wherein $R_{A3}$ is selected from the group consisting of hydrogen and lower alkyl;

$R_C$ and $R_D$ are each independently selected from the group consisting of hydrogen, alkoxycarbonyl, alkyl, alkylcarbonyl, alkylsulfonyl, arylalkoxycarbonyl, arylsulfonyl, formyl, $(NR_ER_F)$carbonyl and $(NR_ER_F)$sulfonyl;

$R_E$ and $R_F$ are each independently selected from the group consisting of hydrogen and lower alkyl; and wherein any one of said aryl, heteroaryl, heterocycle, cycloalkyl, cycloalkyl moiety of said cycloalkylalkyl, aryl moieties of said arylalkoxyalkyl, arylalkoxycarbonyl, arylalkyl, arylalkylcarbonyl, arylcarbonyl, aryloxyalkyl, aryloxycarbonyl, arylthioalkoxyalkyl and arylthioalkyl, heteroaryl moieties of said heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl and heteroarylthioalkyl, and heterocycle moieties of said heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, and heterocyclethioalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, $(NR_AR_B)$alkoxy and $(NR_AR_B)$alkyl; and $R_A$ and $R_B$ are independently selected from the group consisting of hydrogen and lower alkyl.

In another embodiment, the present invention discloses compounds of formula I, or a pharmaceutically acceptable salt, prodrug, salt of a prodrug, or a combination, wherein $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_7$, $R_8$ and $R_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, $(NR_CR_D)$alkyl and

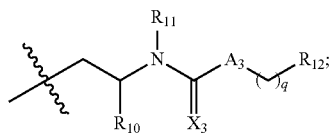

$R_{10}$ is selected from the group consisting of hydrogen, alkoxycarbonylalkyl, alkyl, arylalkoxyalkyl, arylalkyl and cycloalkylalkyl; $R_C$ and $R_D$ are each independently selected from the group consisting of hydrogen, alkyl and alkoxycarbonyl;

wherein any one of said cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, $(NR_AR_B)$alkoxy and $(NR_AR_B)$alkyl; and $R_1$, $R_4$, $R_5$, $R_6$, $R_{11}$, $R_{12}$, $R_A$, $R_B$, $A_1$, $A_2$, $A_3$, $X_1$, $X_2$, $X_3$, m, n, p and q are as defined in formula I.

In another embodiment, the present invention discloses compounds of formula I, or a pharmaceutically acceptable salt, prodrug, salt of a prodrug, or a combination, wherein $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; L is selected from the group consisting of

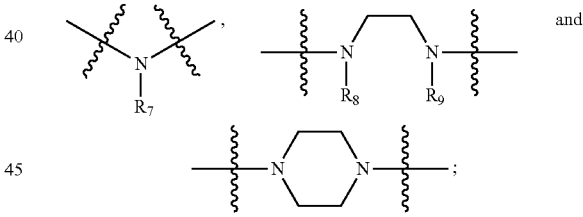

$R_7$, $R_8$ and $R_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, $(NR_CR_D)$alkyl and

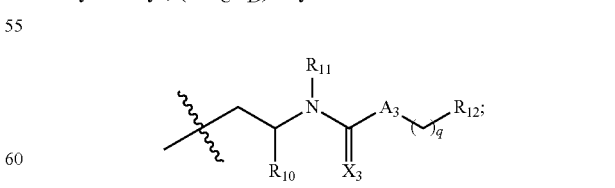

$R_{10}$ is selected from the group consisting of hydrogen, alkoxycarbonylalkyl, alkyl, arylalkoxyalkyl, arylalkyl and cycloalkylalkyl; $R_C$ and $R_D$ are each independently selected from the group consisting of hydrogen, alkyl and alkoxycarbonyl;

wherein any one of said cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_1$, $R_4$, $R_5$, $R_6$, $R_{11}$, $R_{12}$, $R_A$, $R_B$, $A_1$, $A_2$, $A_3$, $X_1$, $X_2$, $X_3$, m, n and q are as defined in formula I.

In another embodiment, the present invention discloses compounds of formula I, or a pharmaceutically acceptable salt, prodrug, salt of a prodrug, or a combination, wherein $R_1$ is heteroaryl; $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_4$ is heteroaryl;

$R_7$, $R_8$ and $R_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, ($NR_CR_D$)alkyl and

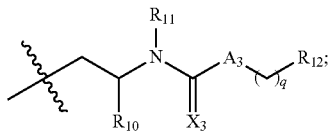

$R_{10}$ is selected from the group consisting of hydrogen, alkoxycarbonylalkyl, alkyl, arylalkoxyalkyl, arylalkyl and cycloalkylalkyl; $R_{12}$ is heteroaryl; $R_C$ and $R_D$ are each independently selected from the group consisting of hydrogen, alkyl and alkoxycarbonyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; $R_5$, $R_6$, $R_{11}$, $R_A$, $R_B$, $A_1$, $A_2$, $A_3$, $X_1$, $X_2$, $X_3$, m, n, p and q are as defined in formula I.

In another embodiment, the present invention discloses compounds of formula I, or a pharmaceutically acceptable salt, prodrug, salt of a prodrug, or a combination, wherein $R_1$ is heteroaryl; $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_4$ is heteroaryl;

L is selected from the group consisting of

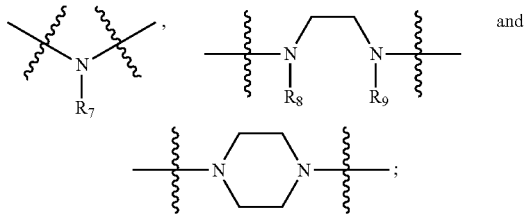

$R_7$, $R_8$ and $R_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, ($NR_CR_D$)alkyl and

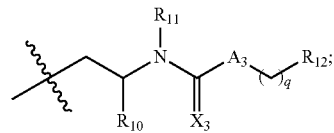

$R_{10}$ is selected from the group consisting of hydrogen, alkoxycarbonylalkyl, alkyl, arylalkoxyalkyl, arylalkyl and cycloalkylalkyl; $R_{12}$ is heteroaryl; $R_C$ and $R_D$ are each independently selected from the group consisting of hydrogen, alkyl and alkoxycarbonyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; $R_5$, $R_6$, $R_{11}$, $R_A$, $R_B$, $A_1$, $A_2$, $A_3$, $X_1$, $X_2$, $X_3$, m, n and q are as defined in formula I.

In another embodiment, the present invention discloses compounds of formula I, or a pharmaceutically acceptable salt, prodrug, salt of a prodrug, or a combination, wherein $R_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl;

$R_7$ is selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, (NR$_C$R$_D$)alkyl and

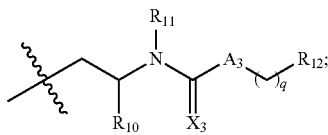

R$_C$ and R$_D$ are independently selected from the group consisting of hydrogen, alkyl and alkoxycarbonyl, R$_8$ and R$_9$ are each independently selected from the group consisting of hydrogen, alkyl, heteroarylalkoxycarbonyl and heterocyclealkoxycarbonyl; R$_{10}$ is selected from the group consisting of hydrogen and arylalkyl; R$_{12}$ is heteroaryl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_5$, R$_6$, R$_{11}$, R$_A$, R$_B$, A$_1$, A$_2$, A$_3$, X$_1$, X$_2$, X$_3$, m, n, p and q are as defined in formula I.

In another embodiment, the present invention discloses compounds of formula I, or a pharmaceutically acceptable salt, prodrug, salt of a prodrug, or a combination, wherein R$_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; R$_2$ and R$_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; R$_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl;

L is selected from the group consisting of

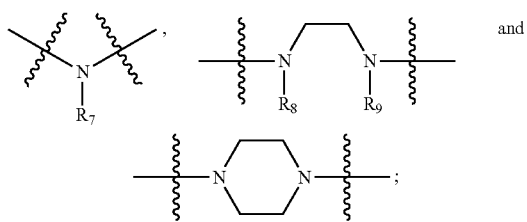

R$_7$ is selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, (NR$_C$R$_D$)alkyl and

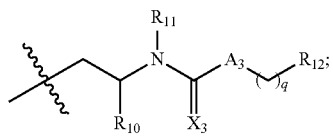

R$_8$ and R$_9$ are each independently selected from the group consisting of hydrogen, alkyl, heteroarylalkoxycarbonyl and heterocyclealkoxycarbonyl; R$_{10}$ is selected from the group consisting of hydrogen and arylalkyl; R$_{12}$ is heteroaryl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_5$, R$_6$, R$_{11}$, R$_A$, R$_B$, R$_C$, R$_D$, A$_1$, A$_2$, A$_3$, X$_1$, X$_2$, X$_3$, m, n and q are as defined in formula I.

In another embodiment, the present invention discloses compounds of formula I, or a pharmaceutically acceptable salt, prodrug, salt of a prodrug, or a combination, wherein R$_1$ is heteraryl wherein said heteroaryl is selected from the group consisting of imidazolyl, oxazolyl, pyrazolyl, pyridinyl, thiazolyl, and thienyl; R$_2$ and R$_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; R$_4$ is heteroaryl wherein said heteroaryl is selected from the group consisting of imidazolyl, oxazolyl, pyrazolyl, pyridinyl, thiazolyl, and thienyl; R$_7$ is selected from the group consisting of hydrogen, alkenyl, alkoxycarbonylalkyl, alkyl, alkylcarbonyl, arylalkyl wherein the aryl portion of arylalkyl is selected from the group consisting of phenyl and naphthyl, arylcarbonyl wherein the aryl portion of arylcarbonyl is phenyl or naphthyl, carboxyalkyl, cycloalkylalkyl, di(alkoxycarbonyl)alkyl, heteroarylalkoxycarbonyl wherein the heteroaryl portion of heteroarylalkoxycarbonyl is thiazolyl, heteroarylalkyl wherein the heteroaryl portion of heteroarylalkyl is selected from the group consisting of imidazolyl, pyridinyl, pyrrolyl, and quinolinyl, heterocyclealkyl wherein the heterocycle portion of heterocyclealkyl is tetrahydrofuranyl, (NR$_C$R$_D$)alkyl and

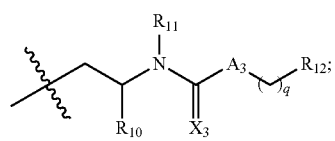

R$_C$ and R$_D$ are independently selected from the group consisting of hydrogen, alkyl and alkoxycarbonyl; R$_8$ and R$_9$ are independently selected from the group consisting of hydrogen, alkyl and heteroarylalkoxycarbonyl wherein the heteroaryl portion of heteroarylalkoxycarbonyl is selected from the group consisting of imidazolyl, oxazolyl, pyrazolyl, pyridinyl, thiazolyl, and thienyl; R$_{10}$ is selected from the group consisting of hydrogen and arylalkyl wherein the arylalkyl is phenylmethyl; R$_{12}$ is heteroaryl wherein said heteroaryl is selected from the group consisting of imidazolyl, oxazolyl, pyrazolyl, pyridinyl, thiazolyl, and thienyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_5$, R$_6$, R$_{11}$, R$_A$, R$_B$, A$_1$, A$_2$, A$_3$, X$_1$, X$_2$, X$_3$, m, n, p and q are as defined in formula I.

In another embodiment, the present invention discloses compounds of formula I, or a pharmaceutically acceptable salt, prodrug, salt of a prodrug, or combination thereof, wherein R$_1$ is heteraryl wherein said heteroaryl is selected from the group consisting of imidazolyl, oxazolyl, pyrazolyl, pyridinyl, thiazolyl, and thienyl; R$_2$ and R$_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; R$_4$ is heteroaryl wherein said heteroaryl is selected from the group consisting of imidazolyl, oxazolyl, pyrazolyl, pyridinyl, thiazolyl, and thienyl; L is selected from the group consisting of

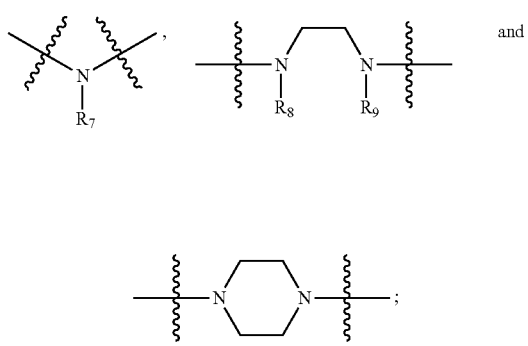

R$_7$ is selected from the group consisting of hydrogen, alkenyl, alkoxycarbonylalkyl, alkyl, alkylcarbonyl, arylalkyl wherein the aryl portion of arylalkyl is selected from the group consisting of phenyl and naphthyl, arylcarbonyl wherein the aryl portion of arylcarbonyl is phenyl or naphthyl, carboxyalkyl, cycloalkylalkyl, di(alkoxycarbonyl)alkyl, heteroarylalkoxycarbonyl wherein the heteroaryl portion of heteroarylalkoxycarbonyl is thiazolyl, heteroarylalkyl wherein the heteroaryl portion of heteroarylalkyl is selected from the group consisting of imidazolyl, pyridinyl, pyrrolyl, and quinolinyl, heterocyclealkyl wherein the heterocycle portion of heterocyclealkyl is tetrahydrofuranyl, (NR$_C$R$_D$)alkyl and

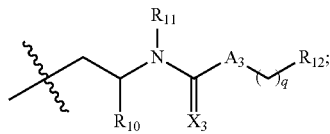

R$_C$ and R$_D$ are independently selected from the group consisting of hydrogen, alkyl and alkoxycarbonyl; R$_8$ and R$_9$ are independently selected from the group consisting of hydrogen, alkyl and heteroarylalkoxycarbonyl wherein the heteroaryl portion of heteroarylalkoxycarbonyl is selected from the group consisting of imidazolyl, oxazolyl, pyrazolyl, pyridinyl, thiazolyl, and thienyl; R$_{10}$ is selected from the group consisting of hydrogen and arylalkyl wherein the arylalkyl is phenylmethyl; R$_{12}$ is heteroaryl wherein said heteroaryl is selected from the group consisting of imidazolyl, oxazolyl, pyrazolyl, pyridinyl, thiazolyl, and thienyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_5$, R$_6$, R$_{11}$, R$_A$, R$_B$, A$_1$, A$_2$, A$_3$, X$_1$, X$_2$, X$_3$, m, n and q are as defined in formula I.

In another embodiment, the present invention discloses compounds of formula II

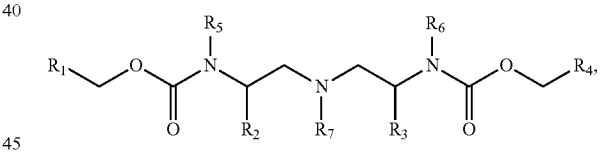

II or a pharmaceutically acceptable salt, prodrug, salt of a prodrug, or a combination thereof, wherein R$_1$, R$_2$, R$_3$, R$_4$, R$_5$, R$_6$ and R$_7$ are as defined in formula I.

In another embodiment, the present invention discloses compounds of formula II, or a pharmaceutically acceptable salt, prodrug, salt of a prodrug, or a combination thereof, wherein R$_1$ is heteroaryl or heterocycle and R$_4$ is heteroaryl or heterocycle, wherein any one of said heteroaryl and heterocycle, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_2$, R$_3$, R$_5$, R$_6$, R$_A$, R$_B$ and R$_7$ are as defined in formula I.

In another embodiment, the present invention discloses compounds of formula II, or a pharmaceutically acceptable salt, prodrug, salt of a prodrug, or a combination thereof, wherein $R_1$ is heteroaryl or heterocycle, $R_4$ is heteroaryl or heterocycle, $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; wherein any of said heteroaryl, heterocycle, cycloalkyl moiety or cycloalkylalkyl, aryl moieties of said arylalkoxyalkyl and arylalkyl, heteroaryl moiety of heteroarylalkyl and heterocycle moiety of heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_A R_B$, ($NR_A R_B$)alkoxy and ($NR_A R_B$)alkyl; and $R_A$, $R_B$, $R_5$, $R_6$ and $R_7$ are as defined in formula I.

In another embodiment, the present invention discloses compounds of formula II, or a pharmaceutically acceptable salt, prodrug, salt of a prodrug, or combination thereof, wherein $R_1$ is heteroaryl or heterocycle, $R_4$ is heteroaryl or heterocycle, $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_7$ is selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl heterocyclealkyl, (NR$_C$R$_D$)alkyl and

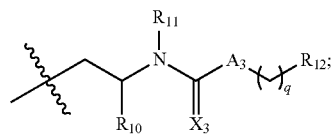

wherein any of said heteroaryl, heterocycle, cycloalkyl moiety or cycloalkylalkyl, aryl moieties of said arylalkoxyalkyl, arylalkyl and arylcarbonyl, heteroaryl moieties of heteroarylalkoxycarbonyl and heteroarylalkyl and heterocycle moieties of heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_A R_B$, ($NR_A R_B$)alkoxy and ($NR_A R_B$)alkyl; and $R_A$, $R_B$, $R_C$, $R_D$, $R_5$, $R_6$, $R_{11}$, $R_{12}$, $A_3$, $X_3$ and q are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; $R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; $R_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; $R_7$ is selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl heterocyclealkyl, (NR$_C$R$_D$)alkyl and

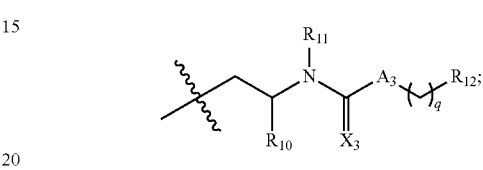

$R_C$ and $R_D$ are independently selected from the group consisting of hydrogen, alkyl and alkoxycarbonyl;

$R_{10}$ is selected from the group consisting of hydrogen and arylalkyl; and $R_{12}$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_A R_B$, ($NR_A R_B$)alkoxy and ($NR_A R_B$)alkyl; and $R_5$, $R_6$, $R_{11}$, $R_A$, $R_B$, $A_3$, $X_3$ and q are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is selected from the group consisting of imidazolyl, oxazolyl, pyrazolyl, pyridinyl, thiazolyl, and thienyl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is selected from the group consisting of imidazolyl, oxazolyl, pyrazolyl, pyridinyl, thiazolyl, and thienyl; $R_5$ and $R_6$ are each independently selected from the group consisting of hydrogen, lower alkyl and arylalkyl wherein said arylalkyl is phenylmethyl; $R_7$ is selected from the group consisting of hydrogen, alkenyl, alkoxycarbonylalkyl, alkyl, alkylcarbonyl, arylalkyl wherein the aryl portion of arylalkyl is selected from the group consisting of phenyl and naphthyl, arylcarbonyl wherein the aryl portion of arylcarbonyl is selected from the group consisting of phenyl and naphthyl, carboxyalkyl, cycloalkylalkyl wherein the cycloalkyl portion of cycloalkylalkyl is selected from the group consisting of cyclopropyl, cyclobutyl, cyclopentyl and cyclohexyl, di(alkoxycarbonyl)alkyl, heteroarylalkoxycarbonyl wherein the heteroaryl portion of heteroarylalkoxycarbonyl is thiazolyl, heteroarylalkyl wherein the heteroaryl portion of heteroarylalkyl is selected from the group consisting of imidazolyl, pyridinyl, pyrrolyl and quinolinyl, heterocyclealkyl wherein the heterocycle portion of the heterocyclealkyl is tetrahydrofuranyl, $(NR_CR_D)$alkyl and

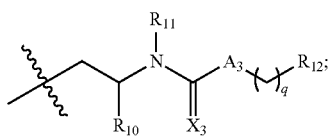

$R_C$ and $R_D$ are independently selected from the group consisting of hydrogen, alkyl, alkoxycarbonyl;

$R_{10}$ is selected from the group consisting of hydrogen and arylalkyl; wherein said arylalkyl is phenylmethyl;

$R_{12}$ is heteroaryl wherein said heteroaryl is selected from the group consisting of imidazolyl, oxazolyl, pyrazolyl, pyridinyl, thiazolyl, and thienyl; wherein any one of said heteroaryl, cycloalkyl moiety of said cycloalkylalkyl, aryl moieties of said arylalkoxyalkyl, arylalkyl, and arylcarbonyl, heteroaryl moieties of said heteroarylalkoxycarbonyl and heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, $(NR_AR_B)$alkoxy and $(NR_AR_B)$alkyl; and $R_{11}$, $R_A$, $R_B$, $A_3$, $X_3$ and q are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is selected from the group consisting of imidazolyl, oxazolyl, pyrazolyl, pyridinyl, thiazolyl, and thienyl; $R_2$ and $R_3$ are independently selected from the group consisting of hydrogen, 2-methoxy-2-oxoethyl, methyl, 2-methylpropyl, phenylmethoxymethyl, phenylmethyl and cyclohexylmethyl; $R_4$ is heteroaryl wherein said heteroaryl is selected from the group consisting of imidazolyl, oxazolyl, pyrazolyl, pyridinyl, thiazolyl, and thienyl; $R_5$ and $R_6$ are hydrogen; $R_7$ is selected from the group consisting of hydrogen, 4-pentenyl, 2,2-dimethyl-4-pentenyl, 6-methoxy-6-oxohexyl, methyl, ethyl, propyl, isopropyl, butyl, 2-methylpropyl, 2,2-dimethylpropyl, 3-methylbutyl, 2-ethylbutyl, pentyl, hexyl, 3-methylhexyl, 3,5,5-trimethylhexyl, 2,2-dimethylpentyl, 2,3-dimethylpentyl, heptyl, octyl, acetyl, phenylmethyl, phenylethyl, naphthylmethyl, benzoyl, 3-carboxypropyl, cyclopropylmethyl, cyclohexylmethyl, 4-ethoxy-2-(ethoxycarbonyl)-4-oxobutyl, 2-(1,3-thiazol-5-ylmethoxy)carbonyl, 1H-imidazolylmethyl, pyridinylmethyl, pyrrolylmethyl and quinolinylmethyl, tetrahydrofuranylmethyl, $(NR_CR_D)$ethyl and

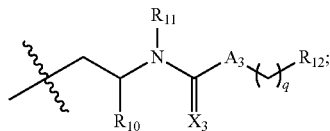

$X_3$ is O, $A_3$ is O, q is 1; $R_{11}$ is hydrogen; $R_C$ and $R_D$ are independently selected from the group consisting of hydrogen, tert-butoxycarbonyl; $R_{10}$ is selected from the group consisting of hydrogen and phenylmethyl; $R_{12}$ is heteroaryl wherein said heteroaryl is selected from the group consisting of imidazolyl, oxazolyl, pyrazolyl, pyridinyl, thiazolyl, and thienyl; wherein any one of said heteroaryl, phenyl moieties of said phenylmethoxymethyl, phenylmethyl, phenylethyl, and benzoyl, naphthyl moiety of naphthylmethyl, thiazolyl moiety of 2-(1,3-thiazol-5-ylmethoxy)carbonyl, imidazolyl moiety of 1H-imidazolylmethyl, pyridinyl moiety of pyridinylmethyl, pyrrolyl moiety of pyrrolylmethyl, quinolinyl moiety of quinolinylmethyl, and tetrahydrofuranyl moiety of tetrahydrofuranylmethyl, is independently unsubstituted or substituted with 1, 2, 3, or 4 substituents independently selected from the group consisting of methoxy, methyl, ethyl, propyl, isopropyl, butyl, tert-butyl, benzyloxy, hydroxy, methylenedioxy, phenoxy, —$NR_AR_B$, $(NR_AR_B)(C_{1-3}$ alky) and $(NR_AR_B)(C_{1-3}$ alkyl); and $R_A$ and $R_B$ are independently selected from the group consisting of hydrogen and methyl.

In another embodiment, the present invention discloses compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl, arylalkyl, heteroarylalkyl, heterocycleakyl and cycloalkylalkyl; $R_4$ is heteroaryl wherein said heteroaryl is thiazol-5-yl; $R_7$ is selected from the group consisting of hydrogen, alkenyl, alkoxycarbonylalkyl, alkyl, alkylcarbonyl, carboxyalkyl, cycloalkylalkyl, di(alkoxycarbonyl)alkyl and $(NR_CR_D)$alkyl; and wherein any one of said heteroaryl, cycloalkyl moiety of said cycloalkylalkyl, aryl moieties of said arylalkoxyalkyl and arylalkyl, heteroaryl moiety of said heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, $(NR_AR_B)$alkoxy and $(NR_AR_B)$alkyl; and $R_5$, $R_6$, $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thiazol-5-yl; $R_5$ is hydrogen; $R_6$ is hydrogen; $R_7$ is selected from the group consisting of hydrogen, alkenyl, alkoxycarbonylalkyl, alkyl, alkylcarbonyl, carboxyalkyl, cycloalkylalkyl, di(alkoxycarbonyl)alkyl and $(NR_CR_D)$alkyl; and $R_C$ and $R_D$ are independently selected from the group consisting of hydrogen and alkoxycarbonyl; wherein any one of said heteroaryl, cycloalkyl moiety of said cycloalkylalkyl and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, $—NR_AR_B$, $(NR_AR_B)$alkoxy and $(NR_AR_B)$alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thiazol-5-yl; $R_5$ is hydrogen; $R_6$ is hydrogen; and $R_7$ is selected from the group consisting of arylalkyl wherein the aryl portion of arylalkyl is selected from the group consisting of phenyl and naphthyl, and arylcarbonyl wherein the aryl portion of arylcarbonyl is selected from the group consisting of phenyl and naphthyl; wherein any one of said heteroaryl, cycloalkyl moiety of said cycloalkylalkyl and aryl moieties of said arylalkoxyalkyl, arylalkyl and arylcarbonyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, $—NR_AR_B$, $(NR_AR_B)$alkoxy and $(NR_AR_B)$alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thiazol-5-yl; $R_5$ is hydrogen; $R_6$ is hydrogen; and $R_7$ is selected from the group consisting of heteroarylalkoxycarbonyl wherein the heteroaryl portion of heteroarylalkoxycarbonyl is thiazolyl, and heteroarylalkyl wherein the heteroaryl portion of heteroarylalkyl is selected from the group consisting of imidazolyl, pyridinyl, pyrrolyl and quinolinyl, and heterocyclealkyl wherein the heterocycle portion of heterocyclealkyl is tetrahydrofuranyl; wherein any one of said heteroaryl, cycloalkyl moiety of said cycloalkylalkyl, aryl moieties of said arylalkoxyalkyl and arylalkyl, heteroaryl moieties of said heteroarylalkoxycarbonyl and heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, $—NR_AR_B$, $(NR_AR_B)$alkoxy and $(NR_AR_B)$alkyl; and $R_A$ and $R_B$ are as defined in formula I.

In another embodiment, the present invention provides compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thiazol-5-yl; $R_5$ is hydrogen; $R_6$ is hydrogen; $R_7$ is

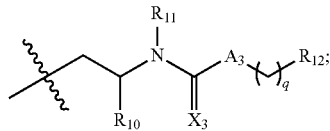

$R_{10}$ is selected from the group consisting of hydrogen, alkoxycarbonylalkyl, alkyl, arylalkoxyalkyl wherein the aryl portion of arylalkoxyalkyl is phenyl, arylalkyl wherein the aryl portion of arylalkyl is phenyl, and cycloalkylalkyl; and $R_{12}$ is heteroaryl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, $—NR_AR_B$, $(NR_AR_B)$alkoxy and $(NR_AR_B)$alkyl; and $R_{11}$, $R_A$, $R_B$, $A_3$, $X_3$, and q are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is thiazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thiazol-5-yl; $R_5$ is hydrogen; $R_6$ is hydrogen; $R_7$ is

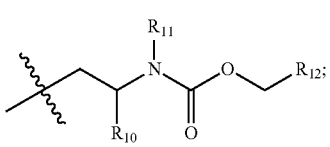

$R_{10}$ is arylalkyl wherein the arylalkyl is phenylmethyl; and $R_{12}$ heteroaryl wherein said heteroaryl is thiazol-5-yl, wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_{11}$, $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is oxazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is oxazol-5-yl; $R_5$ is hydrogen; $R_6$ is hydrogen; and $R_7$ is alkyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is thien-2-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is thien-2-yl; $R_5$ is hydrogen; $R_6$ is hydrogen; and $R_7$ is alkyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is pyridin-3-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is pyridin-3-yl; $R_5$ is hydrogen; $R_6$ is hydrogen; and $R_7$ is alkyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is imidazol-4-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is imidazol-4-yl; $R_5$ is hydrogen; $R_6$ is hydrogen; and $R_7$ is alkyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, ($NR_AR_B$)alkoxy and ($NR_AR_B$)alkyl; and $R_A$ and $R_B$ are as defined in formula I.

In another embodiment, the present invention discloses compounds of formula II, or a pharmaceutically acceptable salt, prodrug, salt of a prodrug, or combination thereof, wherein $R_1$ is heteroaryl wherein said heteroaryl is pyrazol-5-yl; $R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; $R_4$ is heteroaryl wherein said heteroaryl is pyrazol-5-yl; $R_5$ is hydrogen; $R_6$ is hydrogen; and R₇ is alkyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

In another embodiment, the present invention discloses compounds of formula III

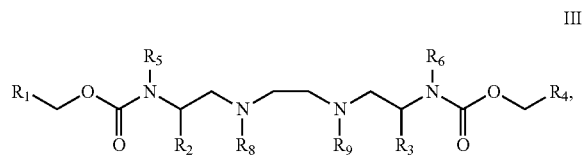

or a pharmaceutically acceptable salt, prodrug, salt of a prodrug, or a combination thereof, wherein R₁, R₂, R₃, R₄, R₅, R₆, R₈ and R₉ are as defined in formula I.

In another embodiment, the present invention discloses compounds of formula III, or a pharmaceutically acceptable salt, prodrug, salt of a prodrug, or combination thereof, wherein R₁ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; R₂ and R₃ are independently selected from the group consisting of hydrogen, alkoxycarbonylalkyl, alkyl, arylalkoxyalkyl, arylalkyl, heteroarylalkyl, heterocyclealkyl and cycloalkylalkyl; R₄ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; and R₈ and R₉ are independently selected from the group consisting of hydrogen, alkyl, heteroarylalkoxycarbonyl, and heterocyclealkoxycarbonyl; wherein any one of said heteroaryl, cycloalkyl moiety of said cycloalkylalkyl, aryl moieties of said arylalkoxyalkyl and arylalkyl, heteroaryl moieties of said heteroarylalkyl and heteroarylalkoxycarbonyl, and heterocycle moieties of said heterocyclealkoxycarbonyl and heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R₅, R₆, R$_A$ and R$_B$ are as defined in formula I.

In another embodiment, the present invention discloses compounds of formula III, or a pharmaceutically acceptable salt, prodrug, salt of a prodrug, or combination thereof, wherein R₁ is heteroaryl wherein said heteroaryl is selected from the group consisting of imidazolyl, oxazolyl, pyrazolyl, pyridinyl, thiazolyl, and thienyl; R₂ and R₃ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; R₄ is heteroaryl wherein said heteroaryl is selected from the group consisting of imidazolyl, oxazolyl, pyrazolyl, pyridinyl, thiazolyl, and thienyl; and R₅ and R₉ are independently selected from the group consisting of hydrogen, alkyl, heteroarylalkoxycarbonyl, and heterocyclealkoxycarbonyl; wherein any one of said heteroaryl, cycloalkyl moiety of said cycloalkylalkyl, aryl moieties of said arylalkoxyalkyl and arylalkyl, heteroaryl moiety of said heteroarylalkoxycarbonyl, and heterocycle moiety of said heterocyclealkoxycarbonyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R₅, R₆, R$_A$ and R$_B$ are as defined in formula I.

In another embodiment, the present invention discloses compounds of formula III, or a pharmaceutically acceptable salt, prodrug, salt of a prodrug, or combination thereof, wherein R₁ is heteroaryl wherein said heteroaryl is thiazol-5-yl; R₂ is arylalkyl wherein the aryl portion of arylalkyl is phenyl or naphthyl; R₃ is arylalkyl wherein the aryl portion of arylalkyl is phenyl or naphthyl; R₄ is heteroaryl wherein said heteroaryl is thiazol-5-yl; R₅ is hydrogen; R₆ is hydrogen; R₅ is alkyl; and R₉ is alkyl; wherein any one of said heteroaryl and aryl moiety of said arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

In another embodiment, the present invention discloses compounds of formula III, or a pharmaceutically acceptable salt, prodrug, salt of a prodrug, or combination thereof, wherein R₁ is heteroaryl wherein said heteroaryl is thiazol-5-yl; R₂ is arylalkyl wherein the aryl portion of arylalkyl is phenyl or naphthyl; R₃ is arylalkyl wherein the aryl portion of arylalkyl is phenyl or naphthyl; R₄ is heteroaryl wherein said heteroaryl is thiazol-5-yl; R₅ is hydrogen; R₆ is hydrogen; and R₈ and R₉ are independently selected from the group consisting of hydrogen and heteroarylalkoxycarbonyl wherein the heteroaryl portion of heteroarylalkoxycarbonyl is thiazol-5-yl; wherein any one of said heteroaryl, aryl moiety of arylalkyl, and heteroaryl moiety of said heteroarylalkoxycarbonyl is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

In another embodiment, the present invention discloses compounds of formula IV

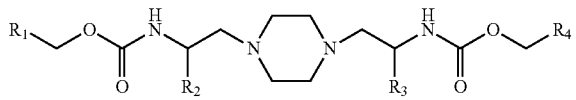

or a pharmaceutically acceptable salt, prodrug, salt of a prodrug, or a combination thereof, wherein R$_1$, R$_2$, R$_3$ and R$_4$ are as defined in formula I.

In another embodiment, the present invention discloses compounds of formula IV, or a pharmaceutically acceptable salt, prodrug, salt of a prodrug, or a combination thereof, wherein R$_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; R$_2$ and R$_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl; and R$_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; wherein any one of said heteroaryl, cycloalkyl moiety of said cycloalkylalkyl, aryl moieties of said arylalkoxyalkyl and arylalkyl, heteroaryl moiety of said heteroarylalkyl, and heterocycle moiety of said heterocyclealkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

In another embodiment, the present invention discloses compounds of formula IV, or a pharmaceutically acceptable salt, prodrug, salt of a prodrug, or a combination thereof, wherein R$_1$ is heteroaryl wherein said heteroaryl is selected from the group consisting of imidazolyl, oxazolyl, pyrazolyl, pyridinyl, thiazolyl, and thienyl; R$_2$ and R$_3$ are independently selected from the group consisting of hydrogen, alkoxycarbonylalkyl, alkyl, arylalkoxyalkyl wherein the aryl portion of arylalkoxyalkyl is phenyl or naphtyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl; and R$_4$ is heteroaryl wherein said heteroaryl is selected from the group consisting of imidazolyl, oxazolyl, pyrazolyl, pyridinyl, thiazolyl, and thienyl; wherein any one of said heteroaryl, cycloalkyl moiety of said cycloalkylalkyl, and aryl moieties of said arylalkoxyalkyl and arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

In another embodiment, the present invention discloses compounds of formula IV, or a pharmaceutically acceptable salt, prodrug, salt of a prodrug, or a combination thereof, wherein R$_1$ is heteroaryl wherein said heteroaryl is thiazol-5-yl; R$_2$ is arylalkyl wherein the aryl portion of arylalkyl is phenyl or naphthyl; R$_3$ is arylalkyl wherein the aryl portion of arylalkyl is phenyl or naphthyl; and R$_4$ is heteroaryl wherein said heteroaryl is thiazol-5-yl; wherein any one of said heteroaryl, and aryl moiety of said arylalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are as defined in formula I.

Representative examples of the present invention include, but are not limited to, the following:

N-ethyl-N,N-bis[(2S)-2-(thiazol-5-ylmethoxycarbonylamino)-3-phenylpropyl]amine;

N-ethyl-N,N-bis[(2S)-2-(oxazol-5-ylmethoxycarbonylamino)-3-phenylpropyl]amine;

N-ethyl-N,N-bis[(2S)-2-(thien-2-ylmethoxycarbonylamino)-3-phenylpropyl]amine;

N-ethyl-N,N-bis[(2S)-2-(pyridin-3-ylmethoxycarbonylamino)-3-phenylpropyl]amine;

N-ethyl-N,N-bis[(2S)-2-(1H-imidazol-4-ylmethoxycarbonylamino)-3-phenylpropyl]amine;

N-ethyl-N,N-bis[(2S)-2-(pyrazol-5-ylmethoxycarbonylamino)-3-phenylpropyl]amine;

N-(2,2-dimethylpropyl)-N,N-bis[(2S)-2-(thiazol-5-ylmethoxycarbonylamino)-3-phenylpropyl]amine and N-(2,2-dimethylpropyl)-N,N-bis[(2R)-2-(thiazol-5-ylmethoxycarbonylamino)-3-phenylpropyl]amine;

N-(2,2-dimethylpropyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;

N,N-bis[2-(thiazol-5-ylmethoxycarbonylamino)-3-phenylpropyl]amine;

N-ethyl-N,N-bis[(2S)-2-(thiazol-5-ylmethoxycarbonylamino)-4-methylpentyl]amine;

N-ethyl-N,N-bis[(2S)-2-(thiazol-5-ylmethoxycarbonylamino)propyl]amine;

N-ethyl-N,N-bis[(2R)-2-(thiazol-5-ylmethoxycarbonylamino)propyl]amine;

N-ethyl-N-[(2R)-2-(thiazol-5-ylmethoxycarbonylamino)propyl]-N-[(2S)-2-(thiazol-5-ylmethoxycarbonylamino)propyl]amine;

N-ethyl-N,N-bis-N-[2-(thiazol-5-ylmethoxycarbonylamino)ethyl]amine;

N-ethyl-N,N-bis[2-(thiazol-5-ylmethoxycarbonylamino)-3-cyclohexylpropyl]amine;

N-ethyl-N,N-bis[2-(thiazol-5-ylmethoxycarbonylamino)-3-(methoxycarbonyl)propyl]amine;

N-ethyl-N-[(2S)-2-(thiazol-5-ylmethoxycarbonylamino)-3-(phenylmethoxy)propyl]-N-[2-(thiazol-5-ylmethoxycarbonylamino)-3-(phenylmethoxy)propyl]amine;

N-ethyl-N-[(2S)-2-(thiazol-5-ylmethoxycarbonylamino)-3-[4-(phenylmethoxy)phenyl]propyl]-N-[2-(thiazol-5-ylmethoxycarbonylamino)-3-[4-(phenylmethoxy)phenyl]propyl]amine;
N-ethyl-N-[(2S)-2-(thiazol-5-ylmethoxycarbonylamino)-3-(4-hydroxyphenyl)propyl]-N-[2-(thiazol-5-ylmethoxycarbonylamino)-3-(4-hydroxyphenyl)propyl]amine;
N-ethyl-N-[(2S)-2-(thiazol-5-ylmethoxycarbonylamino)-3-(4-methoxyphenyl)propyl]-N-[2-(thiazol-5-ylmethoxycarbonylamino)-3-(4-methoxyphenyl)propyl]amine;
N,N'-bis[2-(thiazol-5-ylmethoxycarbonylamino)-3-(phenyl)propyl]piperazine;
N,N'-diethyl-N,N'-bis[2-(thiazol-5-ylmethoxycarbonylamino)-3-phenylpropyl]ethylenediamine;
N,N'-diisopropyl-N,N'-bis[2-(thiazol-5-ylmethoxycarbonylamino)-3-phenylpropyl]ethylenediamine;
N,N'-bis-[2-(thiazol-5-ylmethoxycarbonylamino)-3-phenylpropyl]-N-(thiazol-5-ylmethoxycarbonyl)ethylenediamine;
tris-N-[2-(thiazol-5-ylmethoxycarbonylamino)-3-phenylpropyl]amine;
N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(2-methylpropyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(3-methylbutyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-benzyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N,N-bis-[(2R)-2-(thiazol-5-ylmethoxycarbonylamino)-3-phenylpropyl]amine;
N-(2-methylpropyl)-N,N-bis[(2R)-2-(thiazol-5-ylmethoxycarbonylamino)-3-phenylpropyl]amine;
N-(3-methylbutyl)-N,N-bis[(2R)-2-(thiazol-5-ylmethoxycarbonylamino)-3-phenylpropyl]amine;
N-benzyl-N,N-bis[(2R)-2-(thiazol-5-ylmethoxycarbonylamino)-3-phenylpropyl]amine;
N,N-bis[(2S)-2-(thiazol-5-ylmethoxycarbonylamino)-3-phenylpropyl]amine;
N-(thiazol-5-ylmethoxycarbonyl)-N,N-bis[(2S)-2-(thiazol-5-ylmethoxycarbonylamino)-3-phenylpropyl]amine;
N-acetyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-benzoyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(2-methylpropyl)-N,N-bis[(2S)-2-(thiazol-5-ylmethoxycarbonylamino)-3-phenylpropyl]amine;
N-(2-phenylethyl)-N,N-bis[(2S)-2-(thiazol-5-ylmethoxycarbonylamino)-3-phenylpropyl]amine;
N-(2-ethylbutyl)-N,N-bis[(2S)-2-(thiazol-5-ylmethoxycarbonylamino)-3-phenylpropyl]amine;
N-(4-pentenyl)-N,N-bis[(2S)-2-(thiazol-5-ylmethoxycarbonylamino)-3-phenylpropyl]amine;
N-(3-carboxypropyl)-N,N-bis[(2S)-2-(thiazol-5-ylmethoxycarbonylamino)-3-phenylpropyl]amine;
N-(1H-imidazol-4-ylmethyl)-N,N-bis[(2S)-2-(thiazol-5-ylmethoxycarbonylamino)-3-phenylpropyl]amine;
N-(3-pyridinylmethyl)-N,N-bis[(2S)-2-(thiazol-5-ylmethoxycarbonylamino)-3-phenylpropyl]amine;
N-(4-pyridinylmethyl)-N,N-bis[(2S)-2-(thiazol-5-ylmethoxycarbonylamino)-3-phenylpropyl]amine;
N-(1H-pyrrol-2-ylmethyl)-N,N-bis[(2S)-2-(thiazol-5-ylmethoxycarbonylamino)-3-phenylpropyl]amine;
N-butyl-N,N-bis[(2S)-2-(thiazol-5-ylmethoxycarbonylamino)-3-phenylpropyl]amine;
N-octyl-N,N-bis[(2S)-2-(thiazol-5-ylmethoxycarbonylamino)-3-phenylpropyl]amine;
N-[(2,5-dimethoxytetrahydro-3-furanyl)methyl]-N,N-bis[(2S)-2-(thiazol-5-ylmethoxycarbonylamino)-3-phenylpropyl]amine;
N-(cyclopropylmethyl)-N,N-bis[(2S)-2-(thiazol-5-ylmethoxycarbonylamino)-3-phenylpropyl]amine;
N-(3,5,5-trimethylhexyl)-N,N-bis[(2S)-2-(thiazol-5-ylmethoxycarbonylamino)-3-phenylpropyl]amine;
N-(2,2-dimethyl-4-pentenyl)-N,N-bis[(2S)-2-(thiazol-5-ylmethoxycarbonylamino)-3-phenylpropyl]amine;
N-[2-((tert-butoxycarbonyl)amino)ethyl]-N,N-bis-[(2S)-2-(thiazol-5-ylmethoxycarbonylamino)-3-phenylpropyl]amine;
N-[3-(1,3-benzodioxol-5-yl)-2-methylpropyl]-N,N-bis[(2S)-2-(thiazol-5-ylmethoxycarbonylamino)-3-phenylpropyl]amine;
N-(6-methoxy-6-oxohexyl)-N,N-bis[(2S)-2-(thiazol-5-ylmethoxycarbonylamino)-3-phenylpropyl]amine;
N-[4-ethoxy-2-(ethoxycarbonyl)-4-oxobutyl]-N,N-bis[(2S)-2-(thiazol-5-ylmethoxycarbonylamino)-3-phenylpropyl]amine;
N-(3,5-ditert-butyl-2-hydroxybenzyl)-N,N-bis[(2S)-2-(thiazol-5-ylmethoxycarbonylamino)-3-phenylpropyl]amine;
N-(2-naphthylmethyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(3-phenoxybenzyl)-N-[(2R)-2-(thiazol-5-ylmethoxycarbonylamino)-3-phenylpropyl]-N-[(2S)-2-(thiazol-5-ylmethoxycarbonylamino)]amine;
N-(3-quinolinylmethyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(3-methoxybenzyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(3,4-dimethoxybenzyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-[4-(3-(dimethylamino)propoxy)benzyl]-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(4-dimethylaminobenzyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-[(6-methoxy-2-naphthyl)methyl]-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine;
N-(3-methylbutyl)-N,N-bis[(2S)-2-(thiazol-5-ylmethoxycarbonylamino)-3-phenylpropyl]amine;
N-benzyl-N,N-bis[(2S)-2-(thiazol-5-ylmethoxycarbonylamino)-3-phenylpropyl]amine;
N-(cyclohexylmethyl)-N,N-bis[(2S)-2-(thiazol-5-ylmethoxycarbonylamino)-3-phenylpropyl]amine;
N-ethyl-N,N-bis[(2R)-2-(thiazol-5-ylmethoxycarbonylamino)-3-phenylpropyl]amine;
N-ethyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine; or a pharmaceutically acceptable salt, prodrug, salt of a prodrug, or combination thereof.

In one embodiment, the present invention discloses a method for improving the pharmacokinetics of a drug which is metabolized by cytochrome P450 monooxygenase comprising co-administering to a human in need of such treatment a combination of a therapeutically effective amount of said drug or a pharmaceutically acceptable salt thereof, and an amount of a compound or combination of compounds of the present invention or a pharmaceutically acceptable salt, prodrug, salt of a prodrug, or combination thereof, effective to inhibit cytochrome P450 monooxygenase.

In another embodiment, the present invention discloses a method for increasing human blood levels of a drug which is metabolized by cytochrome P450 monooxygenase comprising co-administering to a human in need of such treatment a combination of a therapeutically effective amount of said drug or a pharmaceutically acceptable salt thereof, and an amount of a compound or combination of compounds of the present invention, or a pharmaceutically acceptable salt, prodrug, salt of a prodrug, or combination thereof, effective to inhibit cytochrome P450 monooxygenase.

In another embodiment, the present invention discloses a method for inhibiting cytochrome P450 monooxygenase comprising administering to a human in need thereof an amount of a compound or combination of compounds of the present invention or a pharmaceutically acceptable salt, prodrug, salt of a prodrug, or combination thereof effective to inhibit cytochrome P450 monooxygenase.

In another embodiment, the present invention discloses a method for inhibiting cytochrome P450 monooxygenase comprising contacting the cytochrome P450 monooxygenase with an amount of a compound or combination of compounds of the present invention or a pharmaceutically acceptable salt, prodrug, salt of a prodrug, or combination thereof effective to inhibit cytochrome P450 monooxygenase.

Examples of drugs which are metabolized by cytochrome P450 monooxygenase and which benefit from coadministration with compounds of formula (I) (II) or (III), include the immunosuppressants cyclosporine, FK-506, FK-565, and rapamycin, the chemotherapeutic agents (e.g. taxol and taxotere), the antibiotic clarithromycin, the HIV protease inhibitors such as lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, SC-52151, BMS 186,318, SC-55389a, BILA 1096 BS, DMP-323, KNI-227, and the like, and other therapeutic agents such as capravirine, calanolide, sildenafil, vardenafil and tadalafil.

Accordingly, another embodiment of the present invention discloses a method for improving the pharmacokinetics of an HIV protease inhibitor (or a pharmaceutically acceptables salt thereof) which is metabolized by cytochrome P450 monooxygenase comprising coadministering a compound or combination of compounds of formula I, II or III, (or a pharmaceutically acceptable salt, prodrug, salt of a prodrug, or a combination thereof). Such a combination of a compound or combination of compounds of formula I, II or III, (or a pharmaceutically acceptable salt, prodrug, salt of a prodrug, or a combination thereof) and an HIV protease inhibitor or a pharmaceutically acceptable salt thereof which is metabolized by cytochrome P450 monooxygenase is useful for inhibiting HIV protease in human and is also useful for inhibition, treatment or prophylaxis of an HIV infection or AIDS (acquired immune deficiency syndrome) in humans.

When administered in combination, the drug (or a pharmaceutically acceptable salt thereof) that is metabolized by cytochrome P450 monooxygenase and the compound or combination of compounds (or a pharmaceutically acceptable salt, prodrug, salt of a prodrug, or a combination thereof) of the present invention can be formulated as separate compositions which are administered at the same time or different times, or can be administered as a single composition.

The term "treating" as used herein, refers to reversing, alleviating, inhibiting the progress of, or preventing the disorder or condition, or one or more symptoms of such disorder or condition to which such term applies. The term "treatment", as used herein, refers to the act of treating, as "treating" is defined immediately above.

As used throughout this specification and the appended claims, the following terms have the following meanings:

The term "alkenyl" as used herein, refers to a straight or branched chain hydrocarbon containing 2, 3, 4, 5, 6, 7, 8, 9 or 10 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 2,2-dimethyl-4-pentenyl, 5-hexenyl, 2-heptenyl, 2-methyl-1-heptenyl, 3-decenyl and the like.

The term "alkenylcarbonyl" as used herein, refers to an alkenyl group, as defined herein, appended to the parent molecular moiety through a carbonyl group, as defined herein. Representative examples of alkenylcarbonyl include, but are not limited to, acryloyl, but-3-enoyl, pent-3-enoyl, and the like.

The term "alkoxy" as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkyl" as used herein, refers to an alkoxy group, as defined herein, appended to the parent molecular moiety through an alkylene, as defined herein. Representative examples of alkoxyalkyl include, but are not limited to, tert-butoxymethyl, 2-ethoxyethyl, 2-methoxyethyl, methoxymethyl and the like.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl and the like.

The term "alkoxycarbonylalkyl" as used herein, refers an alkoxycarbonyl group, as defined herein, appended to the parent molecular moiety through an alkylene group, as defined herein. Representative examples of alkoxycarbonylalkyl include, but are not limited to, 2-methoxy-2-oxoethyl, 2-ethoxy-2-oxoethyl, 3-methoxy-3-oxopropyl, 3-ethoxy-3-oxopropyl, 4-ethoxy-2-(ethoxycarbonyl)-4-oxobutyl, 5-methoxy-5-oxopentyl, 6-methoxy-6-oxohexyl and the like.

The term "alkyl" as used herein, refers to a straight or branched chain hydrocarbon containing 1, 2, 3, 4, 5, 6, 7, 8, 9, or 10 carbon atoms. Representative examples of alkyl include, but are not limited to, methyl, ethyl, propyl, isopropyl, butyl, 2-methylpropyl, 2,2-dimethylpropyl, 3-methylbutyl, 2-ethylbutyl, pentyl, hexyl, 3-methylhexyl, 3,5,5-trimethylhexyl, 2,2-dimethylpentyl, 2,3-dimethylpentyl, heptyl, octyl, nonyl, decyl and the like.

The term "alkylcarbonyl" as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl and the like.

The term "alkylcarbonylalkyl" as used herein, refers to an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, 3-oxopentyl and the like.

The term "alkylcarbonyloxy" as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, tert-butylcarbonyloxy and the like.

The term "alkylcarbonyloxyalkyl" as used herein, refers to an alkylcarbonyloxy group, as defined herein, appended to the parent molecular moiety through an alkylene moiety, as defined herein. Representative examples of alkylcarbonyloxyalkyl include, but are not limited to, 2-(acetyloxy)ethyl, 3-(acetyloxy)propyl, 3-(propionyloxy)propyl and the like.

The term "alkylene" denotes a divalent group derived from a straight or branched, saturated hydrocarbon chain of 1, 2, 3, 4, 5, 6, 7, 8, 9 or 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH$_2$CH(CH$_3$)CH$_2$— and the like The term "alkynyl" as used herein, refers to a straight or branched chain hydrocarbon group containing 2, 3, 4, 5, 6, 7, 8, 9 or 10 carbon atoms and containing at least one carbon-carbon triple bond. Representative examples of alkynyl include, but are not limited, to ethynyl, 1-propynyl, 2-propynyl, 3-butynyl, 2-pentynyl, 1-butynyl and the like.

The term "alkynylcarbonyl" as used herein, refers to an alkynyl group, as defined herein, appended to the parent molecular moiety through a carbonyl group, as defined herein. Representative examples of alkynylcarbonyl include, but are not limited to, prop-2-ynoyl, but-2-ynoyl, pent-3-ynoyl, and the like.

The term "aryl" as used herein, refers to a phenyl group, a bicyclic hydrocarbon fused ring system, or a tricyclic hydrocarbon fused ring system wherein one or more of the rings are a phenyl group. The term "aryl" also includes a bicyclic hydrocarbon fused ring system in which a phenyl group is fused to a monocyclic 5- or 6-membered cycloalkenyl group, as defined herein, a 5- or 6-membered monocyclic cycloalkyl group, as defined herein, or another phenyl group. The term "aryl" also includes a tricyclic hydrocarbon fused ring system in which any one of the above bicyclic aryl groups is fused to a 5- or 6-membered monocyclic cycloalkyl group, as defined herein, or a 5- or 6-membered monocyclic cycloalkenyl group, as defined herein, or another phenyl group. Representative examples of aryl groups include, but not limited to, anthracenyl, fluorenyl, indanyl, indenyl, naphthyl, phenyl and tetrahydronaphthyl. The aryl groups of the present invention can be substituted or unsubstituted, and are connected to the parent molecular moiety through any substitutable carbon atom of the group.

The term "arylalkoxy" as used herein, refers to an alkoxy group, as defined herein, to which is appended an aryl group, as defined herein. Representative examples of arylalkoxy include, but are not limited to, 2-phenylethoxy, 3-naphth-2-ylpropoxy, 5-phenylpentyloxy and the like.

The term "arylalkoxyalkyl" as used herein, refers to an arylalkoxy group, as defined herein, appended to the parent molecular moiety through an alkylene group, as defined herein. Representative examples of arylalkoxyalkyl include, but are not limited to, benzyloxymethyl, 2-(benzyloxy)ethyl, (2-phenylethoxy)methyl and the like.

The term "arylalkoxycarbonyl" as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, naphth-2-ylmethoxycarbonyl and the like.

The term "arylalkyl" as used herein, refers to an aryl group, as defined herein, appended to the parent molecular moiety through an alkylene group, as defined herein. Representative examples of arylalkyl include, but are not limited to, benzyl, 4-(benzyloxy)benzyl, 4-methoxybenzyl, 4-hydroxybenzyl, 3-(1,3-benzodioxol-5-yl)-2-methylpropyl, 3-(phenoxy)benzyl, 3-(1,3-benzodioxol-5-yl)propyl, 2-phenylethyl, 3-phenylpropyl, 2-naphthylmethyl, 3,5-ditert-butyl-2-hydroxybenzyl, 3-methoxybenzyl, 3,4-dimethoxybenzyl, 4-(dimethylamino)benzyl, 4-[3-(dimethylamino)propoxy]benzyl, (6-methoxy-2-naphthyl)methyl, 2-naphth-2-ylethyl and the like.

The term "arylalkylcarbonyl" as used herein, refers to an arylalkyl group, as defined herein, appended to the parent molecular moiety through a carbonyl group, as defined herein. Representative examples of arylalkylcarbonyl include, but are not limited to, 2-naphthylacetyl, phenylacetyl and the like.

The term "arylcarbonyl" as used herein, refers to an aryl group, as defined herein, appended to the parent molecular moiety through a carbonyl group, as defined herein. Representative examples of arylcarbonyl include, but are not limited to, benzoyl, naphthoyl and the like.

The term "aryloxy" as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, 3,5-dimethoxyphenoxy and the like.

The term "aryloxyalkyl" as used herein, refers to an aryloxy group, as defined herein, appended to the parent molecular moiety through an alkylene group, as defined herein. Representative examples of aryloxyalkyl include, but are not limited to, 2-phenoxyethyl, 3-naphth-2-yloxypropyl, 3-bromophenoxymethyl and the like.

The term "aryloxycarbonyl" as used herein, refers to an aryloxy group, as defined herein, appended to the parent molecular moiety through a carbonyl group, as defined herein.

The term "arylthio" as used herein, refers to an aryl group, as defined herein, appended to the parent molecular moiety through a sulfur atom. Representative examples of arylthio include, but are not limited to, phenylthio, naphthalen-1-ylthio, naphthalen-2-ylthio and the like.

The term "arylthioalkoxy" as used herein, refers to a thioalkoxy group, as defined herein, to which is appended an aryl group, as defined herein. Representative examples of arylthioalkoxy include, but are not limited to, (phenylmethyl)thio, (2-phenylethyl)thio, (naphthalen-1-ylmethyl)thio and the like.

The term "arylthioalkoxyalkyl" as used herein, refers to an arylthioalkoxy group, as defined herein, appended to the parent molecular moiety through an alkylene group, as defined herein. Representative examples of arylthioalkoxy include, but are not limited to, (phenylmethyl)thiomethyl, (2-phenylethyl)thiomethyl, (naphthalen-1-ylmethyl)thiomethyl and the like.

The term "arylthioalkyl" as used herein, refers to an arylthio group, as defined herein, appended to the parent molecular moiety through an alkylene group, as defined herein. Representative examples of arylthioalkyl include, but are not limited to, (phenylthio)methyl, 2-(phenylthio)ethyl, 3-(phenylthio)propyl and the like.

The term "carbonyl" as used herein, refers to a —C(O)— group.

The term "carboxy" as used herein, refers to a —CO$_2$H group.

The term "carboxyalkyl" as used herein, refers to a carboxy group, as defined herein, appended to the parent molecular moiety through an alkylene group, as defined herein. Representative examples of carboxyalkyl include, but are not limited to, carboxymethyl, 2-carboxyethyl, 3-carboxypropyl and the like.

The term "cyano" as used herein, refers to a —CN group.

The term "cyanoalkyl" as used herein, refers to a cyano group, as defined herein, appended to the parent molecular moiety through an alkylene group, as defined herein. Representative examples of cyanoalkyl include, but are not limited to, cyanomethyl, 2-cyanoethyl, 3-cyanopropyl and the like.

The term "cycloalkenyl," as used herein, refers to a non-aromatic, partially unsaturated, monocyclic hydrocarbon ring system, having 4, 5, 6, 7, 8, 9 or 10 carbon atoms and zero heteroatom. Representative examples of cycloalkenyl groups include, but not limited to, cyclobutenyl, cyclopentenyl, cyclohexenyl, and octahydronaphthalenyl. The cycloalkenyl groups of the present invention can be unsubstituted or substituted, and are attached to the parent molecular moiety through any substitutable carbon atom of the group.

The term "cycloalkyl" as used herein, refers to a saturated, monocyclic or bicyclic hydrocarbon group containing from 3, 4, 5, 6, 7 or 8 carbon atoms and zero heteroatom. The cycloalkyl groups of the present invention can be unsubstituted or substituted and are connected to the parent molecular moiety through any one or more of the substitutable atoms of the groups. Examples of cycloalkyl include cyclopropyl, cyclobutyl, cyclopentyl, cyclohexyl, cycloheptyl, cyclooctyl and the like.

The term "cycloalkylalkyl" as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, 4-cycloheptylbutyl and the like.

The term "cycloalkylcarbonyl" as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, cyclohexylcarbonyl and the like.

The term "di(alkoxycarbonyl)alkyl" as used herein, refers to two independent alkoxycarbonyl groups, as defined herein, appended to the parent molecular moiety through an alkyl group, as defined herein. Representative examples of di(alkoxycarbonyl)alkyl include, but are not limited to, 4-ethyoxy-2-(ethyoxycarbonyl)-4-oxobutyl, 4-(ethyloxy)-2-((methyloxy)carbonyl)-4-oxobutyl, 5-(ethyloxy)-3-((ethyloxy)carbonyl)-5-oxopentyl and the like.

The term "ethylenedioxy" as used herein, refers to a —O(CH$_2$)$_2$O— group, wherein the oxygen atoms of the ethylenedioxy group are attached to the parent molecular moiety through two adjacent carbon atoms of the parent molecular moiety, forming a six membered ring.

The term "formyl" as used herein, refers to a —C(O)H group.

The term "halo" or "halogen" as used herein, refers to —Cl, —Br, —I or —F.

The term "haloalkoxy" as used herein, refers to an alkoxy group, as defined herein, in which one or more hydrogen atoms is replaced with a halogen, as defined herein. Representative examples of haloalkoxy include, but are not limited to, chloromethoxy, fluoromethoxy, difluoromethoxy, 2-fluoroethoxy, trifluoromethoxy, pentafluoroethoxy and the like.

The term "haloalkyl" as used herein, refers to an alkyl group, as defined herein, in which one or more hydrogen atoms is replaced with a halogen, as defined herein. Representative examples of haloalkyl include, but are not limited to, chloromethyl, fluoromethyl, difluoromethyl, 2-fluoroethyl, trifluoromethyl, pentafluoroethyl, 2-chloro-3-fluoropentyl and the like.

The term "heterocycle" or "heterocyclic ring" or "heterocyclic" as used herein, refers to a monocyclic, bicyclic or tricyclic non-aromatic, saturated or partially unsaturated ring system. Monocyclic ring systems are exemplified by any 3- or 4-membered ring containing a heteroatom independently selected from oxygen, nitrogen and sulfur; or a 5-, 6-, 7-, or 8-membered ring containing one, two or three heteroatoms wherein the heteroatoms are independently selected from nitrogen, oxygen and sulfur. The 5-membered ring has 0 or 1 double bond. The 6-membered ring has 0, 1 or 2 double bonds. The 7- or 8-membered ring has 0, 1, 2 or 3 double bonds. Representative examples of monocyclic ring systems include, but are not limited to, aziridinyl, azetidinyl, azepanyl, azepinyl, diazepinyl, 1,3-dioxolanyl, dioxanyl, dithianyl, imidazolinyl, imidazolidinyl, isothiazolinyl, isothiazolidinyl, isoxazolinyl, isoxazolidinyl, morpholinyl, 3-oxo-morpholinyl, oxadiazolinyl, oxadiazolidinyl, oxazolinyl, 2-oxo-oxazolinyl, oxazolidinyl, piperazinyl, piperidyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, 1,4-diazepanyl, trithianyl and the like. The term "heterocycle" also includes bicyclic heterocyclic ring systems in which any of the above heterocyclic rings is fused to a phenyl group, a 5- or 6-membered monocyclic cycloalkenyl group, as defined herein, a 5- or 6-membered monocyclic cycloalkyl group, as defined herein, or an additional monocyclic heterocycle group, as defined herein. Representative examples of bicyclic heterocyclic ring systems include but are not limited to, benzodioxinyl, benzopyranyl, benzothiopyranyl, 2,3-dihydroindolyl, indolizinyl, pyranopyridinyl, and the like. The term "heterocycle" also includes tricyclic heterocyclic ring systems in which any one of the above bicyclic heterocyclic ring systems is fused to a phenyl ring, a 5- or 6-membered cycloalkyl group, as defined herein, a 5- or 6-membered cycloalkenyl group, as defined herein, or an additional monocyclic heterocycle group, as defined herein. Representative examples of tricyclic heterocyclic ring systems include, but are not limited to, phenazinyl, thioanthrenyl, thioxanthenyl, xanthenyl, and the like. The heterocycle groups of the invention are independently substituted or unsubstituted, and are connected to the parent molecular moiety through any substitutable carbon or nitrogen atom in the groups. The nitrogen heteroatom may or may not be quaternized, and may or may not be oxidized to the N-oxide. In addition, the nitrogen containing heterocyclic rings may or may not be N-protected.

The term "heterocyclealkoxy" as used herein, refers to an alkoxy group, as defined herein, to which is appended a heterocycle, as defined herein. Representative examples of heterocyclealkoxy include, but are not limited to, 2-piperidinylethoxy and the like.

The term "heterocyclealkoxyalkyl" as used herein, refers to a heterocyclealkoxy group, as defined herein, appended to the parent molecular moiety through an alkylene group, as defined herein. Representative examples of heterocyclealkoxyalkyl include, but are not limited to, (2-piperidinylethoxy)methyl and the like.

The term "heterocyclealkoxycarbonyl" as used herein, refers to a heterocyclealkoxy group, as defined herein, appended to the parent molecular moiety through a carbonyl group, as defined herein. Representative examples of heterocyclealkoxycarbonyl include, but are not limited to, (2-piperidinylethoxy)carbonyl, (3-piperazinylpropoxy)carbonyl and the like.

The term "heterocyclealkyl" as used herein, refers to a heterocycle, as defined herein, appended to the parent molecular moiety through an alkylene group, as defined herein. Representative examples of heterocyclealkyl include, but are not limited to, (2,5-dimethoxytetrahydro-3-furanyl) methyl and the like.

The term "heterocyclealkylcarbonyl" as used herein, refers to a heterocyclealkyl group, as defined herein, appended to the parent molecular moiety through a carbonyl group, as defined herein. Representative examples of heterocyclealkylcarbonyl include, but are not limited to, ((2,5-dimethoxytetrahydro-3-furanyl)methyl)carbonyl and the like.

The term "heterocyclecarbonyl" as used herein, refers to a heterocycle, as defined herein, appended to the parent molecular moiety through a carbonyl group, as defined herein. Representative examples of heterocyclecarbonyl include, but are not limited to, 2,3-dihydrothienylcarbonyl and the like.

The term "heterocycleoxy" as used herein, refers to a heterocycle group, as defined herein, appended to the parent molecular moiety through an oxy moiety, as defined herein. Representative examples of heterocycleoxy include, but are not limited to, 2,3-dihydrothienyloxy and the like.

The term "heterocycleoxyalkyl" as used herein, refers to a heterocycleoxy group, as defined herein, appended to the parent molecular moiety through an alkylene group, as defined herein. Representative examples of heterocycleoxyalkyl include, but are not limited to, 2,3-dihydrothienyloxymethyl and the like.

The term "heterocycleoxycarbonyl" as used herein, refers to a heterocycleoxy group, as defined herein, appended to the parent molecular moiety through a carbonyl group, as defined herein.

The term "heterocyclethio" as used herein, refers to a heterocycle, as defined herein, appended to the parent molecular moiety through a sulfur atom.

The term "heterocyclethioalkoxy" as used herein, refers to a thioalkoxy group, as defined herein, to which is appended a heterocycle, as defined herein.

The term "heterocyclethioalkoxyalkyl" as used herein, refers to a heterocyclethioalkoxy group, as defined herein, appended to the parent molecular moiety through an alkylene group, as defined herein.

The term "heterocyclethioalkyl" as used herein, refers to a heterocyclethio group, as defined herein, appended to the parent molecular moiety through an alkylene group, as defined herein.

The term "hydroxy" as used herein, refers to an —OH group.

The term "heteroaryl" as used herein, refers to an aromatic five- or six-membered ring where at least one atom is selected from the group consisting of N, O, and S, and the remaining atoms are carbon. The five membered rings have two double bonds, and the six membered rings have three double bonds. Representative examples of the monocyclic heteroaryl groups include, but are not limited to, furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, thiazolyl, thienyl, 1,3,5-triazinyl, and the like. The term "heteroaryl" also includes bicyclic fused ring systems where a heteroaryl ring is fused to a phenyl group, a 5- or 6-membered monocyclic cycloalkenyl group, as defined herein, a 5- or 6-membered monocyclic cycloalkyl group, as defined herein, a 5- or 6-membered monocyclic heterocycle group, as defined herein, or an additional heteroaryl group. Representative examples of heteroaryl groups include, but not limited to, benzimidazolyl, benzothiazolyl, benzothienyl, benzoxazolyl, benzofuranyl, benzoxadiazolyl, imidazo[1,2-a]pyridinyl, indazolyl, indolyl, isoindolyl, isoquinolinyl, isothiazolyl, naphthyridinyl, oxadiazolyl, oxazolyl, pyridoimidazolyl, quinolinyl, quinolizinyl, quinoxalinyl, quinazolinyl, thienopyridinyl, and the like. The term "heteroaryl" also includes tricyclic fused ring systems in which any of the above bicyclic heteroaryl ring systems, as defined hereabove, is fused to a phenyl group, a 5- or 6-membered monocyclic cycloalkyl group, as defined herein, a 5- or 6-membered monocyclic cycloalkenyl group, as defined herein, a 5- or 6-membered monocyclic heterocyclic group, or an additional 5- or 6-membered monocyclic heteroaryl group, as defined herein. Representative examples of the tricyclic heteroaryl groups include, but are not limited to, dibenzothienyl, dibenzofuranyl, and the like. The heteroaryl groups of the present invention can be independently substituted or unsubstituted, and are connected to the parent molecular moiety through any substitutable carbon or nitrogen atom in the groups. In addition, the nitrogen heteroatom may or may not be quaternized, and may or may not be oxidized to the N-oxide. Also, the nitrogen containing rings may or may not be N-protected.

The term "heteroarylalkoxy" as used herein, refers to an alkoxy group, as defined herein, to which is appended a heteroaryl group, as defined herein. Representative examples of heteroarylalkoxy include, but are not limited to, 2-pyridin-3-ylethoxy, 1,3-thiazol-5-ylmethoxy, 3-quinolin-3-ylpropoxy, 5-pyridin-4-ylpentyloxy and the like.

The term "heteroarylalkoxyalkyl" as used herein, refers to a heteroarylalkoxy group, as defined herein, appended to the parent molecular moiety through an alkylene group, as defined herein. Representative examples of heteroarylalkoxyalkyl include, but are not limited to, (2-pyridin-3-ylethoxy)methyl, (3-quinolin-3-ylpropoxy)methyl, (1,3-thiazol-5-ylmethoxy)methyl, 2-(5-pyridin-4-ylpentyloxy) ethyl and the like.

The term "heteroarylalkoxycarbonyl" as used herein, refers to a heteroarylalkoxy group, as defined herein, appended to the parent molecular moiety through a carbonyl group, as defined herein. Representative examples of heteroarylalkoxycarbonyl include, but are not limited to, (2-pyridin-3-ylethoxy)carbonyl, (3-quinolin-3-ylpropoxy)carbonyl, 2-(1,3-thiazol-5-ylmethoxy)carbonyl, (5-pyridin-4-ylpentyloxy)carbonyl and the like.

The term "heteroarylalkyl" as used herein, refers to a heteroaryl group, as defined herein, appended to the parent molecular moiety through an alkylene group, as defined herein. Representative examples of heteroarylalkyl include, but are not limited to, 3-quinolinylmethyl, 3-pyridinylmethyl, 4-pyridinylmethyl, 1H-imidazol-4-ylmethyl, 1H-pyrrol-2-ylmethyl, pyridin-3-ylmethyl, 2-pyrimidin-2-ylpropyl and the like.

The term "heteroarylalkylcarbonyl" as used herein, refers to a heteroarylalkyl group, as defined herein, appended to the parent molecular moiety through a carbonyl group, as defined herein. Representative examples of heteroarylalkylcarbonyl include, but are not limited to, ((2,5-dimethoxytetrahydro-3-furanyl)methyl)carbonyl, (3-quinolinylmethyl)carbonyl, (3-pyridinylmethyl)carbonyl, (4-pyridinylmethyl)carbonyl, (1H-imidazol-4-ylmethyl)carbonyl, (1H-pyrrol-2-ylmethyl)carbonyl, (pyridin-3-ylmethyl)carbonyl, (2-pyrimidin-2-ylpropyl)carbonyl and the like.

The term "heteroarylcarbonyl" as used herein, refers to a heteroaryl group, as defined herein, appended to the parent molecular moiety through a carbonyl group, as defined herein. Representative examples of heteroarylcarbonyl include, but are not limited to, pyridin-3-ylcarbonyl, (1,3-thiazol-5-yl)carbonyl, quinolin-3-ylcarbonyl and the like.

The term "heteroaryloxy" as used herein, refers to a heteroaryl group, as defined herein, appended to the parent molecular moiety through an oxy moiety, as defined herein. Representative examples of heteroaryloxy include, but are not limited to, pyridin-3-yloxy, quinolin-3-yloxy and the like.

The term "heteroaryloxyalkyl" as used herein, refers to a heteroaryloxy group, as defined herein, appended to the parent molecular moiety through an alkylene group, as defined herein. Representative examples of heteroaryloxyalkyl include, but are not limited to, pyridin-3-yloxymethyl, 2-quinolin-3-yloxyethyl and the like.

The term "heteroaryloxycarbonyl" as used herein, refers to a heteroaryloxy group, as defined herein, appended to the parent molecular moiety through a carbonyl group, as defined herein.

The term "heteroarylthio" as used herein, refers to a heteroaryl group, as defined herein, appended to the parent molecular moiety through a sulfur atom. Representative examples of heteroarylthio include, but are not limited to, (3-quinolinyl)thio, (3-pyridinyl)thio, (4-pyridinyl)thio and the like.

The term "heteroarylthioalkoxy" as used herein, refers to a thioalkoxy group, as defined herein, to which is appended a heteroaryl group, as defined herein. Representative examples of heteroarylthioalkoxy include, but are not limited to, 2-pyridin-3-ylethylthio, 1,3-thiazol-5-ylmethylthio, 3-quinolin-3-ylpropylthio, 5-pyridin-4-ylpentylylthio and the like.

The term "heteroarylthioalkoxyalkyl" as used herein, refers to a heteroarylthioalkoxy group, as defined herein, appended to the parent molecular moiety through an alkylene group, as defined herein. Representative examples of heteroarylthioalkoxyalkyl include, but are not limited to, (2-pyridin-3-ylethylthio)methyl, (3-quinolin-3-ylpropylthio)methyl, (1,3-thiazol-5-ylmethylthio)methyl, 2-(5-pyridin-4-ylpentylthio)ethyl and the like.

The term "heteroarylthioalkyl" as used herein, refers to a heteroarylthio group, as defined herein, appended to the parent molecular moiety through an alkylene group, as defined herein. Representative examples of heteroarylthioalkyl include, but are not limited to, (3-quinolinyl)thiomethyl, (3-pyridinyl)thiomethyl, (4-pyridinyl)thiomethyl, 2-((4-pyridinyl)thio)ethyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis*, 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "hydroxyalkyl" as used herein, refers to a hydroxy group, as defined herein, appended to the parent molecular moiety through an alkylene group, as defined herein. Representative examples of hydroxyalkyl include, but are not limited to, hydroxymethyl, 2-hydroxyethyl, 3-hydroxypropyl, 2-ethyl-4-hydroxyheptyl and the like.

The term "lower alkyl" as used herein, is a subset of alkyl as defined herein and refers to a straight or branched chain hydrocarbon group containing 1, 2, 3, 4, 5 or 6 carbon atoms. Representative examples of lower alkyl include, but are not limited to, methyl, ethyl, n-propyl, iso-propyl, n-butyl, iso-butyl, sec-butyl, tert-butyl and the like.

The term "mercapto" as used herein, refers to a —SH group.

The term "methylenedioxy" as used herein, refers to a —OCH$_2$O— group, wherein the oxygen atoms of the methylenedioxy are attached to the parent molecular moiety through two adjacent carbon atoms of the parent molecular moiety, forming a five-membered ring.

The term "nitro" as used herein, refers to a —NO$_2$ group.

The term "—NR$_C$R$_D$" as used herein, refers to two groups, R$_C$ and R$_D$, which are appended to the parent molecular moiety through a nitrogen atom. R$_C$ and R$_D$ are independently selected from hydrogen, alkoxycarbonyl, alkyl, alkylcarbonyl, alkylsulfonyl, arylalkoxycarbonyl, arylsulfonyl, formyl, (NR$_E$R$_F$)carbonyl, and (NR$_E$R$_F$)sulfonyl. Representative examples of —NR$_C$R$_D$ include, but are not limited to, amino, methylamino, acetylamino, acetyl(methyl)amino, (tert-butoxycarbonyl)amino, (benzyloxycarbony)amino, formylamino, (aminosulfonyl)amino, (dimethylaminosulfonyl)amino, (phenylsulfonyl)amino, (methylsulfonyl)amino, (aminocarbonyl)amino, (dimethylaminocarbonyl)amino and the like.

The term "(NR$_C$R$_D$)alkyl" as used herein, refers to a —NR$_C$R$_D$ group, as defined herein, appended to the parent molecular moiety through an alkylene group, as defined herein. Representative examples of $(NR_CR_D)$alkyl include, but are not limited to, 2-(dimethylamino)ethyl, 2-[(tert-butoxycarbonyl)amino]ethyl, 2-(acetylamino)ethyl, 2-((benzyloxycarbonyl)amino)ethyl, 2-(dimethylaminocarbonyl)ethyl, 2-((dimethylaminosulfonyl)amino)ethyl, 2-((methylsulfonyl)amino)ethyl, 2-((phenylsulfonyl)amino)ethyl and the like.

The term "—$NR_AR_B$" as used herein, refers to two groups, $R_A$ and $R_B$, which are appended to the parent molecular moiety through a nitrogen atom. $R_A$ and $R_B$ are independently selected from hydrogen and lower alkyl. Representative examples of —$NR_AR_B$ include, but are not limited to, amino, methylamino, dimethylamino, diethylamino, ethyl(methyl)amino and the like.

The term "$(NR_AR_B)$alkoxy" as used herein, refers to an alkoxy group, as defined herein, to which is appended a —$NR_AR_B$ group, as defined herein. Representative examples of $(NR_AR_B)$alkoxy include, but are not limited to, aminomethoxy, 2-(amino)ethoxy, 2-(dimethylamino)ethoxy, 3-(amino)propoxy, 3-(dimethylamino)propoxy, 4-(dimethylamino)butoxy and the like.

The term "$(NR_AR_B)$alkyl" as used herein, refers to a —$NR_AR_B$ group, as defined herein, appended to the parent molecular moiety through an alkylene group, as defined herein. Representative examples of $(NR_AR_B)$alkyl include, but are not limited to, aminomethyl, 2-(amino)ethyl, 2-(dimethylamino)ethyl, 3-(amino)propyl, 3-(dimethylamino)propyl, 4-(dimethylamino)butyl and the like.

The term "$(NR_ER_F)$carbonyl" as used herein, refers to a —$NR_ER_F$ group, wherein $R_e$ and $R_F$ are independently selected from hydrogen and lower alkyl, appended to the parent molecular moiety through a carbonyl group, as defined herein. Representative examples of $(NR_ER_F)$carbonyl include, but are not limited to, aminocarbonyl, (methylamino)carbonyl, (dimethylamino)carbonyl, (diethylamino)carbonyl, (ethyl(methyl)amino)carbonyl and the like.

The term "$(NR_ER_F)$sulfonyl" as used herein, refers to a —$NR_ER_F$ group, wherein $R_e$ and $R_F$ are independently selected from hydrogen and lower alkyl, appended to the parent molecular moiety through a sulfonyl group, as defined herein. Representative examples of $(NR_ER_F)$sulfonyl include, but are not limited to, aminosulfonyl, (methylamino)sulfonyl, (dimethylamino)sulfonyl, (diethylamino)sulfonyl, (ethyl(methyl)amino)sulfonyl and the like.

The term "oxo" as used herein, refers to a =O moiety.

The term "oxy" as used herein, refers to a —O— moiety.

The term "sulfonyl" as used herein, refers to a —$S(O)_2$— group.

The term "thioalkoxy" as used herein, refers to an alkyl group, as defined herein, appended to the parent molecular moiety through a sulfur atom. Representative examples of thioalkoxy include, but are not limited to, methylthio, ethylthio, butylthio and the like.

The term "prodrug" refers to those prodrugs or zwitterions which are suitable for use in contact with the tissues of patients without undue toxicity, irritation, and allergic response, are commensurate with a reasonable benefit/risk ratio, and are effective for their intended use. "Prodrugs" are considered to be any covalently bonded carriers which release the active parent compounds of formula I, II or III in vivo metabolically or by solvolysis when such prodrugs is administered to a mammalian subject. Prodrugs of the compounds of formula I, II or III can be prepared by modifying functional groups present in the compounds in such a way that the modifications are cleaved, either in routine manipulation or in vivo, to the parent compounds respectively. Examples of such modification include, but not limited to, treatment of a compound of formula I, II or III, containing an amino, amido or hydroxyl moiety with a suitable derivatizing agent, for example, a carboxylic acid halide or acid anhydride, treatment of a compound of formula I, II or III, containing a carboxyl moiety, to an ester or amide and treatment of a compound of formula I, II or III, containing a carboxylic acid ester moiety to an enol-ester. Prodrugs include compounds wherein hydroxy, amine, carboxy, or sulfhydryl groups are bonded to any group that, when administered to a mammalian subject, cleaves under physiological conditions to form a free hydroxyl, amino, carboxy, or sulfhydryl group, respectively. Examples of prodrugs include, but are not limited to, acetate, formate, phosphate and benzoate derivatives of the hydroxy, carboxy and amine functional groups in the compounds of formula I, II or III.

The compounds of the invention can comprise of asymmetrically substituted carbon atoms known as chiral centers. These chiral centers are designated as "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The compounds of this invention may exist as single stereoisomers (e.g., single enantiomers or single diastereomer), mixtures of stereoisomers (e.g. any mixture of enantiomers or diastereomers) or racemic mixtures. All such single stereoisomers, mixtures and racemates are intended to be encompassed within the scope of the invention. Compounds identified herein as single stereoisomers are meant to describe compounds that are present in a form that are substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound. Where the stereochemistry of the chiral carbons present in the chemical structures illustrated herein is not specified, the chemical structure is intended to encompass compounds containing either stereoisomer of each chiral center present in the compound.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate optically pure (enantiomerically pure) or substantial optically pure materials and synthetic reactions which do not cause racemization or inversion of stereochemistry at the chiral centers.

Mixtures of stereoisomers of compounds, including racemic mixtures, resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography or crystallization/re-crystallization. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

Alternatively, salts of the enantiomers in the mixture can be prepared by any suitable method known in the art, including treatment of the carboxylic acid with a suitable optically pure base such as, but are not limited to, alkaloids and phenethylamine, followed by precipitation or crystallization/re-crystallization of the enantiomerically pure salts. Methods mentioned herein above and other useful methods for the resolution/separation of a mixture of stereoisomers, including racemic mixtures, may be found in "*Enantiomers, Racemates, and Resolutions,*" J. Jacques et al., 1981, John Wiley and Sons, New York, N.Y., the disclosure of which is incorporated herein by reference.

The compounds of this invention may possess one or more unsaturated carbon-carbon double bonds. All double bond isomers, both the cis (Z) and trans (E) isomers, and mixtures thereof are intended to be encompassed within the scoped of the present invention. Where a compound exists in various tautomeric forms, a recited compound is not limited to any one specific tautomer, but rather is intended to encompass all tautomeric forms.

Inhibition of Cytochrome P450

The ability of compounds to inhibit cytochrome P450 monooxygenase activity was tested with terfenadine as the probe substrate (Yun, et al., Drug Metabolism & Disposition, Vol. 21 403-407 (1993)). Compounds of formula I inhibited the terfenadine hydroxylase activity representing the most abundant form of cytochrome P450 (CYP3A4) present in human liver with an $IC_{50}$ range between about 0.05 µM and about 3.0 µM.

Pharmacokinetic Improvement

The ability of compounds of formula I, II, or III to improve the pharmacokinetics of a compound which is metabolized by cytochrome P450 monooxygenase can be demonstrated by the test method described below, wherein lopinavir is used as an example.

Lopinavir, either alone or in combination with a representative compound of the present invention was formulated at a concentration of 5 mg/mL each in a vehicle of 20% ethanol, 30% propylene glycol and D5W with appropriate molar equivalents of methanesulfonic acid to assist in solubilization. Beagle dogs (male and female; 8 to 12 kg; n=3) received 5 mg/kg body weight doses by oral gavage with and without an equal dose of the compound of the present invention. Plasma samples, obtained as a function of time after dosing (12 time points over 12 hours) were extracted into mixtures of ethyl acetate and hexane, concentrated, and analyzed by reversed-phase HPLC-MS (Kempf, et al., Antimicrob Agents Chemother, Vol. 41 654-660 (1997)). When dosed alone, lopinavir gave a maximum plasma level ($C_{max}$) and a plasma concentration curve (AUC) of 0. When lopinavir was dosed with compounds of the present invention, the $C_{max}$ values ranged from 0.95 mcg/mL to 5.07 mcg/mL, and the AUC values ranged from 3.09 mcg·hr/mL to 22.95 mcg·hr/mL. The corresponding time to maximum plasma level ($T_{max}$) of lopinavir was from 1.3 hours to 3.2 hours.

Abbreviations

Abbreviations which have been used in the descriptions of the Schemes and the Examples that follow are: AcOH for acetic acid; atm for atmospheres; Boc for tert-butoxycarbonyl; CDI for 1,1'-carbonyldiimidazole; DCE for 1,2-dichloroethane; DEAD for diethyl azodicarboxylate; DMF for N,N-dimethylformamide, DMSO for dimethylsulfoxide; EtOAc for ethyl acetate; EtOH for ethanol; IPA for isopropyl alcohol; MeOH for methanol; MsCl for methanesulfonyl chloride; TFA for trifluoroacetic acid; THF for tetrahydrofuran; and TLC for thin layer chromatography.

Preparation of Compounds of the Present Invention

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups $R_1$, $R_4$, and $R_5$, are as defined above unless otherwise noted below.

This invention is intended to encompass compounds having formula I, II or III when prepared by synthetic processes or by metabolic processes. Preparation of the compounds of the invention by metabolic processes include those occurring in the human or animal body (in vivo) or processes occurring in vitro.

If a substituent described herein is not compatible with the synthetic methods of this invention, the substituent may be protected with a suitable protecting group that is stable to the reaction conditions used in these methods. The protecting group may be removed at suitable point in the reaction sequence of the method to provide a desired intermediate or target compound. Suitable protecting groups and the methods for protecting and deprotecting different substituents using such suitable protecting groups are well know to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety.

Scheme 1

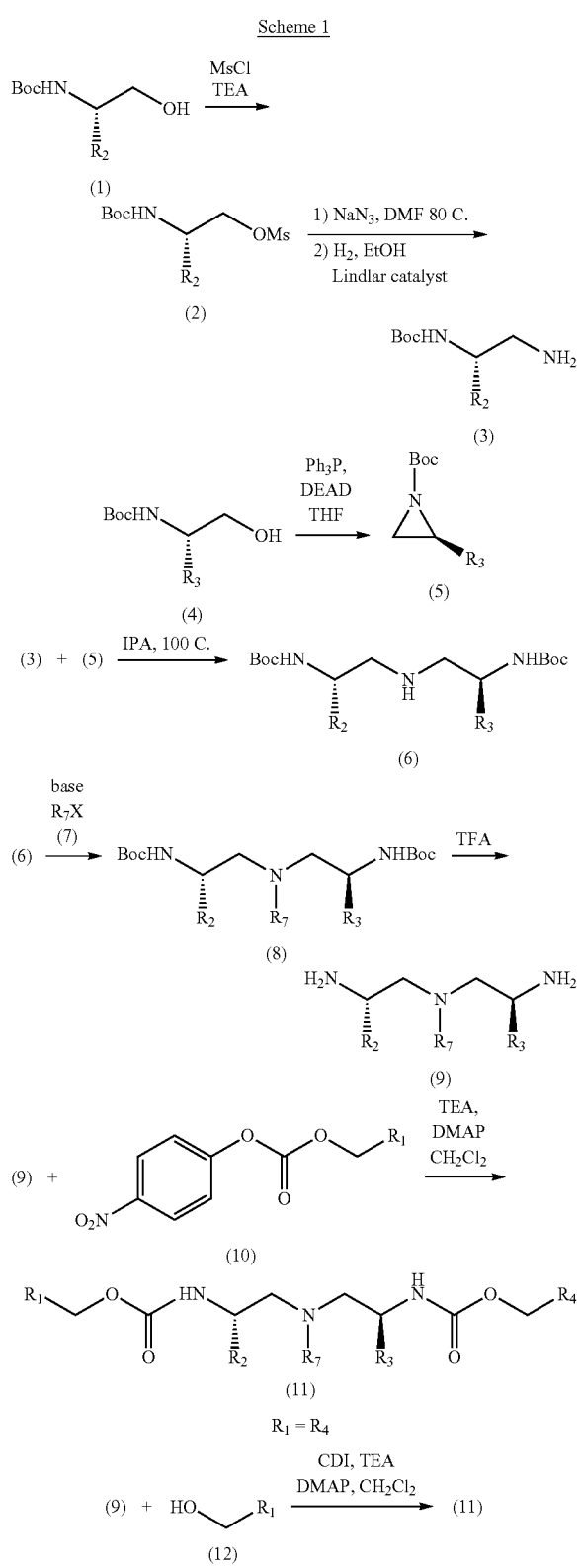

base such as triethylamine to provide sulfonates of general formula (2). Sulfonates of general formula (2) can be treated with sodium azide in DMF at a temperature of about 80° C. to provide the azide which can then be treated with a palladium catalyst under a hydrogen atmosphere in a solvent such as ethanol to provide amines of general formula (3). Alcohols of general formula (4) can be treated with a phosphine such as triphenylphosphine, tributylphosphine and an azo reagent such as diethyl azodicarboxylate or di-tert-butyl azodicarboxylate or diisopropyl azodicarboxylate to provide aziridines of general formula (5). Amines of general formula (3) can be treated with aziridines of general formula (5) in a solvent such as isopropyl alcohol at a temperature of about 100° C. to provide triamines of general formula (6). Triamines of general formula (6) can be treated with a base such as triethylamine and an electrophile of general formula (7), wherein X is Cl, Br or I, to provide triamines of general formula (8). Triamines of general formula (7) can also be treated with aldehydes or ketones in the presence of a reducing agent such as sodium cyanoborohydride, sodium triacetoxyborohydride or sodium borohydride to provide triamines of general formula (8). Triamines of general formula (8) can be treated with TFA or HCl such as 4N HCl in 1,4-dioxane or concentrated HCl in ethyl acetate to provide triamines of general formula (9). Triamines of general formula (9) can be treated with carbonates of general formula (10) and a base such as triethylamine to provide compounds of general formula (11). Alternatively, triamines of general formula (9) can be treated with alcohols of general formula (12), CU and a base such as triethylamine to provide compounds of general formula (11).

Scheme 2

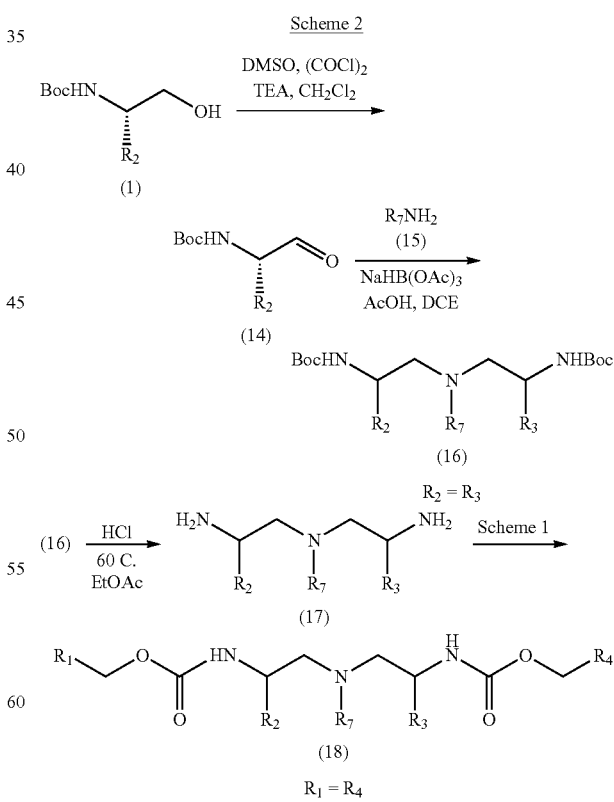

Compounds of general formula (11), wherein $R_1$, $R_2$, $R_3$, $R_4$ and $R_7$ are as defined in formula I and $R_1=R_4$, can be prepared as described in Scheme 1. Alcohols of general formula (1) can be treated with a sulfonyl chloride such as methanesulfonyl chloride or p-toluenesulfonyl chloride and a Compounds of general formula (18), wherein $R_1$, $R_2$, $R_3$, $R_4$ and $R_7$ are as defined in formula I and $R_1=R_4$ and $R_2=R_3$, can be prepared as described in Scheme 2. Alcohols of general formula (1) can be oxidized using, for example, Swern conditions to provide aldehydes of general formula (14). Aldehydes of general formula (14) can be treated with 0.5 equivalents of an amine of general formula (15), wherein $R_7$ is alkenyl alkoxyalkyl, alkoxycarbonylalkyl, alkyl, alkylcarbonyloxyalkyl, alkynyl, arylalkyl, aryloxyalkyl, arylthioalkoxyalkyl, arylthioalkyl, cyanoalkyl, cycloalkyl, cycloalkylalkyl, di(alkoxycarbonyl)alkyl, heterocyclealkoxyalkyl, heterocyclealkyl, heterocycleoxyalkyl, heterocyclethioalkoxyalkyl or heterocyclethioalkyl in the presence of a acetic acid and a reducing agent such as sodium cyanoborohydride, sodium triacetoxyborohydride or sodium borohydride to provide triamines of general formula (16). Triamines of general formula (16) can be treated with TFA or HCl such as 4N HCl 1,4-dioxane or concentrated HCl in ethyl acetate to provide triamines of general formula (17). Triamines of general formula (17) can be processed as described in Scheme 1 to provide compounds of general formula (18).

Scheme 3

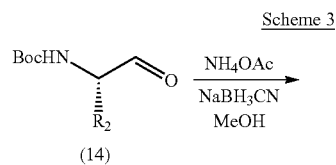

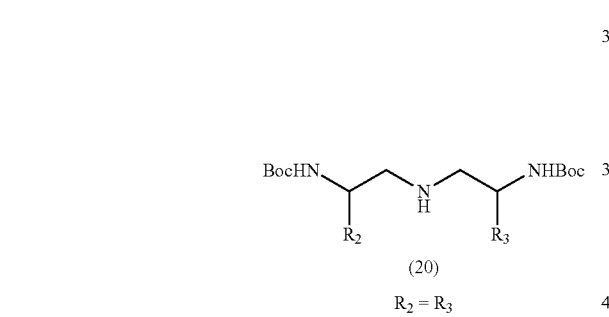

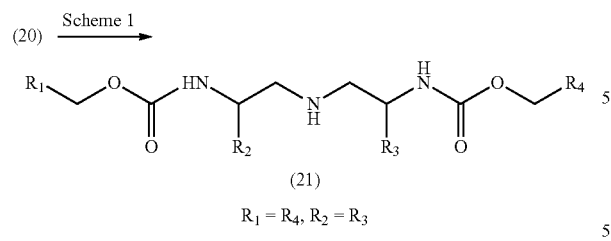

Compounds of general formula (21), wherein $R_1$, $R_2$, $R_3$ and $R_4$ are as defined in formula I and $R_1 = R_4$ and $R_2 = R_3$, can be prepared as described in Scheme 3. Aldehydes of general formula (14) can be treated with ammonium acetate and a reducing agent such as sodium cyanoborohydride, sodium triacetoxyborohydride or sodium borohydride in a solvent such as methanol to provide triamines of general formula (20). Triamines of general formula (20) can be processed as described in Scheme 1 to provide compounds of general formula (21).

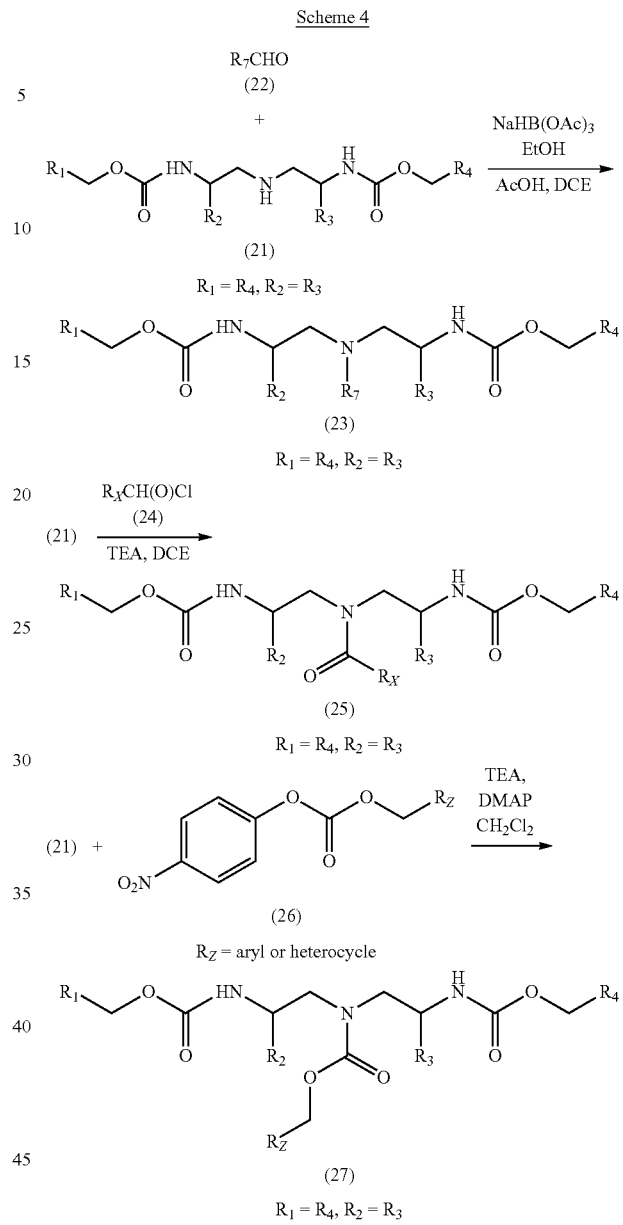

Compounds of general formula (23), wherein $R_1$, $R_2$, $R_3$, $R_4$ and $R_7$ are as defined in formula I and $R_1 = R_4$ and $R_2 = R_3$, can be prepared as described in Scheme 4. Compounds of general formula (21) can be treated with aldehydes of general formula (22), wherein $R_7$ is alkenyl alkoxyalkyl, alkoxycarbonylalkyl, alkyl, alkylcarbonyloxyalkyl, alkynyl, arylalkyl, aryloxyalkyl, arylthioalkoxyalkyl, arylthioalkyl, cyanoalkyl, cycloalkyl, cycloalkylalkyl, di(alkoxycarbonyl)alkyl, heterocyclealkoxyalkyl, heterocyclealkyl, heterocycleoxyalkyl, heterocyclethioalkoxyalkyl or heterocyclethioalkyl, and a reducing agent such as sodium cyanoborohydride, sodium triacetoxyborohydride or sodium borohydride in a solvent such as 1,2-dichloroethane to provide compounds of general formula (23).

Compounds of general formula (25), wherein $R_1$, $R_2$, $R_3$ and $R_4$ are as defined in formula I, Rx is alkenyl, alkoxy, alkyl, alkynyl, arylalkoxy, arylalkyl, aryl, heterocyclealkoxy, heterocycle or heterocyclealkyl, and $R_1 = R_4$ and $R_2 = R_3$, can be prepared as described in Scheme 4. Compounds of general formula (21) can be treated with chlorides of general formula (24) and a base such as triethylamine in a solvent such as 1,2-dichloroethane to provide compounds of general formula (25).

Compounds of general formula (27), wherein $R_1$, $R_2$, $R_3$ and $R_4$ are as defined in formula I, $R_Z$ is aryl or heterocycle, and $R_1$=$R_4$ and $R_2$=$R_3$, can be prepared as described in Scheme 4. Compounds of general formula (21) can be treated with carbonates of general formula (26) and a base such as triethylamine to provide compounds of general formula (27).

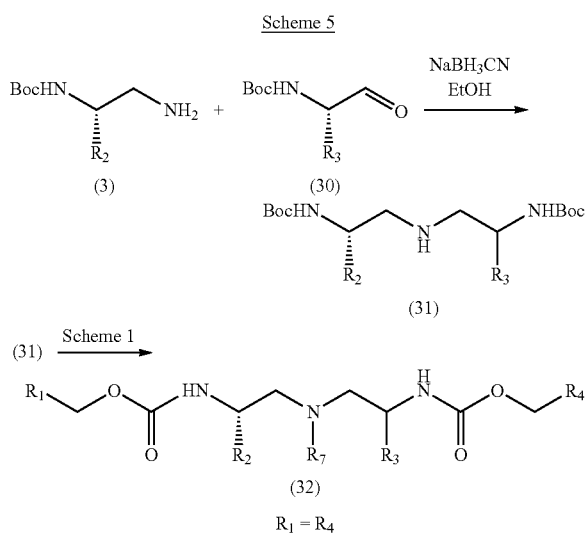

Compounds of general formula (32), wherein $R_1$, $R_2$, $R_3$, $R_4$ and $R_7$ are as defined in formula I and $R_1$=$R_4$, can be prepared as described in Scheme 5. Aldehydes of general formula (30) can be treated with amines of general formula (3) in the presence of a reducing agent such as sodium cyanoborohydride, sodium triacetoxyborohydride or sodium borohydride in a solvent such as ethanol to provide triamines of general formula (31). Triamines of general formula (31) can be processed as described in Scheme 1 to provide compounds of general formula (32).

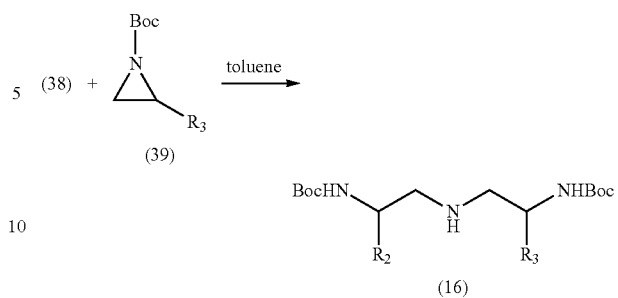

An alternative synthesis of compounds of general formula (18), wherein $R_1$, $R_2$, $R_3$, $R_4$ and $R_7$ are as defined in formula I and $R_1$=$R_4$, can be prepared as described in Scheme 6. Alcohols of general formula (35) can be treated with a phosphine such as triphenylphosphine, tributylphosphine and an azo reagent such as diethyl azodicarboxylate or di-tert-butyl azodicarboxylate or diisopropyl azodicarboxylate to provide aziridines of general formula (36). Aziridines of general formula (36) can be treated with benzylamine in a solvent such as toluene with heat to provide amines of general formula (37). Amines of general formula (37) can be treated with a palladium catalyst such as 20% palladium hydroxide on carbon under hydrogen at 4 atmospheres in a solvent such as methanol to provide amines of general formula (38). Amines of general formula (38) can be treated with aziridines of general formula (39) to provide triamines of general formula (16). Triamines of general formula (16) can be processed as described in Schemes 1 and 4 to provide compounds of general formula (18).

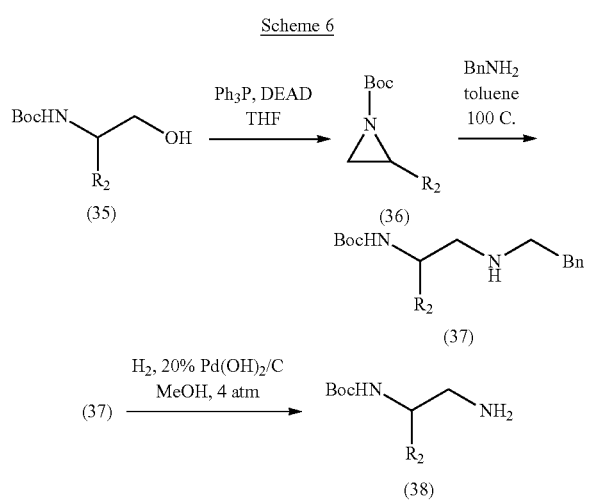

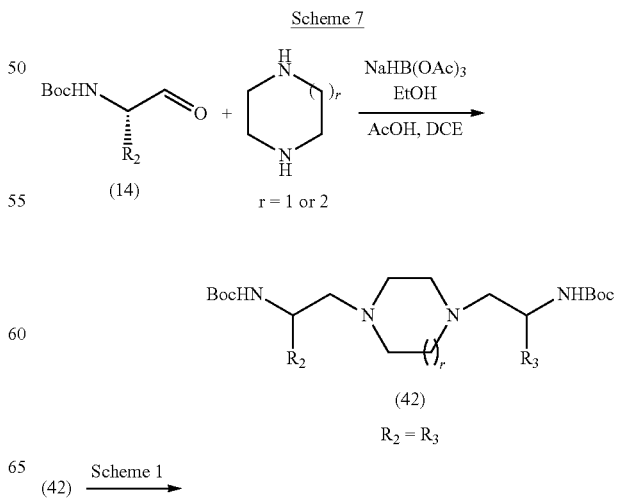

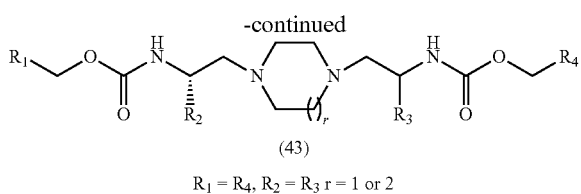

(43)

R₁ = R₄, R₂ = R₃ r = 1 or 2

Compounds of general formula (43), wherein $R_1$, $R_2$, $R_3$ and $R_4$ are as defined in formula I, $R_1$=$R_4$, $R_2$=$R_3$ and r is 1 or 2, can be prepared as described in Scheme 7. Aldehydes of general formula (14) can be treated with piperazine or hexahydro-1H-1,4-diazepine, acetic acid and a reducing agent such as sodium cyanoborohydride, sodium triacetoxyborohydride or sodium borohydride in a solvent such as 1,2-dichloroethane to provide piperazines or homopiperazines of general formula (42). Piperazines or homopiperazines of general formula (42) can be processed as described in Scheme 1 to provide compounds of general formula (43).

Scheme 8

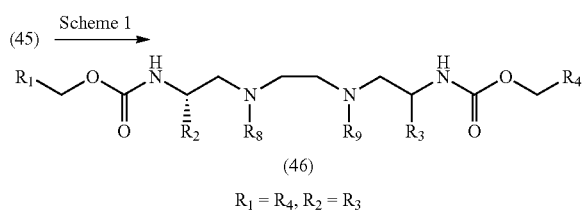

(46)

R₁ = R₄, R₂ = R₃

Compounds of general formula (46), wherein $R_1$, $R_2$, $R_3$, $R_4$, $R_8$ and $R_9$ are as defined in formula I, and $R_1$=$R_4$ and $R_2$=$R_3$, can be prepared as described in Scheme 8. Aldehydes of general formula (14) can be treated with diamines of general formula (44), acetic acid and a reducing agent such as sodium cyanoborohydride, sodium triacetoxyborohydride or sodium borohydride in a solvent such as 1,2-dichloroethane to provide tetraamines general formula (45). Tetraamines of general formula (45) can be processed as described in Scheme 1 to provide compounds of general formula (46).

Scheme 9

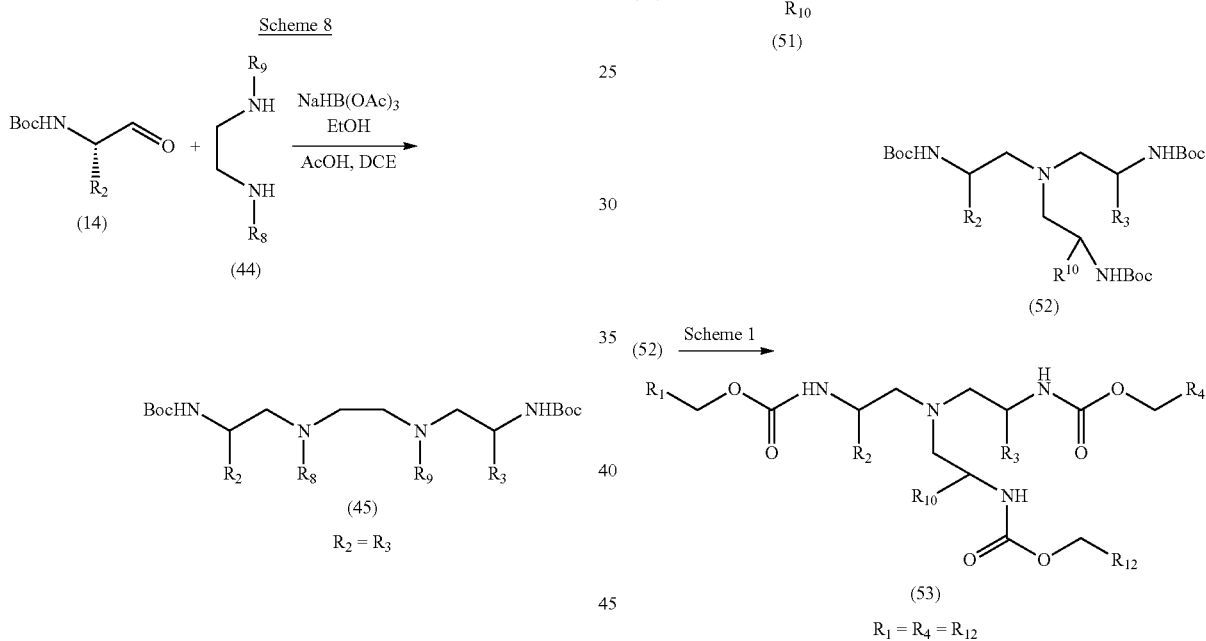

Compounds of general formula (53), wherein $R_1$, $R_2$, $R_3$, $R_4$, $R_{10}$ and $R_{12}$ are as defined in formula I and $R_1$=$R_4$=$R_{12}$, can be prepared as described in Scheme 9. Amines of general formula (48) and aldehydes of general formula (49) can be treated with acetic acid and a reducing agent such as sodium cyanoborohydride, sodium triacetoxyborohydride or sodium borohydride in a solvent such as 1,2-dichloroethanel to provide triamines of general formula (50). Triamines of general formula (50) can be treated with an aldehyde of general formula (51), acetic acid and a reducing agent such as sodium cyanoborohydride, sodium triacetoxyborohydride or sodium borohydride in a solvent such as 1,2-dichloroethanel to provide tetraamines of general formula (52). Tetraamines of general formula (52) can be processed as described in Scheme 1 to provide compounds of general formula (53).

The following Examples are intended as an illustration of and not a limitation upon the scope of the invention as defined in the appended claims.

Example 1

N-ethyl-N,N-bis[(2S)-2-(thiazol-5-ylmethoxycarbonylamino)-3-phenylpropyl]amine

Example 1A (2S)-2-[(tert-butoxycarbonyl)amino]-1-3-phenylpropyl methanesulfonate A solution of (2S)-2-(tert-butoxycarbonylamino)-3-phenyl-1-propanol (3.0 g, 11.9 mmol) in anhydrous $CH_2Cl_2$ (120 mL) at 0° C. under a dry $N_2$ atmosphere was treated with triethylamine (3.5 mL, 25.1 mmol) followed by dropwise addition of methanesulfonyl chloride (1.0 mL, 13.1 mmol). After stirring for 2 hours at 0° C., the solution was washed with brine (100 mL), dried over $Na_2SO_4$, filtered and concentrated to a reduced volume (20 mL). The mixture was diluted with hexanes (100 mL) and allowed to stand at ambient temperature overnight. Colorless crystals were collected by filtration and dried under reduced pressure to provide the title compound (3.60 g, 92%). $R_f$=0.26 (hexanes:ethyl acetate, 2:1); $^1$H NMR ($CDCl_3$) δ 7.36-7.18 (m, 5H), 4.71 (br s, 1H), 4.28-4.05 (m, 3H), 2.99-2.81 (m, 2H), 1.40 (s, 9H); MS (APCI+) m/z 254 (M+H)$^+$.

Example 1B (12S)-2-(tert-butoxycarbonylamino)-3-phenylpropylamine

The product from Example 1A (1.0 g, 3.0 mmol) in anhydrous DMF (10 mL) under a dry $N_2$ atmosphere was treated with sodium azide (0.9 g, 13.8 mmol). The suspension was stirred at 80° C. for 2 hours, allowed to cool to ambient temperature and was partitioned between water (50 mL) and ethyl acetate (2×50 mL). The organic layers were combined, dried over $Na_2SO_4$, filtered, and concentrated to provide an oil which was dissolved in ethanol (10 mL). The solution was treated with Lindlar's catalyst (0.2 g) and the resulting suspension was stirred under $H_2$ (1 atm) for 3 hours. The mixture was filtered through celite and concentrated to provide the title compound as an oil (0.62 g, 82%).

Example 1C (2S)—N-tert-butoxycarbonyl-2-phenylmethylaziridine (2S)-2-(tert-Butoxycarbonylamino)-3-phenyl-1-propanol (2.0 g, 8.0 mmol) in anhydrous THF (50 mL) at 0° C. under a dry $N_2$ atmosphere was treated with triphenylphosphine (2.5 g, 9.5 mmol) and diethyl azodicarboxylate (1.66 g, 9.5 mmol). The mixture was stirred at 0° C. for 1 hour, allowed to warm to ambient temperature and stirred overnight. The mixture was partitioned between water (50 mL) and ethyl acetate (2×50 mL). The organic layers were combined, dried over $Na_2SO_4$, filtered, and concentrated under reduced pressure. The residue was purified by column chromatography on silica gel (hexanes:$CH_2Cl_2$, 1:1) to provide the title compound as a colorless oil (1.4 g, 76%). $R_f$=0.54 (hexanes:ethyl acetate, 2:1); $^1$H NMR ($CDCl_3$) δ 7.32-7.19 (m, 5H), 3.01-2.90 (m, 1H), 2.70-2.56 (m, 2H), 2.30 (m, 1H), 2.03 (m, 1H), 1.44 (s, 9H).

Example 1D

N,N-bis[(2S)-2-(tert-butoxycarbonylamino)-3-phenylpropyl]amine

The product from Example 1B (0.54 g, 2.16 mmol) and the product from Example 1C (0.50 g, 2.14 mmol) in isopropanol (5 mL) were placed in a sealed tube and heated at 100° C. for 18 hours. The mixture was concentrated and the residue was purified by column chromatography on silica gel (24:1 $CHCl_3$:methanol) to provide the title compound as a colorless solid (0.44 g, 42%). $R_f$=0.55 ($CHCl_3$:methanol, 9:1); $^1$H NMR ($CDCl_3$) δ 7.30-7.14 (m, 10H), 4.61 (br s, 2H), 3.87 (m, 2H), 2.87-2.77 (m, 2H), 2.72 (dd, J=7.4, 13.6 Hz, 2H), 2.57 (d, J=5.8 Hz, 4H), 1.41 (s, 18H); MS (APCI+) m/z 484 (M+H)$^+$.

Example 1E

N,N-bis[(2S)-2-(tert-butoxycarbonylamino)-3-phenylpropyl]-N-ethylamine

The product from Example 1D (1.20 g, 2.5 mmol) in methanol (12 mL) was treated with sodium cyanoborohydride (0.25 g, 4.0 mmol), followed by acetaldehyde (0.30 mL, 5.4 mmol) and acetic acid (0.10 mL, 1.7 mmol). The mixture was stirred at ambient temperature for 3 hours and then concentrated under reduced pressure. The residue was partitioned between water (100 mL) and ethyl acetate (2×100 mL). The organic layers were combined, dried over $Na_2SO_4$, filtered, and concentrated under reduced pressure. The residue was purified by column chromatography on silica gel (hexanes:ethyl acetate, 2:1) to provide the title compound as a colorless solid (1.10 g, 87%). $R_f$=0.35 (hexanes:ethyl acetate, 1:1); $^1$H NMR ($CDCl_3$) δ 7.30-7.14 (m, 10H), 4.71 (br s, 2H), 3.84 (m, J=6.5, 7.3 Hz, 2H), 2.81 (d, J=6.4 Hz, 4H), 2.62-2.19 (m, 6H), 1.41 (s, 18H), 0.87 (t, J=7.1 Hz, 3H); MS (APCI+) m/z 512 (M+H)$^+$.

Example 1F

N-ethyl-N,N-bis[(2S)-2-(thiazol-5-ylmethoxycarbonylamino)-3-phenylpropyl]amine

The product from Example 1E (0.25 g, 0.49 mmol) in TFA:$CH_2Cl_2$ (1:2, 3 mL) was stirred at ambient temperature for 1.5 hours. The mixture was concentrated and the residue was dried under reduced pressure. The residue in anhydrous $CH_2Cl_2$ (5 mL) at 0° C. under a dry $N_2$ atmosphere was treated with triethylamine (0.5 mL, 3.6 mmol), 4-nitrophenyl 1,3-thiazol-5-ylmethyl carbonate hydrochloride (0.30 g, 1.11 mmol), and 4-dimethylaminopyridine (0.12 g, 0.98 mmol). The mixture was allowed to warm to ambient temperature and stirred for 3 hours. The reaction mixture was partitioned between ethyl acetate (20 mL) and saturated aqueous $NaHCO_3$ (3×20 mL). The organic layer was dried over $Na_2SO_4$, filtered, and concentrated under reduced pressure. The residue was purified by column chromatography on silica gel (hexanes:ethyl acetate, 1:2) to provide the title compound as a colorless solid (0.24 g, 83%). $R_f$=0.57 ($CHCl_3$:methanol, 9:1); $^1$H NMR ($CDCl_3$) δ 8.74 (s, 2H), 7.78 (s, 2H), 7.30-7.11 (m, 10H), 5.30-5.09 (m, 6H), 3.94 (m, 2H), 2.89-2.77 (m, 2H), 2.73 (dd, J=6.8, 13.6 Hz, 2H), 2.56-2.27 (m, 6H), 0.78 (t, J=7.1 Hz, 3H); MS (ESI+) m/z 594 (M+H)$^+$.

Example 2

N-ethyl-N,N-bis[(2S)-2-(oxazol-5-ylmethoxycarbonylamino)-3-phenylpropyl]amine

Example 2A oxazol-5-ylmethyl 1H-imidazole-1-carboxylate

Oxazol-5-ylmethanol (0.15 g, 1.51 mmol) in anhydrous $CH_2Cl_2$ (5 mL) under a dry $N_2$ atmosphere was treated with 1,1'-carbonyldiimidazole (0.20 g, 1.23 mmol) at ambient temperature and stirred for 2 hours to provide the title compound in a solution of $CH_2Cl_2$ which was used in subsequent Examples without further manipulation.

Example 2B

N-ethyl-N,N-bis[(2S)-2-(oxazol-5-ylmethoxycarbonylamino)-3-phenylpropyl]amine

The product from Example 1E (0.25 g, 0.49 mmol) in $TFA:CH_2Cl_2$ (1:2, 3 mL) was stirred at ambient temperature for 2 hours, concentrated and dried under reduced pressure. The residue in 1 mL $CH_2Cl_2$ (1 mL) at 0° C. under a dry $N_2$ atmosphere was treated with the product from Example 2A (5 mL), triethylamine (0.35 mL, 2.5 mmol), and N,N-dimethylaminopyridine (0.12 g, 1.0 mmol). The mixture was stirred at ambient temperature overnight and then partitioned between water (10 mL) and $CH_2Cl_2$ (3×10 mL). The organic layers were combined, dried over $Na_2SO_4$, filtered, and the filtrate was concentrated under reduced pressure. The residue was purified by column chromatography on silica gel ($CH_2Cl_2$:isopropanol, 9:1) to provide the title compound as a colorless solid (0.23 g, 84%). $R_f$=0.57 ($CHCl_3$:methanol, 9:1); $^1H$ NMR ($CDCl_3$) δ 7.79 (s, 2H), 7.31-7.11 (m, 10H), 7.05 (s, 2H), 5.21 (br. s, 2H), 5.09 (d, J=13.6 Hz, 2H), 5.01 (d, J=13.6 Hz, 2H), 3.94 (m, 2H), 2.90-2.80 (m, 2H), 2.72 (dd, J=7.0, 13.7 Hz, 2H), 2.55-2.26 (m, 6H), 0.77 (t, J=7.1 Hz, 3H); MS (ESI+) m/z 562 (M+H)+.

Example 3

N-ethyl-N,N-bis[(2S)-2-(thien-2-ylmethoxycarbonylamino)-3-phenylpropyl]amine

2-Thienylmethanol was processed as described in Examples 2A and 2B. The residue was purified by column chromatography on silica gel ($CHCl_3$) to provide the title compound as a colorless amorphous solid. $R_f$=0.38 (hexanes:ethyl acetate, 1:1); $^1H$ NMR ($CDCl_3$) δ 7.29-7.11 (m, 12H), 6.99-6.89 (m, 4H), 5.76-5.06 (m, 6H), 3.94 (m, 2H), 2.90-2.79 (m, 2H), 2.72 (dd, J=7.1, 13.9 Hz, 2H), 2.56-2.27 (m, 6H), 0.77 (t, J=7.1 Hz, 3H); MS (ESI+) m/z 592 (M+H)+.

Example 4

N-ethyl-N,N-bis[(2S)-2-(pyridin-3-ylmethoxycarbonylamino)-3-phenylpropyl]amine

3-Pyridinylmethanol was processed as described in Examples 2A and 2B. The residue was purified by column chromatography on silica gel ($CHCl_3$:methanol, 19:1) to provide the title compound as a colorless amorphous solid. $R_f$=0.21 ($CHCl_3$:methanol, 9:1); $^1H$ NMR ($CDCl_3$) δ 8.52-8.45 (m, 4H), 7.50 (d, J=7.8 Hz, 2H), 7.30-7.10 (m, 12H), 5.24 (br s, 2H), 5.04 (d, J=12.6 Hz, 2H), 4.94 (d, J=12.6 Hz, 2H), 3.96 (m, 2H), 2.89-2.78 (m, 2H), 2.74 (dd, J=6.8, 13.6 Hz, 2H), 2.59-2.28 (m, 6H), 0.80 (t, J=6.8 Hz, 3H); MS (ESI+) m/z 582 (M+H)+.

Example 5

N-ethyl-N,N-bis[(2S)-2-(1H-imidazol-4-ylmethoxycarbonylamino)-3-phenylpropyl]amine

Example 5A

N-ethyl-N,N-bis[(2S)-2-(1[(4-methylphenyl)sulfonyl]-1H-imidazol-4-ylmethoxycarbonylamino)-3-phenylpropyl]amine (1-[(4-Methylphenyl)sulfonyl]-1H-imidazol-4-yl)methanol was processed as described in Examples 2A and 2B. The residue was purified by column chromatography on silica gel ($CHCl_3$:methanol, 49:1) to provide the title compound as a colorless solid. $R_f$=0.45 ($CHCl_3$:methanol, 19:1); $^1H$ NMR ($CDCl_3$) δ 7.89 (d, J=1.0 Hz, 2H), 7.79 (m, J=1.7, 2.0, 8.5 Hz, 4H), 7.42-7.11 (m, 16H), 5.22 (br s, 2H), 4.93 (d, J=13.2 Hz, 2H), 4.89 (d, J=13.2 Hz, 2H), 3.92 (m, 2H), 2.81 (dd, J=5.4, 13.6 Hz, 2H), 2.69 (dd, J=6.8, 13.9 Hz, 2H), 2.41 (s, 6H), 2.40-2.25 (m, 6H), 0.70 (t, J=6.9 Hz, 3H); MS (ESI+) m/z 868 (M+H)+.

Example 5B

N-ethyl-N,N-bis[(2S)-2-(1H-imidazol-4-ylmethoxycarbonylamino)-3-phenylpropyl]amine The product from Example 5A (0.12 g, 0.14 mmol) and 1-hydroxybenzotriazole (50 mg, 0.37 mmol) in THF (2 mL) were stirred at ambient temperature for 3 days. The solvent was removed under reduced pressure and the residue was purified by column chromatography on silica gel ($CHCl_3$:methanol:$NH_4OH$, 90:10:1) to provide the title compound as a colorless solid (36 mg, 47%). $R_f$=0.10 ($CHCl_3$:methanol:$NH_4OH$, 90:10:1); $^1H$ NMR ($CDCl_3$) δ 7.59 (s, 2H), 7.29-7.10 (m, 10H), 7.07 (s, 2H), 5.32-5.06 (m, 4H), 4.99-4.90 (m, 2H), 3.94 (m, 2H), 2.87-2.78 (m, 2H), 2.67 (dd, J=7.1, 13.6 Hz, 2H), 2.45-2.15 (m, 6H), 0.64 (t, J=6.8 Hz, 3H); MS (ESI+) m/z 560 (M+H)+.

Example 6

N-ethyl-N,N-bis[(2S)-2-(pyrazol-5-ylmethoxycarbonylamino)-3-phenylpropyl]amine

Example 6A

N-ethyl-N,N-bis[(2S)-2-(propyn-2-yloxycarbonylamino)-3-phenylpropyl]amine

Propargyl alcohol was processed as described in Examples 2A and 2B. The residue was purified by column chromatography on silica gel (hexanes:ethyl acetate, 1:1) to provide the title compound as a colorless solid. $R_f$=0.42 (hexanes:ethyl acetate, 1:1); $^1H$ NMR ($CDCl_3$) δ 7.32-7.13 (m, 10H), 5.23 (br s, 2H), 4.70 (s, 2H), 4.69 (s, 2H), 3.94 (m, 2H), 2.87 (dd, J=5.9, 13.7 Hz, 2H), 2.72 (dd, J=7.1, 13.9 Hz, 2H), 2.57-2.27 (m, 8H), 0.79 (t, J=7.1 Hz, 3H); MS (ESI+) m/z 476 (M+H)$^+$.

Example 6B

N-ethyl-N,N-bis[(2S)-2-(pyrazol-5-ylmethoxycarbonylamino)-3-phenylpropyl]amine

The product from Example 6A (0.12 g, 0.25 mmol) in diethyl ether was treated with a solution of diazomethane in diethyl ether (~0.4 M, 3 mL) and stirred at ambient temperature under a N$_2$ atmosphere for 3 days, during which time the yellow color slowly dissipated. The solvent was removed under reduced pressure and the residue was subjected to column chromatography on silica gel (CHCl$_3$:methanol:NH$_4$OH, 90:10:1). The material was then subjected to HPLC (RP-18, 30-70% CH$_3$CN in 0.1% aqueous TFA) to provide the title compound as a colorless solid (14 mg, 10%). R$_f$=0.28 (CHCl$_3$:methanol:NH$_4$OH, 90:10:1); $^1$H NMR (CDCl$_3$) δ 7.51 (d, J=1.0 Hz, 2H), 7.30-7.09 (m, 10H), 6.29 (d, J=1.6 Hz, 2H), 5.40-4.90 (m, 6H), 3.94 (m, 2H), 2.92-2.80 (m, 2H), 2.74-2.65 (m, 2H), 2.48-2.23 (m, 6H), 0.67 (m, 3H); MS (ESI+) m/z 560 (M+H)$^+$.

Example 7

N-(2,2-dimethylpropyl)-N,N-bis[(2S)-2-(thiazol-5-ylmethoxycarbonylamino)-3-phenylpropyl]amine and N-(2,2-dimethylpropyl)-N,N-bis[(2R)-2-(thiazol-5-ylmethoxycarbonylamino)-3-phenylpropyl]amine

Example 7A (2S)-2-(tert-butoxycarbonylamino)-3-phenyl-1-propanal

Oxalyl chloride in anhydrous CH$_2$Cl$_2$ (2.0M, 6.0 mL, 12.0 mmol) was treated with dimethylsulfoxide (1.0 mL, 14.1 mmol) in anhydrous CH$_2$Cl$_2$ (3 mL) dropwise over 5 minutes at −78° C. under a dry N$_2$ atmosphere. The mixture was stirred at −78° C. for 15 minutes and then treated with (2S)-2-(tert-butoxycarbonylamino)-3-phenyl-1-propanol (2.0 g, 8.0 mmol) in anhydrous CH$_2$Cl$_2$ (6 mL) dropwise over 10 minutes. The mixture was stirred at −78° C. for 30 minutes and then treated with triethylamine (4.4 mL, 31.7 mmol) in anhydrous CH$_2$Cl$_2$ (6 mL) dropwise over 10 minutes. The mixture was allowed to slowly warm to ambient temperature, stirred for 1 hour, diluted with CH$_2$Cl$_2$ (100 mL), washed with 10% aqueous citric acid (50 mL), water (50 mL), saturated NaHCO$_3$ (50 mL), dried over Na$_2$SO$_4$, filtered, and the solvent removed under reduced pressure to provide the title compound as an off-white crystalline solid (2.0 g).

EMBED ChemDraw.Document.4.5

Example 7B

N,N-bis[2-(tert-butoxycarbonylamino)-3-phenylpropyl]-N-(2,2-dimethylpropyl)amine The product from Example 7A (2.0 g, 8.0 mmol) in dichloroethane (40 mL) was treated with 2,2-dimethylpropylamine (0.47 mL, 4.0 mmol). The mixture was stirred for 20 minutes and then treated with acetic acid (0.23 mL, 4.0 mmol) and sodium triacetoxyborohydride (0.85 g, 4.0 mmol). The mixture was stirred for 90 minutes and more acetic acid (0.32 mL, 5.6 mmol) and sodium triacetoxyborohydride (1.19 g, 5.6 mmol) were added and stirring was continued overnight. The mixture was poured into saturated NaHCO$_3$ (100 mL) and extracted with ethyl acetate (2×100 mL). The organic layers were combined, dried over Na$_2$SO$_4$, filtered, and concentrated under reduced pressure. The residue was purified by column chromatography on silica gel (CH$_2$Cl$_2$:methanol, 39:1) to provide the title compound as a colorless solid (1.20 g). A portion of this material was repurified by column chromatography on silica gel (hexanes:ethyl acetate, 9:1) to provide the title compound as a colorless solid. R$_f$=0.32 (hexanes:ethyl acetate, 4:1); $^1$H NMR (CDCl$_3$) δ 7.28-7.10 (m, 10H), 5.02 (br s, 1H), 4.56 (br s, 1H), 3.85-3.72 (m, 2H), 2.95-2.64 (m, 4H), 2.47-1.88 (m, 6H), 1.42 (s, 9H), 1.36 (s, 9H), 0.84 (s, 4.5H), 0.80 (s, 4.5H); MS (ESI+) m/z 554 (M+H)$^+$.

EMBED ChemDraw.Document.4.5

Example 7C

N,N-bis[2-amino-3-phenylpropyl]-N-(2,2-dimethylpropyl)amine

The product from Example 7B (0.50 g, 0.90 mmol) in ethyl acetate (15 mL) was treated with concentrated HCl (0.6 mL) and refluxed for 30 minutes. The cooled mixture was concentrated under reduced pressure to provide a light tan solid, which was dissolved in 5 mL water and vigorously stirred while a solution of 0.25 M K$_2$CO$_3$ (7 mL) was added dropwise. The mixture was extracted with ethyl acetate (3×20 mL), and the organic layers were combined, washed with water (50 mL) and brine, dried over Na$_2$SO$_4$, filtered, and concentrated under reduced pressure to provide the title compound as a colorless gum (0.34 g).

Example 7D

N-(2,2-dimethylpropyl)-N,N-bis[(2S)-2-(thiazol-5-ylmethoxycarbonylamino)-3-phenylpropyl]amine and N-(2,2-dimethylpropyl)-N,N-bis[(2R)-2-(thiazol-5-ylmethoxycarbonylamino)-3-phenylpropyl]amine The product from Example 7C (0.34 g) was treated with 4-nitrophenyl 1,3-thiazol-5-ylmethyl carbonate [prepared from 4-nitrophenyl 1,3-thiazol-5-ylmethyl carbonate hydrochloride salt (0.63 g, 1.99 mmol) by extraction with aqueous NaHCO$_3$] in ethyl acetate (10 mL). The mixture was stirred at 60° C. under a N$_2$ atmosphere overnight. The mixture was diluted with ethyl acetate (50 mL), extracted with 10% aqueous K$_2$CO$_3$ (3×20 mL), washed with water (20 mL) and brine, dried over Na$_2$SO$_4$, filtered, and concentrated under reduced pressure. The residue was subjected to column chromatography on silica gel (ethyl acetate:hexanes, 2:1) to provide the two title compounds combined and a third separated product. The mixture of (S,S) and (R,R) enantiomers were obtained as a colorless amorphous solid. R$_f$=0.32 (ethyl acetate); $^1$H NMR (CDCl$_3$) δ 8.73 (s, 2H), 7.75 (s, 2H), 7.30-7.11 (m, 10H), 5.53 (br s, 2H), 5.23 (d, J=12.9 Hz, 2H), 5.16 (d, J=13.2 Hz, 2H), 3.91 (m, 2H), 2.90-2.79 (m, 2H), 2.68 (dd, J=7.5, 13.6 Hz, 2H), 2.42 (t, J=12 Hz, 2H), 2.26 (dd, J=1, 12 Hz, 2H), 1.99 (d, J=13.9 Hz, 1H), 1.87 (d, J=14.2 Hz, 1H), 0.71 (s, 9H); MS (ESI+) m/z 636 (M+H)$^+$.

Example 8

N-(2,2-dimethylpropyl)-N-[(2R)-2-(thiazol-5-yl-methoxycarbonylamino)-3-phenylpropyl]-N-[(2S)-2-(thiazol-5-ylmethoxycarbonylamino)-3-phenylpropyl]amine The title compound was obtained from the flash chromatography described in Example 7D as a colorless amorphous solid. $R_f$=0.41 (ethyl acetate); $^1$H NMR (CDCl$_3$) δ 8.72 (s, 2H), 7.79 (s, 2H), 7.28-7.04 (m, 10H), 5.20 (s, 4H), 4.80 (br s, 2H), 3.85 (m, 2H), 2.87 (dd, J=6.1, 13.9 Hz, 2H), 2.73-2.62 (m, 2H), 2.47 (d, J=7.1 Hz, 4H), 2.17 (s, 2H), 0.78 (s, 9H); MS (ESI+) m/z 636 (M+H)$^+$.

Example 9

N,N-bis[2-(thiazol-5-ylmethoxycarbonylamino)-3-phenylpropyl]amine

Example 9A

N,N-bis[2-(tert-butoxycarbonylamino)-3-phenylpropyl]amine

The product from Example 7A (3.0 g, 11.9 mmol)] in methanol (100 mL) was treated with ammonium acetate (0.47 g, 6.1 mmol) and sodium cyanoborohydride (1.13 g, 18.0 mmol). The mixture was stirred at ambient temperature overnight and then concentrated under reduced pressure. The residue was partitioned between water (50 mL) and CHCl$_3$ (3×50 mL). The organic layers were combined, dried over Na$_2$SO$_4$, filtered and concentrated under reduced pressure. The residue was purified by column chromatography on silica gel (ethyl acetate:hexanes, 4:1) to provide the title compound as a colorless solid (0.56 g, 19%). $R_f$=0.55 (CHCl$_3$:methanol, 9:1); $^1$H NMR (CDCl$_3$) δ 7.32-7.14 (m, 10H), 4.73-4.58 (2 br s, 2H), 3.88 (m, 2H), 2.89-2.77 (m, 2H), 2.77-2.67 (m, 2H), 2.64-2.48 (m, 4H), 1.41 (2 s, 18H).

Example 9B

N,N-bis[2-(thiazol-5-ylmethoxycarbonylamino)-3-phenylpropyl]amine

The product from Example 9A (0.20 g, 0.41 mmol) was processed as described in Example 1F except that the acylation step was stirred for 3 hours at 0° C. The residue was purified by column chromatography on silica gel (CHCl$_3$:methanol, 19:1) to provide the title compound as a colorless crystalline solid (0.20 g, 85%). $R_f$=0.33 (CHCl$_3$:methanol, 9:1); $^1$H NMR (CDCl$_3$) δ 8.77 (2s, 2H), 7.84 (s, 1H), 7.82 (s, 1H), 7.29-7.08 (m, 10H), 5.31-5.17 (m, 4H), 4.93 (br s, 2H), 3.93 (m, 2H), 2.88-2.66 (m, 4H), 2.65-2.52 (m, 4H); MS (ESI+) m/z 566 (M+H)$^+$.

Example 10

N-ethyl-N,N-bis[(2S)-2-(thiazol-5-ylmethoxycarbonylamino)-4-methylpentyl]amine (2S)-2-(tert-butoxycarbonylamino)-4-methyl-1-pentanol was processed as described in Examples 1A-1F. The residue was purified by column chromatography on silica gel (CH$_2$Cl$_2$:methanol, 49:1) to provide the title compound. $^1$H NMR (CDCl$_3$) δ 8.75 (s, 2H), 7.80 (s, 2H), 5.32-4.90 (m, 6H), 3.76 (m, 2H), 2.56-2.26 (m, 6H), 1.72-1.60 (m, 2H), 1.30-1.19 (m, 4H), 0.91 (d, J=6.5 Hz, 12H), 0.88 (t, J=7.1 Hz, 3H); MS (APCI+) m/z 526 (M+H)$^+$.

Example 11

N-ethyl-N,N-bis[(2S)-2-(thiazol-5-ylmethoxycarbonylamino)propyl]amine hydrochloride (2S)-2-(tert-Butoxycarbonylamino)-1-propanol was processed as described in Examples 1A-1F. The residue was purified by column chromatography on silica gel (49:1 CH$_2$Cl$_2$:methanol) to provide the title compound as the free base. The free base (60 mg, 0.136 mmol) in ethyl acetate (1 mL) was treated with 1N HCl in diethyl ether (0.136 mL) and the resulting precipitate was collected by filtration and dried under reduced pressure to provide the hydrochloride salt as a colorless solid. $^1$H NMR (DMSO-d$_6$) δ 9.10 (s, 2H), 7.95 (br s, 2H), 7.61 (d, J=7.8 Hz, 1H), 7.49 (d, J=8.1 Hz, 1H), 5.35-5.22 (m, 4H), 3.98 (m, 2H), 3.29-3.00 (m, 6H), 1.30-1.07 (m, 9H); MS (APCI+) m/z 442 (M+H)$^+$.

Example 12

N-ethyl-N,N-bis[(2R)-2-(thiazol-5-ylmethoxycarbonylamino)propyl]amine hydrochloride (2R)-2-(tert-Butoxycarbonylamino)-1-propanol was processed as described in Examples 1A-1F. The residue was purified by column chromatography on silica gel (CH$_2$Cl$_2$:methanol, 49:1) to provide the title compound as the free base. The free base was treated with 1N HCl in diethyl ether as described in Example 11 to provide the hydrochloride salt as a colorless solid. $^1$H NMR (CDCl$_3$) δ 8.81 (br s, 2H), 7.90 (br s, 2H), 6.65 (br d, 1H), 6.03 (br d, 1H), 5.40-5.25 (m, 4H), 4.13 (m, 2H), 3.52-3.15 (m, 4H), 3.05-2.83 (m, 2H), 1.36-1.22 (m, 9H); MS (APCI+) m/z 442 (M+H)$^+$.

Example 13

N-ethyl-N-[(2R)-2-(thiazol-5-ylmethoxycarbonylamino)propyl]-N-[(2S)-2-(thiazol-5-ylmethoxycarbonylamino)propyl]amine hydrochloride EMBED ChemDraw.Document 4.5

Example 13A (2R)—N-tert-butoxycarbonyl-2-methyl-aziridine (2R)-2-(tert-Butoxycarbonylamino)-1-propanol was processed as described in Example 1C to provide the title compound.

EMBED ChemDraw.Document.4.5

Example 13B (S)-2-(tert-butoxycarbonylamino)propylamine (2S)-2-(tert-Butoxycarbonylamino)-1-propanol was processed as described in Examples 1A and 1B to provide the title compound.

Example 13C

N-ethyl-N-[(2S)-2-(thiazol-5-ylmethoxycarbonylamino)propyl]-N-[(2R)-2-(thiazol-5-ylmethoxycarbonylamino)propyl]amine hydrochloride The product from Example 13A and the product from Example 13B were processed as described in Examples 1D-1F. The residue was purified by column chromatography on silica gel (CH$_2$Cl$_2$:methanol, 49:1) to provide the free base of the title compound. The free base was treated with 1N HCl in diethyl ether as described in Example 11 to provide the title compound as a colorless solid. $^1$H NMR (DMSO-d$_6$) δ 9.10 (s, 2H), 7.95 (br s, 2H), 7.58 (br d, 2H), 5.38-5.22 (m, 4H), 3.99 (m, 2H), 3.25-3.00 (m, 6H), 1.30-1.05 (m, 9H); MS (APCI+) m/z 442 (M+H)$^+$.

Example 14

N-ethyl-N,N-bis[2-(thiazol-5-ylmethoxycarbonylamino)ethyl]amine hydrochloride

Example 14A 2-(tert-butoxycarbonylamino)acetaldehyde 2-(tert-Butoxycarbonylamino)ethanol was processed as described in Example 7A to provide the title compound.

Example 14B

N-ethyl-N,N-bis[2-(tert-butoxycarbonylamino)ethyl]amine

The product from Example 14A and ethylamine were processed as described in Example 7B to provide the title compound.

Example 14C

N-ethyl-N,N-bis[2-(thiazol-5-ylmethoxycarbonylamino)ethyl]amine hydrochloride

The product from Example 14B was processed as described in Examples 7C and 7D. The residue was purified by column chromatography on silica gel (CH$_2$Cl$_2$:methanol, 19:1) to provide the free base of the title compound. The free base was treated with 1N HCl in diethyl ether as described in Example 11 to provide the title compound as a glass. $^1$H NMR (CD$_3$OD) δ 9.53 (br s, 2H), 8.18 (br s, 2H), 5.53-5.33 (m, 6H), 3.61-3.50 (m, 4H), 3.45-3.34 (m, 6H), 1.34 (t, J=7.3 Hz, 3H); MS (ESI+) m/z 414 (M+H)$^+$.

Example 15

N-ethyl-N,N-bis[2-(thiazol-5-ylmethoxycarbonylamino)-3-cyclohexylpropyl]amine

EMBED ChemDraw.Document.4.5

Example 15A (2S)-2-(tert-Butoxycarbonylamino)-3-cyclohexyl-1-propanal (2S)-2-(tert-Butoxycarbonyl)amino-3-cyclohexyl-1-propanol was processed as described in Example 7A to provide the title compound.

EMBED ChemDraw.Document.4.5

Example 15B

N-ethyl-N,N-bis[2-(tert-butoxycarbonylamino)-3-cyclohexylpropyl]amine

The product from Example 15A and ethylamine were processed as described in Example 7B to provide the title compound.

Example 15C

N-ethyl-N,N-bis[2-(thiazol-5-ylmethoxycarbonylamino)-3-cyclohexylpropyl]amine

The product from Example 15B was processed as described in Examples 7C and 7D. The residue was purified by column chromatography on silica gel (hexanes:ethyl acetate, 2:1) to provide the title compound as a colorless amorphous solid: $^1$H NMR (CDCl$_3$) δ 8.76 (s, 2H), 7.81 (s, 2H), 5.36-4.92 (m, 6H), 3.75 (m, 2H), 2.62-2.25 (m, 6H), 1.80-1.50 (m, 10H), 1.40-1.10 (m, 12H), 1.05-0.78 (m, 7H); MS (ESI+) m/z 606 (M+H)$^+$.

Example 16

N-ethyl-N,N-bis[2-(thiazol-5-ylmethoxycarbonylamino)-3-(methoxycarbonyl)propyl]amine EMBED ChemDraw.Document.4.5

Example 16A methyl (S)-3-(tert-butoxycarbonylamino)-4-oxobutanoate

Methyl (S)-3-(tert-butoxycarbonylamino)-4-hydroxy-butanoate was processed as described in Example 7A to provide the title compound.

Example 16B

N-ethyl-N,N-bis[2-(tert-butoxycarbonylamino)-3-(methoxycarbonyl)propyl]amine

The product from Example 16A and ethylamine were processed as described in Example 7B to provide the title compound.

Example 16C

N-ethyl-N,N-bis[2-(thiazol-5-ylmethoxycarbonylamino)-3-(methoxycarbonyl)propyl]amine The product from Example 16B was processed as described in Examples 7C and 7D. The residue was purified by column chromatography on silica gel (CH$_2$Cl$_2$:methanol, 49:1) to provide the title compound as a colorless amorphous solid. $^1$H NMR (CDCl$_3$) δ 8.79 (s, 0.65H), 8.76 (s, 1.35H), 7.86 (s, 1.35H), 7.82 (s, 0.65H), 5.67 (br s, 1H), 5.45-5.17 (m, 5H), 4.02 (m, 1.35H), 3.95 (m, 0.65H), 3.67 (s, 4H), 3.66 (s, 2H), 2.66-2.44 (m, 10H), 0.95-0.90 (m, 3H); MS (APCI+) m/z 558 (M+H)+.

EMBED ChemDraw.Document.4.5

Example 17

N-ethyl-N-[(2S)-2-(thiazol-5-ylmethoxycarbonylamino)-3-(phenylmethoxy)propyl]-N-[2-(thiazol-5-ylmethoxycarbonylamino)-3-(phenylmethoxy)propyl]amine

Example 17A (2S)-2-(tert-butoxycarbonylamino)-3-phenylmethoxypropanal (2S)-2-(tert-butoxycarbonylamino)-3-phenylmethoxy-1-propanol was processed as described in Example 7A to provide the title compound.

Example 17B (2S)-2-(tert-butoxycarbonylamino)-3-(phenylmethoxy)propylamine (2S)-2-(tert-butoxycarbonylamino)-3-phenylmethoxy-1-propanol was processed as described in Examples 1A and 1B to provide the title compound.

Example 17C

N-[(2S)-2-(tert-butoxycarbonylamino)-3-(phenylmethoxy)propyl]-N-[2-(tert-butoxycarbonylamino)-3-(phenylmethoxy)propyl]amine The product from Example 17B (0.35 g, 1.25 mmol) and the product from Example 17A (0.36 g, 1.29 mmol) in absolute ethanol (12 mL) were treated with sodium cyanoborohydride (94 mg, 1.50 mmol) and a catalytic amount of acetic acid. The resulting mixture was stirred at ambient temperature overnight. The mixture was partitioned between water (40 mL) and ethyl acetate (3×40 mL). The organic layers were combined, dried over Na$_2$SO$_4$, filtered, and concentrated under reduced pressure. The residue was subjected to column chromatography on silica gel (hexanes:ethyl acetate, 1:1) to provide the title compound (0.15 g, 22%).

Example 17D

N-[(2S)-2-(tert-butoxycarbonylamino)-3-(phenylmethoxy)propyl]-N-[2-(tert-butoxycarbonylamino)-3-(phenylmethoxy)propyl]-N-ethylamine The product from Example 17C (0.15 g) in dichloroethane (5 mL) was treated with acetaldehyde (20 µL, 0.36 mmol). After stirring at ambient temperature for 10 minutes, the mixture was treated with sodium triacetoxyborohydride (0.10 g, 0.47 mmol) and acetic acid (20 µL, 0.35 mmol). After stirring at ambient temperature overnight, the mixture was diluted with CH$_2$Cl$_2$ (20 mL), washed with saturated aqueous NaHCO$_3$ (2×20 mL) and brine, dried over Na$_2$SO$_4$, filtered, and concentrated under reduced pressure. The residue was purified by column chromatography on silica gel (hexanes: ethyl acetate, 1:1) to provide the title compound (75 mg, 44%). $^1$H NMR (CDCl$_3$) δ 7.36-7.24 (m, 10H), 4.93 (br s, 2H), 4.54-4.41 (m, 4H), 3.77-3.63 (m, 2H), 3.61 (dd, J=3.4, 9.2 Hz, 2H), 3.5-3.38 (m, 2H), 2.66-2.42 (m, 6H), 1.44 (s, 9H), 1.43 (s, 9H), 0.98 (t, J=7.1 Hz, 1.5H), 0.96 (t, J=7.1 Hz, 1.5H); MS (APCI+) m/z 572 (M+H)+.

Example 17E

N-ethyl-N-[(2S)-2-(thiazol-5-ylmethoxycarbonylamino)-3-(phenylmethoxy)propyl]-N-[2-(thiazol-5-ylmethoxycarbonylamino)-3-(phenylmethoxy)propyl]amine The product from Example 17D (67 mg, 0.12 mmol) in 1:1 TFA:CH$_2$Cl$_2$ (1 mL) was stirred at ambient temperature for 1 hour. The mixture was concentrated and the residue was dried under reduced pressure. The residue in ethyl acetate (2 mL) was treated with triethylamine (50 µL, 0.36 mmol), 4-nitrophenyl 1,3-thiazol-5-ylmethyl carbonate [prepared from 4-nitrophenyl 1,3-thiazol-5-ylmethyl carbonate hydrochloride salt (82 mg, 0.26 mmol) by extraction with aqueous NaHCO$_3$] in ethyl acetate (1 mL) and 4-dimethylaminopyridine (29 mg, 0.24 mmol). The resulting mixture was stirred at ambient temperature overnight, diluted with ethyl acetate (10 mL), extracted with saturated aqueous NaHCO$_3$ (3×10 mL), dried over Na$_2$SO$_4$, filtered, and concentrated under reduced pressure. The residue was purified by column chromatography on silica gel (ethyl acetate) to provide the title compound (35 mg, 46%). $^1$H NMR (CDCl$_3$) δ 8.76 (s, 2H), 7.84 (s, 1H), 7.82 (s, 1H), 7.34-7.26 (m, 10H), 5.45-5.15 (m, 6H), 4.50-4.40 (m, 4H), 3.78 (m, 2H), 3.58-3.53 (m, 2H), 3.47-3.39 (m, 2H), 2.59-2.47 (m, 6H), 0.96-0.88 (m, 3H); MS (APCI+) m/z 654 (M+H)+.

EMBED ChemDraw.Document.4.5

Example 18

N-ethyl-N-[(2S)-2-(thiazol-5-ylmethoxycarbonylamino)-3-[4-(phenylmethoxy)phenyl]propyl]-N-[2-(thiazol-5-ylmethoxycarbonylamino)-3-[4-(phenylmethoxy)phenyl]propyl]amine

Example 18A (2S)-2-(tert-butoxycarbonylamino)-3-[4-(phenylmethoxy)phenyl]propanal (2S)-2-(tert-Butoxycarbonylamino)-3-[4-(phenylmethoxy)phenyl]-1-propanol was processed as described in Example 7A to provide the title compound.

Example 18B (S)-2-(tert-butoxycarbonylamino)-3-[4-(phenylmethoxy)phenyl]propylamine and (S)-2-(tert-butoxycarbonylamino)-3-[4-(hydroxy)phenyl]propylamine (S)-2-(tert-Butoxycarbonylamino)-3-[4-(phenylmethoxy)phenyl]-1-propanol was processed as described in Examples 1A and 1B to provide the title products in approximately (1:1) ratio.

Example 18C

N-[(2S)-2-(tert-butoxycarbonylamino)-3-[4-(phenyl-methoxy)phenyl]propyl]-N-[2-(tert-butoxycarbony-lamino)-3-[4-(phenylmethoxy)phenyl]propyl]amine and N-[(2S)-2-(tert-butoxycarbonylamino)-3-[4-(hydroxy)phenyl]propyl]-N-[2-(tert-butoxycarbony-lamino)-3-[4-(phenylmethoxy)phenyl]propyl]amine The product from Example 18A (0.21 g), the mixture of products from Example 18B (0.19 g), sodium cyanoborohydride (0.18 g) and a catalytic amount of acetic acid (36 μL) in 1,2-dichloroethane (5 mL) were processed as described in Example 17C. The residue was purified by column chromatography on silica gel ($CH_2Cl_2$ to 1% $MeOH/CH_2Cl_2$ to 3% $MeOH/CH_2Cl_2$) to provide a dibenzyl product (0.15 g) and a monobenzyl product (0.13 g).

Dibenzyl product: MS (APCI+) m/z 696 (M+H)+;
Monobenzyl product: MS (APCI+) m/z 606 (M+H)+.

Example 18D

N-[(2S)-2-(tert-butoxycarbonylamino)-3-[4-(phenyl-methoxy)phenyl]propyl]-N-[2-(tert-butoxycarbony-lamino)-3-[4-(phenylmethoxy)phenyl]propyl]-N-ethylamine The dibenzyl product from Example 18C was processed as described in Example 17D to provide the title compound.

Example 18E

N-ethyl-N-[(2S)-2-(thiazol-5-ylmethoxycarbony-lamino)-3-[4-(phenylmethoxy)phenyl]propyl]-N-[2-(thiazol-5-ylmethoxycarbonylamino)-3-[4-(phenyl-methoxy)phenyl]propyl]amine The product from Example 18D was processed as described in Example 17E. The residue was purified by column chromatography on silica gel (ethyl acetate) to provide the title compound. $^1$H NMR ($CDCl_3$) δ 8.82-8.72 (m, 2H), 7.88-7.78 (m, 2H), 7.44-7.30 (m, 10H), 7.10-6.97 (m, 4H), 7.89-7.83 (m, 4H), 5.37-5.12 (m, 5H), 5.03 (s, 4H), 4.80 (br s, 1H), 3.90 (m, 1H), 3.82 (m, 1H), 3.05-2.28 (m, 10H), 0.88 (t, J=6.9 Hz, 1.5H); 0.77 (t, J=7.1 Hz, 1.5H); MS (ESI+) m/z 806 (M+H)+.

Example 19

N-ethyl-N-[(2S)-2-(thiazol-5-ylmethoxycarbony-lamino)-3-(4-hydroxyphenyl)propyl]-N-[2-(thiazol-5-ylmethoxycarbonylamino)-3-(4-hydroxyphenyl)propyl]amine

Example 19A

N-[(2S)-2-(tert-butoxycarbonylamino)-3-[4-(hy-droxy)phenyl]propyl]-N-[2-(tert-butoxycarbony-lamino)-3-[4-(phenylmethoxy)phenyl]propyl]-N-ethylamine The monobenzyl product from Example 18C was processed as described in Example 17D to provide the title compound.

Example 19B

N-[(2S)-2-(tert-butoxycarbonylamino)-3-(4-hydrox-yphenyl)propyl]-N-[2-(tert-butoxycarbonylamino)-3-(4-hydroxyphenyl)propyl]-N-ethylamine The product from Example 19A (82 mg, 0.13 mmol) in absolute ethanol (2 mL) was treated with 10% palladium on carbon (25 mg) under a $H_2$ atmosphere (1 atm) for 2 hours at ambient temperature. The mixture was filtered through celite and the solution was concentrated to provide the title compound as a colorless, amorphous solid (64 mg, 91%). $^1$H NMR ($CDCl_3$) δ 7.00 (d, J=8.5 Hz, 4H), 6.73 (d, J=8.5 Hz, 4H), 4.71 (br s, 1.3H), 4.58 (br s, 0.7H), 3.82-3.71 (m, 2H), 2.82-2.65 (m 4H), 2.59-2.28 (m, 6H), 1.42 (s, 12H), 1.38 (s, 6H), 0.95-0.84 (m, 3H); MS (APCI+) m/z 544 (M+H)+.

Example 19C

N-ethyl-N-[(2S)-2-(thiazol-5-ylmethoxycarbony-lamino)-3-(4-hydroxyphenyl)propyl]-N-[2-(thiazol-5-ylmethoxycarbonylamino)-3-(4-hydroxyphenyl)propyl]amine The product from Example 19B was processed as described in Example 17E. The residue was purified by column chromatography on silica gel ($CH_2Cl_2$:methanol, 19:1) to provide the title compound. $^1$H NMR ($CDCl_3$) δ 8.76 (s, 2H), 7.78 (s, 1H), 7.77 (s, 1H), 7.00-6.90 (m, 4H), 6.72-6.67 (m, 4H), 5.32-5.05 (m, 6H), 3.93-3.78 (m, 2H), 2.81-2.29 (m, 10H), 0.92-0.78 (m, 3H); MS (ESI+) m/z 626 (M+H)+.

Example 20

N-ethyl-N-[(2S)-2-(thiazol-5-ylmethoxycarbony-lamino)-3-(4-methoxyphenyl)propyl]-N-[2-(thiazol-5-ylmethoxycarbonylamino)-3-(4-methoxyphenyl)propyl]amine

Example 20A

N-[(2S)-2-(tert-butoxycarbonylamino)-3-(4-methox-yphenyl)propyl]-N-[2-(tert-butoxycarbonylamino)-3-(4-methoxyphenyl)propyl]-N-ethylamine The product from Example 19A (21 mg, 38 μmol) was treated with diazomethane in diethyl ether (~0.4 M, 1 mL) at ambient temperature. After stirring for 2 days, the solvent was removed under reduced pressure. The residue was dissolved in fresh diazomethane solution and stirred at ambient temperature for an additional 2 days. This process was repeated until TLC ($CHCl_3$:methanol, 19:1) indicated the reaction was complete. The residue was purified by column chromatography on silica gel ($CH_2Cl_2$:methanol, 99:1) to provide the title compound as a colorless amorphous solid (17 mg, 77%). $^1$H NMR ($CDCl_3$) δ 7.09 (d, J=8.9 Hz, 4H), 6.82 (d, J=8.5 Hz, 4H), 4.70 (br s, 1.3; H), 4.53 (br s, 0.7; H), 3.83-3.78 (m, 2H), 3.78 (s, 6H), 2.85-2.68 (m, 4H), 2.60-2.27 (m, 6H), 1.41 (s, 12H), 1.38 (s, 6H), 0.94-0.84 (m, 3H); MS (APCI+) m/z 572 (M+H)+.

Example 20B

N-ethyl-N-[(2S)-2-(thiazol-5-ylmethoxycarbony-lamino)-3-(4-methoxyphenyl)propyl]-N-[2-(thiazol-5-ylmethoxycarbonylamino)-3-(4-methoxyphenyl)propyl]amine The product from Example 20A was processed as described in Example 17E. The residue was purified by column chromatography on silica gel (ethyl acetate) to provide the title compound as an amorphous solid. $^1$H NMR (CDCl$_3$) δ 8.74 (s, 2H), 7.81 (s, 0.7H), 7.79 (s, 1.3H), 7.07-6.99 (m, 4H), 6.81-6.77 (m, 4H), 5.29-5.10 (m, 5H), 4.78 (br s, 1H), 3.89 (m, 2H), 3.78 (s, 6H), 2.82-2.28 (m, 10H), 0.88 (t, J=7.1 Hz, 1H), 0.78 (t, J=7.0 Hz, 2H); MS (APCI+) m/z 654 (M+H)$^+$.

Example 21

N,N'-bis[2-(thiazol-5-ylmethoxycabonylamino)-3-phenylpropyl]piperazine

Example 21A

N,N'-bis[2-(tert-butoxycarbonylamino)-3-phenylpropyl]piperazine

The product from Example 7A (1.98 g, 7.9 mmol) in 1,2-dichloroethane (32 mL) was treated with piperazine (0.29 g, 3.4 mmol) at ambient temperature. After stirring for ten minutes, the mixture was treated with acetic acid (0.45 mL, 7.8 mmol, 2.3 eq) and sodium triacetoxyborohydride (2.15 g, 10.1 mmol, 3.0 eq). After stirring at ambient temperature for 18 hours, the mixture was treated with ethyl acetate:10% NaHCO$_3$ (1:1, 50 mL). The phases were separated and the aqueous phase was extract with ethyl acetate (2×50 mL). All ethyl acetate extracts were combined, washed with 10% NaHCO$_3$ (50 mL), saturated brine (50 mL), dried over sodium sulfate, filtered and the filtrate was concentrated. The residue was purified by flash column chromatography on silica gel eluting with (chloroform:methanol, 98:2) to provide the title compound. R$_f$=0.39 (95:5 CHCl$_3$:CH$_3$OH); $^1$H NMR (CDCl$_3$) δ 7.32-7.14 (m, 10H), 4.58 (m, 2H), 3.90 (m, 2H), 2.86 (m, 4H), 2.52-2.17 (m, 12H), 1.42 (s, 18H); MS (ESI+) m/z 553 (M+H)$^+$.

Example 21B

N,N'-bis[2-(thiazol-5-ylmethoxycabonylamino)-3-phenylpropyl]piperazine

The product from Example 21A (359 mg, 0.65 mmol) in dichloromethane (10 mL) was treated with trifluoroacetic acid (5 mL) at ambient temperature. After stirring for one hour, the mixture was concentrated, a solution of 10% K$_2$CO$_3$ (25 mL) was added, and the aqueous mixture was extracted with chloroform (3×25 mL). The chloroform extracts were combined and concentrated. The residue was immersed in ethyl acetate (10 mL) and treated with a solution of 4-nitrophenyl 1,3-thiazol-5-ylmethyl carbonate [prepared from 4-nitrophenyl 1,3-thiazol-5-ylmethyl carbonate hydrochloride salt (453 mg, 1.43 mmol) by extraction with aqueous NaHCO$_3$] in ethyl acetate (20 mL). After stirring at ambient temperature for 1.5 hours, the reaction mixture was washed with 10% K$_2$CO$_3$ (5×30 mL). The aqueous washes were combined and extracted with chloroform (1×100 mL). The chloroform extract was combined with the ethyl acetate layer and washed with saturated brine (75 mL), dried over sodium sulfate, filtered, and the filtrate was concentrated. The residue was purified by flash column chromatography on silica gel eluting with (chloroform:methanol, 98:2) to provide the title compound (280 mg, 68%). R$_f$=0.32 (CHCl$_3$:CH$_3$OH, 95:5); $^1$H NMR (CDCl$_3$) δ 8.78 (s, 2H), 7.85 (s, 2H), 7.30-7.00 (m, 10H), 5.27 (s, 4H), 4.89 (m, 2H), 3.93 (m, 2H), 2.93 (dd, 2H), 2.81 (dd, 2H), 2.50-2.20 (m, 12H); MS (ESI+) m/z 635 (M+H)$^+$.

Example 22

N,N'-diethyl-N,N'-bis[2-(thiazol-5-ylmethoxycarbonylamino)-3-phenylpropyl]ethylenediamine N,N'-Diethylethylenediamine and the product from Example 7A were processed as described in Examples 21A and 21B. The residue was purified by column chromatography on silica gel (CH$_2$Cl$_2$:methanol, 19:1) to provide the title compound as a light yellow solid. $^1$H NMR (DMSO-d$_6$) δ 9.05 (s, 2H), 7.85 (s, 2H), 7.25-7.11 (m, 10H), 5.16 (s, 4H), 3.68 (m, 2H), 2.86 (dd, J=4.6, 13.8 Hz, 2H), 2.58-2.26 (m, 14H), 0.89 (t, J=6.9 Hz, 6H); MS (ESI+) m/z 665 (M+H)$^+$.

Example 23

N,N'-diisopropyl-N,N'-bis[2-(thiazol-5-ylmethoxycarbonylamino)-3-phenylpropyl]ethylenediamine N,N'-Diisopropylethylenediamine and the product from Example 7A were processed as described in Examples 21A and 21B. The residue was purified by column chromatography on silica gel (CH$_2$Cl$_2$:methanol, 19:1) to provide the title compound. $^1$H NMR (DMSO-d$_6$) δ 9.04 (s, 2H), 7.85 (s, 2H), 7.25-7.11 (m, 10H), 7.07 (d, J=8.8 Hz, 2H), 5.22-5.12 (m, 4H), 3.63 (m, 2H), 2.97-2.79 (m, 4H), 2.48-2.26 (m, 10H), 0.93-0.84 (m, 12H); MS (ESI+) m/z 693 (M+H)$^+$.

Example 24

N,N'-bis-[2-(thiazol-5-ylmethoxycarbonylamino)-3-phenylpropyl]-N-(thiazol-5-ylmethoxycarbonyl)ethylenediamine Ethylenediamine and the product from Example 7A were processed as described in Examples 21A and 21B. The residue was purified by column chromatography on silica gel (CH$_2$Cl$_2$:methanol, 9:1) to provide the title compound. $^1$H NMR (DMSO-d$_6$) δ 9.08-9.01 (m, 3H), 7.91 (s, 1H), 7.86 (s, 2H), 7.83 (s, 1H), 7.31-7.04 (m, 10H), 5.27-5.12 (m, 6H), 3.94 (m, 1H), 3.69 (m, 1H); MS (ESI+) m/z 750 (M+H)$^+$.

Example 25 tris-N-[2-(thiazol-5-ylmethoxycarbonylamino)-3-phenylpropyl]amine

EMBED ChemDraw.Document.4.5

Example 25A tris-N-[2-(tert-butoxycarbonylamino)-3-phenylpropyl]amine

The product from Example 7A (0.63 g, 2.5 mmol) and the product from Example 9A (1.00 g, 2.1 mmol) in dichloroethane (30 mL) were treated with sodium triacetoxyborohydride (0.70 g, 3.3 mmol) and acetic acid (0.14 mL, 2.4 mmol). After stirring at ambient temperature 3 days, the mixture was poured into ethyl acetate (100 mL), washed with saturated aqueous NaHCO$_3$ (2×100 mL), brine, dried over Na$_2$SO$_4$, filtered, and the filtrate was concentrated. The residue was purified by column chromatography on silica gel (hexanes:ethyl acetate, 3:1) to provide the title compound as a colorless solid (1.13 g, 76%). MS (ESI+) m/z 717 (M+H)$^+$.

Example 25B tris-N-[2-(thiazol-5-ylmethoxycarbonylamino)-3-phenylpropyl]amine The product from Example 25A (1.10 g, 1.52 mmol) in $CH_2Cl_2$ (16 mL) was treated with TFA (8 mL) at ambient temperature. After stirring for 2 hours, the mixture was concentrated under reduced pressure. The residue was partitioned between 20% aqueous $K_2CO_3$ and chloroform. The phases were separated and the aqueous phase was extracted with chloroform (3×50 mL). The organic phases were combined, concentrated and the resultant oil was dried under reduced pressure. The obtained oil was dissolved in a solution of 4-nitrophenyl 1,3-thiazol-5-ylmethyl carbonate [prepared from 4-nitrophenyl 1,3-thiazol-5-ylmethyl carbonate hydrochloride salt (1.59 g, 5.0 mmol) by extraction with aqueous $NaHCO_3$] in ethyl acetate (50 mL). After stirring at 60° C. under a $N_2$ atmosphere overnight, the mixture was allowed to cool to ambient temperature, washed with 10% aqueous $K_2CO_3$ (3×50 mL), brine, dried over $Na_2SO_4$, filtered, and the filtrate was concentrated under reduced pressure. The residue was purified by column chromatography on silica gel (ethyl acetate) to provide the title compound as a colorless solid (1.01 g, 79%). $^1$H NMR (DMSO-$d_6$) δ 8.93 (s, 2H), 8.92 (s, 1H), 7.76 (s, 1H), 7.71 (s, 2H), 7.26-7.11 (m, 15H), 5.14 (d, J=12.9 Hz, 2H), 5.08 (s, 2H), 4.99 (d, J=13.2 Hz, 2H), 3.84-3.72 (m, 3H); MS (ESI+) m/z 840 (M+H)$^+$.

EMBED ChemDraw.Document.4.5

Example 26

N-[(2R)-2-(thiazol-5-ylmethoxycarbonylamino)-3-phenylpropyl]-N-[(2S)-2-(thiazol-5-ylmethoxycarbonylamino)-3-phenylpropyl]amine

Example 26A (2R)-2-(tert-butoxycarbonylamino)-3-phenylpropylamine (2R)-2-(tert-Butoxycarbonylamino)-3-phenyl-1-propanol was processed as described in Examples 1A and 1B to provide the title compound.

EMBED ChemDraw.Document.4.5

Example 26B

N-[(2R)-2-(tert-butoxycarbonylamino)-3-phenylpropyl]-N-[(2S)-2-(tert-butoxycarbonylamino)-3-phenylpropyl]amine The product from Example 26A and the product from Example 1C were processed as described in Example 1D to provide the title compound.

Example 26C

N-[(2R)-2-(tert-butoxycarbonylamino)-3-phenylpropyl]-N-[(2S)-2-(tert-butoxycarbonylamino)-3-phenylpropyl]-N-[9-fluorenylmethoxycarbonyl]amine The product from Example 26B (1.28 g, 2.6 mmol) in tetrahydrofuran (11 mL) was treated with triethylamine (0.39 mL, 2.8 mmol) and 9-fluorenylmethyl chloroformate (0.72 g, 2.8 mmol) at ambient temperature. After stirring for 1 hour, the mixture was concentrated and the residue was dissolved in ethyl acetate (10 mL), wash with 10% $NaHCO_3$ (2×10 mL), 10% citric acid (2×10 mL), brine (10 mL), dried over sodium sulfate, filtered and the filtrate was concentrated. The residue was purified by flash column chromatography on silica gel eluting with chloroform (1.68 g, 90%). $^1$H NMR (CDCl$_3$) δ 7.82-6.94 (m, 18H), 4.93 (br s, 1H), 4.66-4.43 (m, 2H), 4.20 (t, 1H), 3.87-3.35 (m, 4H), 3.00-2.20 (m, 7H), 1.38-1.23 (m, 18H); MS (ESI+) m/z 706 (M+H)$^+$.

Example 26D

N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26C (952 mg, 1.35 mmol) in dichloromethane (20 mL) was treated with trifluoroacetic acid (10 mL) at ambient temperature. After stirring for one hour, the mixture was concentrated. The residue was immersed in an aqueous solution of 10% $K_2CO_3$ (10 mL) and extracted with ethyl acetate (3×10 mL). The organic phases were combined and treated with a solution of 4-nitrophenyl 1,3-thiazol-5-ylmethyl carbonate [prepared from 4-nitrophenyl 1,3-thiazol-5-ylmethyl carbonate hydrochloride salt (857 mg, 2.71 mmol, 2.0 eq) by extraction with aqueous $NaHCO_3$] in ethyl acetate (5 mL) at ambient temperature. After stirring for 1 hour, the mixture was washed with aqueous 10% $K_2CO_3$ (5×25 mL), brine (25 mL), dried over sodium sulfate, filtered, and the filtrate was concentrated. The residue was purified by flash column chromatography on silica gel eluting with (chloroform:methanol, 98:2) to provide the title compound (0.39, 30%). $^1$H NMR (CDCl$_3$) δ 8.78 (s, 2H), 7.84 (s, 2H), 7.33-7.04 (m, 10H), 5.00-4.86 (m, 4H), 3.98-3.83 (m, 4H), 2.90-2.50 (m, 9H); MS (ESI+) m/z 566 (M+H)$^+$.

Example 27

N-(2,2-dimethylpropyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (87.5 mg, 0.155 mmol) in 1,2-dichloroethane (3.0 mL) was treated with trimethylacetaldehyde (21 µL, 0.186 mmol) at ambient temperature. After stirring for 15 minutes, the mixture was treated with acetic acid (11 µL, 0.181 mmol) followed by sodium triacetoxyborohydride (53 mg, 0.248 mmol). After stirring at ambient temperature for 24 hours, the mixture was treated with aqueous 10% $NaHCO_3$ (5.0 mL) and extract with ethyl acetate (3×10 mL). The ethyl acetate extracts were combined, wash with brine (20 mL), dried over sodium sulfate, filtered, and the filtrate was concentrated. The residue was purified on a silica gel cartridge eluting with chloroform to provide the title compound (12.5 mg, 13%). $^1$H NMR (CDCl$_3$) δ 8.73 (s, 2H), 7.79 (s, 2H), 7.28-7.05 (m, 10H), 5.20 (s, 4H), 4.88-4.76 (br s, 2H), 3.90-3.66 (m, 2H), 2.87 (dd, 2H), 2.75-2.60 (m, 2H), 2.47 (d, 4H), 2.17 (s, 2H), 0.78 (s, 9H); MS (ESI+) m/z 636 (M+H)$^+$.

Example 28

N-(2-methylpropyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (87.5 mg, 0.155 mmol), 2-methylpropanal (17 µl, 0.186 mmol), acetic acid (11 µl, 0.181 mmol), and sodium triacetoxyborohydride (53 mg, 0.248 mmol) were processed as described in Example 27 to provide the title compound (50 mg, 52%). $^1$H NMR (CDCl$_3$) δ 8.72 (s, 2H), 7.78 (s, 2H), 7.29-7.06 (m, 10H), 5.20 (s, 4H), 4.77 (br s, 2H), 3.83 (br s, 2H), 2.88 (dd, 2H), 2.70 (m, 2H), 2.42 (m, 4H), 2.15 (d, 2H), 0.83 (d, 6H); MS (ESI+) m/z 622 (M+H)$^+$.

Example 29

N-(3-methylbutyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (87.5 mg, 0.155 mmol), 3-methylbutanal (20 µl, 0.186 mmol), acetic acid (11 µl, 0.181 mmol), and sodium triacetoxyborohydride (53 mg, 0.248 mmol) were processed as described in Example 27 to provide the title compound (23 mg, 23%). $^1$H NMR (CDCl$_3$) δ 8.73 (s, 2H), 7.79 (s, 2H), 7.29-7.07 (m, 10H), 5.20 (s, 4H), 4.79 (br s, 2H), 3.85 (m, 2H), 2.83 (dd, 2H), 2.73 (m, 2H), 2.43 (m, 5H), 1.46 (m, 2H), 1.17 (m, 2H), 0.82 (d, 6H); MS (ESI+) m/z 636 (M+H)$^+$.

Example 30

N-benzyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (87.5 mg, 0.155 mmol), benzaldehyde (19 µl, 0.186 mmol), acetic acid (11 µl, 0.181 mmol), and sodium triacetoxyborohydride (53 mg, 0.248 mmol) were processed as described in Example 27 to provide the title compound (40 mg, 39%). $^1$H NMR (CDCl$_3$) δ 8.72 (s, 2H), 7.80 (s, 2H), 7.32-6.95 (m, 15H), 5.21 (s, 4H), 4.65 (br s, 2H), 3.93 (br s, 2H), 3.56 (s, 2H), 2.78 (dd, 2H), 2.66 (br s, 2H), 2.45 (d, 4H); MS (ESI+) m/z 656 (M+H)$^+$.

Example 31

N,N-bis-[(2R)-2-(thiazol-5-ylmethoxycarbonylamino)-3-phenylpropyl]amine

Example 31A (2R)—N-tert-butoxycarbonyl-2-phenylmethylaziridine (2R)-2-(tert-Butoxycarbonylamino)-3-phenyl-1-propanol was processed as described in Example 1C to provide the title compound.

Example 31B

N,N-bis-[(2R)-2-(tert-butoxycarbonylamino)-3-phenylpropyl]amine

The product from Example 31A and the product from Example 26A were processed as described in Example 1D to provide the title compound.

Example 31C

N,N-bis[(2R)-2-(tert-butoxycarbonylamino)-3-phenylpropyl]-N-[9-fluorenylmethoxycarbonyl]amine The product from 31B was processed as described in Example 26C to provide the title compound.

Example 31D

N,N-bis[(2R)-2-(thiazol-5-ylmethoxycarbonylamino)-3-phenylpropyl]amine

The product from Example 31C (1.68 g, 2.4 mmol) in dichloromethane (20 mL) was treated with trifluoroacetic acid (10 mL) at ambient temperature. After stirring for one hour, the mixture was concentrated and a solution of aqueous 10% K$_2$CO$_3$ (10 mL) was added. The mixture was extracted with ethyl acetate (3×10 mL). The ethyl acetate extracts were combined and treated with a solution of 4-nitrophenyl 1,3-thiazol-5-ylmethyl carbonate [prepared from 4-nitrophenyl 1,3-thiazol-5-ylmethyl carbonate hydrochloride salt (1.52 g, 4.8 mmol) by extraction with aqueous NaHCO$_3$] in ethyl acetate (10 mL), triethylamine (0.67 mL, 4.8 mmol), and N,N-dimethylaminopyridine (0.58 g, 4.8 mmol, 2.0 eq). After stirring at ambient temperature for two hours, the mixture was wash with aqueous 10% K$_2$CO$_3$ (5×25 mL), brine (25 mL), dried over sodium sulfate, filtered and the filtrate was concentrated. The residue was purified by flash column chromatography on silica gel eluting with (chloroform:methanol 99:1) to provide the title compound (0.49 g, 37%). $^1$H NMR (CDCl$_3$) δ 8.78 (s, 2H), 7.82 (s, 2H), 7.33-7.07 (m, 10H), 5.02-4.85 (m, 4H), 4.02-3.84 (m, 4H), 2.92-2.66 (m, 9H); MS (ESI+) m/z 566 (M+H)$^+$.

Example 32

N-(2-methylpropyl)-N,N-bis[(2R)-2-(thiazol-5-ylmethoxycarbonylamino)-3-phenylpropyl]amine The product from Example 31D (80 mg, 0.141 mmol), 2-methylpropanal (15 µl, 0.170 mmol), acetic acid (10 µl, 0.166 mmol), and sodium triacetoxyborohydride (48 mg, 0.226 mmol) were processed as described in Example 27 to provide the title compound (40 mg, 44%). $^1$H NMR (CDCl$_3$) δ 8.73 (s, 2H), 7.76 (s, 2H), 7.32-7.12 (m, 10H), 5.35 (br s, 2H), 5.18 (q, 4H), 3.97 (br s, 2H), 2.83 (br s, 2H), 2.70 (dd, 2H), 2.41 (t, 2H), 2.21 (dd, 2H), 2.00 (m, 1H), 1.87 (dd, 1H), 0.72 (s, 6H); MS (ESI+) m/z 622 (M+H)$^+$.

Example 33

N-(3-methylbutyl)-N,N-bis[(2R)-2-(thiazol-5-ylmethoxycarbonylamino)-3-phenylpropyl]amine The product from Example 31D (80 mg, 0.141 mmol), 3-methylbutanal (18 µl, 0.170 mmol), acetic acid (10 µl, 0.166 mmol), and sodium triacetoxyborohydride (48 mg, 0.226 mmol) were processed as described in Example 27 to provide the title compound (40 mg, 45%). $^1$H NMR (CDCl$_3$) δ 8.73 (s, 2H), 7.78 (s, 2H), 7.32-7.11 (m, 10H), 5.32-5.08 (m, 6H), 3.95 (br s, 2H), 2.83 (br s, 2H), 2.71 (dd, 2H), 2.48-2.23 (m, 4H), 1.43 (m, 2H), 1.08 (m, 2H), 0.76 (t, 6H); MS (ESI+) m/z 636 (M+H)$^+$.

Example 34

N-benzyl-N,N-bis[(2R)-2-(thiazol-5-ylmethoxycarbonylamino)-3-phenylpropyl]amine

The product from Example 31D (80 mg, 0.141 mmol), benzaldehyde (17 μl, 0.170 mmol), acetic acid (10 μl, 0.166 mmol), and sodium triacetoxyborohydride (48 mg, 0.226 mmol) were processed as described in Example 27 to provide the title compound (17 mg, 18%). $^1$H NMR (CDCl$_3$) δ 8.73 (s, 2H), 7.78 (s, 2H), 7.32-7.08 (m, 15H), 5.12 (br s, 2H), 4.84 (br s, 2H), 4.12 (s, 2H), 3.13 (dd, 2H), 3.05-2.87 (m, 6H), 2.80-2.70 (m, 2H); MS (ESI+) m/z 656 (M+H)$^+$.

Example 35

N,N-bis[(2S)-2-(thiazol-5-ylmethoxycarbonylamino)-3-phenylpropyl]amine

The product from Example 1D (2.40 g, 5 mmol) in dichloromethane (20 mL) was treated with trifluoroacetic acid (10 mL) at ambient temperature. After stirring for two hours, the mixture was concentrated and treated with ethyl acetate (10 mL), a solution of 4-nitrophenyl 1,3-thiazol-5-ylmethyl carbonate [prepared from 4-nitrophenyl 1,3-thiazol-5-ylmethyl carbonate hydrochloride salt (3.46 g, 10.9 mmol) by extraction with aqueous NaHCO$_3$], triethylamine (1.52 mL, 10.9 mmol), and N,N-dimethylaminopyridine (1.21 g, 9.9 mmol) at ambient temperature. After stirring for 18 hours, the mixture was washed with aqueous 10% K$_2$CO$_3$ (5×50 mL), brine (50 mL), dried over sodium sulfate, filtered, and the filtrate was concentrated. The residue was purified by flash column chromatography on silica gel eluting with (chloroform: methanol, 98:2) to provide the title compound (1.18 g, 42%). $^1$H NMR (CDCl$_3$) δ 8.75 (s, 2H), 7.83 (s, 2H), 7.32-6.93 (m, 10H), 5.33-5.03 (m, 5H), 4.93 (br s, 2H), 3.92 (br s, 2H), 2.89-2.62 (m, 6H), 2.58 (dd, 2H); MS (ESI+) m/z 566 (M+H)$^+$.

Example 36

N-(thiazol-5-ylmethoxycarbonyl)-N,N-bis[(2S)-2-(thiazol-5-ylmethoxycarbonylamino)-3-phenylpropyl]amine The product from Example 35 (30 mg, 0.053 mmol) in ethyl acetate (2 mL) was treated with a solution of 4-nitrophenyl 1,3-thiazol-5-ylmethyl carbonate [prepared from 4-nitrophenyl 1,3-thiazol-5-ylmethyl carbonate hydrochloride salt (18 mg, 0.058 mmol) by extraction with aqueous NaHCO$_3$], triethylamine (15 μl, 0.106 mmol), and N,N-dimethylaminopyridine (6 mg, 0.053 mmol) at ambient temperature. After stirring for 18 hours, the mixture was washed with aqueous 10% K$_2$CO$_3$ (5×2 mL), brine (2 mL), dried over sodium sulfate, filtered, and the filtrate was concentrated. The residue was purify on a silica gel cartridge eluting with (chloroform:methanol, 99:1) to provide the title compound (13.4 mg, 36%). $^1$H NMR (CDCl$_3$) δ 8.80-8.68 (m, 3H), 7.81 (m, 3H), 7.31-6.96 (m, 10H), 5.27-5.05 (m, 6H), 4.04-3.25 (m, 5H), 3.11-2.98 (m, 2H), 2.89-2.56 (m, 5H); MS (ESI+) m/z 707 (M+H)$^+$.

Example 37

N-acetyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (50 mg, 0.088 mmol) in 1,2-dichloroethane (2 mL) was treated with triethylamine (14 μl, 0.097 mmol) and acetyl chloride (6.3 μl, 0.088 mmol) at ambient temperature. After stirring for two hours, the mixture was treated with ethyl acetate (8 mL), wash with aqueous 10% NaHCO$_3$ (2×10 mL), brine (10 mL), dried over sodium sulfate, filtered, and the filtrate was concentrated. The residue was purified on a silica gel cartridge eluting with (chloroform: methanol, 99:1) to provide the title compound (32.1 mg, 60%). $^1$H NMR (CDCl$_3$) δ 8.78 (d, 2H), 7.83 (d, 2H), 7.32-7.01 (m, 10H), 5.42 (d, 1H), 5.21 (d, 4H), 4.71 (br s, 1H), 4.01 (br s, 1H), 3.85 (m, 2H), 3.35 (m, 1H), 3.22 (dd, 1H), 3.00-2.55 (m, 5H), 1.57 (s, 3H); MS (ESI+) m/z 608 (M+H)$^+$.

Example 38

N-benzoyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 26D (50 mg, 0.088 mmol) in 1,2-dichloroethane (2 mL) was treated with triethylamine (14 μl, 0.097 mmol) and benzoyl chloride (10.3 μl, 0.088 mmol) at ambient temperature. After stirring for two hours, the mixture was treated with ethyl acetate (8 mL), wash with aqueous 10% NaHCO$_3$ (2×10 mL), brine (10 mL), dried over sodium sulfate, filtered, and the filtrate was concentrated. The residue was purified on a silica gel cartridge eluting with (chloroform: methanol, 99:1) to provide the title compound (28.4 mg, 48%). $^1$H NMR (CDCl$_3$) δ 8.78 (d, 2H), 7.83 (s, 2H), 7.40-6.75 (m, 15H), 5.24 (s, 4H), 4.27 (br s, 2H), 3.88 (br s, 2H), 3.28 (m, 3H), 2.91 (br s, 1H), 2.78 (br s, 1H), 2.45 (br s, 2H); MS (ESI+) m/z 670 (M+H)$^+$.

Example 39

N-(2-methylpropyl)-N,N-bis[(2S)-2-(thiazol-5-ylmethoxycarbonylamino)-3-phenylpropyl]amine The product from Example 35 (180 mg, 0.32 mmol) in 1,2-dichloroethane (2.0 mL) was treated with 2-methylpropanal (36 μl, 0.38 mmol) at ambient temperature. After stirring for 15 minutes, the mixture was treated with acetic acid (22 μl, 0.38 mmol) and sodium triacetoxyborohydride (108 mg, 0.51 mmol) at ambient temperature. After stirring for 2 hours, the mixture was treated with aqueous 10% sodium bicarbonate (2.0 mL) and extracted with ethyl acetate (3×5 mL). The ethyl acetate extracts were combined, washed with brine (5 mL), dried over sodium sulfate, filtered, and the filtrate was concentrated. The residue was purified by column chromatography on silica gel eluting with (chloroform: methanol, 99:1) to provide the title compound (155 mg, 78%). $^1$H NMR (CDCl$_3$) δ 8.73 (s, 2H), 7.75 (s, 2H), 7.31-7.11 (m, 10H), 5.33 (br s, 2H), 5.18 (q, 4H), 3.96 (br s, 2H), 2.83 (m, 2H), 2.71 (dd, 2H), 2.42 (t, 2H), 2.21 (dd, 2H), 2.05-1.83 (m, 2H), 1.46 (m, 1H), 0.72 (dd, 6H); MS (ESI+) m/z 622 (M+H)$^+$.

General Procedure A

Example 40 through Example 58 inclusive were prepared simultaneously on a Quest 210 synthesizer (Argonaut Technologies).

Nineteen vessels were each treated with 1,2-dichloroethane (1.0 mL), the product from Example 35 (50 mg, 0.088 mmol) and an aldehyde, listed below in Examples 40-58, at ambient temperature. After stirring for 15 minutes, each vessel was treated with acetic acid (6 μl, 0.106 mmol) and sodium triacetoxyborohydride (30 mg, 0.141 mmol) at ambient temperature. After stirring for 2 hours, each vessel was treated with aqueous 10% sodium bicarbonate (1.0 mL) and then extracted with ethyl acetate (3×2.0 mL). The ethyl acetate extracts were combined, concentrated, and each residue was purified on a silica gel cartridge eluting with (chloroform: methanol, 99:1).

Example 40

N-(2-phenylethyl)-N,N-bis[(2S)-2-(thiazol-5-yl-methoxycarbonylamino)-3-phenylpropyl]amine Phenylacetaldehyde (13 μl, 0.106 mmol) was processed as described in general procedure A to provide the title compound (26.8 mg, 45% yield). $^1$H NMR (CDCl$_3$) δ 8.72 (s, 2H), 7.78 (s, 2H), 7.32-6.94 (m, 15H), 5.37-5.02 (m, 6H), 3.95 (br s, 2H), 2.90-2.59 (m, 5H), 2.59-2.32 (m, 7H); MS (ESI+) m/z 670 (M+H)$^+$.

Example 41

N-(2-ethylbutyl)-N,N-bis[(2S)-2-(thiazol-5-yl-methoxycarbonylamino)-3-phenylpropyl]amine 2-Ethylbutanal (13 μl, 0.106 mmol) was processed as described in general procedure A to provide the title compound (24.0 mg, 42% yield). $^1$H NMR (CDCl$_3$) δ 8.74 (s, 2H), 7.76 (s, 2H), 7.32-7.08 (m, 10H), 5.39 (br s, 2H), 5.18 (q, 4H), 3.95 (br s, 2H), 2.86 (br s, 2H), 2.68 (dd, 2H), 2.40 (t, 2H), 2.25-2.07 (m, 3H), 1.85 (d, 1H), 1.40-1.14 (m, 2H), 1.14-0.92 (m, 3H), 0.75 (t, 3H), 0.64 (t, 3H); MS (ESI+) m/z 650 (M+H)$^+$.

Example 42

N-(4-pentenyl)-N,N-bis[(2S)-2-(thiazol-5-yl-methoxycarbonylamino)-3-phenylpropyl]amine 4-Pentenal (12 μl, 0.106 mmol) was processed as described in general procedure A to provide the title compound (13.7 mg, 24% yield). $^1$H NMR (CDCl$_3$) δ 8.73 (s, 2H), 7.78 (s, 2H), 7.32-7.08 (m, 10H), 5.77-5.60 (m, 1H), 5.35-5.05 (m, 6H), 4.95-4.85 (m, 2H), 3.95 (br s, 2H), 2.84 (br s, 2H), 2.70 (dd, 2H), 2.48-2.23 (m, 4H), 2.23-2.11 (m, 1H), 2.05-1.77 (m, 2H), 1.37-1.21 (m, 3H); MS (ESI+) m/z 634 (M+H)$^+$.

Example 43

N-(3-carboxypropyl)-N,N-bis[(2S)-2-(thiazol-5-ylmethoxycarbonylamino)-3-phenylpropyl]amine 4-Oxobutanoic acid (67 μl, 0.106 mmol) was processed as described in general procedure A to provide the title compound (6.6 mg, 11% yield). $^1$H NMR (CDCl$_3$) δ 8.71 (s, 2H), 7.75 (s, 2H), 7.32-7.06 (m, 10H), 5.73 (d, 2H), 5.14 (q, 4H), 4.05 (br s, 2H), 2.92-2.78 (m, 2H), 2.72-2.32 (m, 6H), 2.32-2.07 (m, 4H), 1.75-1.46 (m, 2H); MS (ESI+) m/z 652 (M+H)$^+$.

Example 44

N-(1H-imidazol-4-ylmethyl)-N,N-bis[(2S)-2-(thiazol-5-ylmethoxycarbonylamino)-3-phenylpropyl]amine 1H-Imidazole-4-carbaldehyde (11 mg, 0.106 mmol) was processed as described in general procedure A to provide the title compound (7.8 mg, 14% yield). $^1$H NMR (CDCl$_3$) δ 8.74 (s, 2H), 7.78 (s, 2H), 7.46 (s, 1H), 7.31-7.04 (m, 11H), 5.19 (q, 4H), 4.02 (br s, 2H), 3.70 (d, 1H), 3.32 (d, 1H), 2.78-2.62 (m, 4H), 2.52-2.31 (m, 4H); MS (ESI+) m/z 646 (M+H)$^+$.

Example 45

N-(3-pyridinylmethyl)-N,N-bis[(2S)-2-(thiazol-5-ylmethoxycarbonylamino)-3-phenylpropyl]amine Nicotinaldehyde (10 μl, 0.106 mmol) was processed as described in general procedure A to provide the title compound (20.6 mg, 35% yield). $^1$H NMR (CDCl$_3$) δ 8.78-8.37 (m, 4H), 7.83-7.77 (m, 2H), 7.32-6.98 (m, 12H), 5.35-5.08 (m, 6H), 4.08 (br s, 2H), 3.74 (d, 1H), 3.06 (d, 1H), 2.78 (m, 2H), 2.65 (dd, 2H), 2.44 (m, 2H), 2.30 (d, 2H); MS (ESI+) m/z 657 (M+H)$^+$.

Example 46

N-(4-pyridinylmethyl)-N,N-bis[(2S)-2-(thiazol-5-ylmethoxycarbonylamino)-3-phenylpropyl]amine Isonicotinaldehyde (10 μl, 0.106 mmol) was processed as described in general procedure A to provide the title compound (13.1 mg, 23% yield). $^1$H NMR (CDCl$_3$) δ 8.78-8.52 (m, 2H), 7.84-7.69 (m, 2H), 7.38-6.99 (m, 12H), 5.38-5.08 (m, 6H), 4.08 (br s, 2H), 3.74 (d, 1H), 3.08 (d, 1H), 2.78 (m, 2H), 2.65 (dd, 2H), 2.45 (m, 2H), 2.29 (d, 2H); MS (ESI+) m/z 657 (M+H)$^+$.

Example 47

N-(1H-pyrrol-2-ylmethyl)-N,N-bis[(2S)-2-(thiazol-5-ylmethoxycarbonylamino)-3-phenylpropyl]amine 1H-Pyrrole-2-carbaldehyde (10 mg, 0.106 mmol) was processed as described in general procedure A to provide the title compound (14.1 mg, 25% yield). MS (ESI+) m/z 566 (M+H)$^+$.

Example 48

N-butyl-N,N-bis[(2S)-2-(thiazol-5-ylmethoxycarbonylamino)-3-phenylpropyl]amine

Butanal (10 μl, 0.106 mmol) was processed as described in general procedure A to provide the title compound (21.6 mg, 39% yield). $^1$H NMR (CDCl$_3$) δ 8.74 (s, 2H), 7.78 (s, 2H), 7.32-7.08 (m, 10H), 5.33-5.07 (m, 6H), 3.94 (br s, 2H), 3.72 (m, 1H), 2.84 (br s, 2H), 2.70 (dd, 2H), 2.48-2.22 (m, 4H), 2.14 (m, 1H), 1.23-1.05 (m, 4H), 0.78 (t, 3H); MS (ESI+) m/z 622 (M+H)$^+$.

Example 49

N-octyl-N,N-bis[(2S)-2-(thiazol-5-ylmethoxycarbonylamino)-3-phenylpropyl]amine

Octanal (17 μl, 0.106 mmol) was processed as described in general procedure A to provide the title compound (19.2 mg, 32% yield). $^1$H NMR (CDCl$_3$) δ 8.73 (s, 2H), 7.78 (s, 2H), 7.32-7.08 (m, 10H), 5.34-5.05 (m, 6H), 3.95 (br s, 2H), 2.83 (br s, 2H), 2.71 (dd, 2H), 2.48-2.33 (m, 4H), 2.18 (m, 1H), 1.37-1.02 (m, 12H), 0.88 (t, 3H); MS (ESI+) m/z 678 (M+H)$^+$.

Example 50

N-[(2,5-dimethoxytetrahydro-3-furanyl)methyl]-N,N-bis[(2S)-2-(thiazol-5-ylmethoxycarbonylamino)-3-phenylpropyl]amine 2,5-Dimethoxytetrahydro-3-furancarboxaldehyde (17 µl, 0.106 mmol) was processed as described in general procedure A to provide the title compound (16.2 mg, 26% yield). $^1$H NMR (CDCl$_3$) δ 8.74 (s, 2H), 7.78 (s, 2H), 7.32-7.08 (m, 10H), 5.45-4.88 (m, 7H), 4.67 (m, 1H), 3.93 (br s, 2H), 3.45-3.14 (m, 6H), 2.88-1.93 (m, 12H); MS (ESI+) m/z 710 (M+H)$^+$.

Example 51

N-(cyclopropylmethyl)-N,N-bis[(2S)-2-(thiazol-5-ylmethoxycarbonylamino)-3-phenylpropyl]amine Cyclopropanecarbaldehyde (8 µl, 0.106 mmol) was processed as described in general procedure A to provide the title compound (22.9 mg, 42% yield). $^1$H NMR (CDCl$_3$) δ 8.74 (s, 2H), 7.78 (s, 2H), 7.32-7.08 (m, 10H), 5.32-5.07 (m, 6H), 3.95 (br s, 2H), 2.85 (br s, 2H), 2.72 (dd, 2H), 2.58-2.38 (m, 6H), 2.15-2.02 (m, 1H), 0.58 (m, 1H), 0.30 (m, 2H); MS (ESI+) m/z 620 (M+H)$^+$.

Example 52

N-(3,5,5-trimethylhexyl)-N,N-bis[(2S)-2-(thiazol-5-ylmethoxycarbonylamino)-3-phenylpropyl]amine 3,5,5-Trimethylhexanal (19 µl, 0.106 mmol) was processed as described in general procedure A to provide the title compound (23.6 mg, 39% yield). $^1$H NMR (CDCl$_3$) δ 8.74 (s, 2H), 7.78 (s, 2H), 7.32-7.10 (m, 10H), 5.34-5.05 (m, 5H), 3.95 (br s, 2H), 2.83 (br s, 2H), 2.78-2.65 (m, 2H), 2.48-2.12 (m, 6H), 1.39-0.92 (m, 5H), 0.92-0.74 (m, 7H), 0.85 (s, 3H), 0.82 (s, 3H); MS (ESI+) m/z 692 (M+H)$^+$.

Example 53

N-(2,2-dimethyl-4-pentenyl)-N,N-bis[(2S)-2-(thiazol-5-ylmethoxycarbonylamino)-3-phenylpropyl]amine 2,2-Dimethyl-4-pentenal (15 µl, 0.106 mmol) was processed as described in general procedure A to provide the title compound (7.6 mg, 13% yield). MS (ESI+) m/z 662 (M+H)$^+$.

Example 54

N-[2-((tert-butoxycarbonyl)amino)ethyl]-N,N-bis-[(2S)-2-(thiazol-5-ylmethoxycarbonylamino)-3-phenylpropyl]amine tert-Butyl 2-oxoethylcarbamate (17 µl, 0.106 mmol) was processed as described in general procedure A to provide the title compound (19.6 mg, 31% yield). $^1$H NMR (CDCl$_3$) δ 8.74 (s, 2H), 7.78 (s, 2H), 7.30-7.08 (m, 10H), 5.43-5.19 (m, 4H), 5.07 (d, 2H), 4.91 (br s, 1H), 3.96 (br s, 2H), 3.71 (m, 1H), 3.29 (m, 1H), 3.04 (m, 2H), 2.82 (dd, 2H), 2.73-2.18 (m, 5H), 1.49 (s, 1H), 1.42 (d, 9H); MS (ESI+) m/z 709 (M+H)$^+$.

Example 55

N-[3-(1,3-benzodioxol-5-yl)-2-methylpropyl]-N,N-bis[(2S)-2-(thiazol-5-ylmethoxycarbonylamino)-3-phenylpropyl]amine 3-(1,3-Benzodioxol-5-yl)-2-methylpropanal (25 µl, 0.106 mmol) was processed as described in general procedure A to provide the title compound (28.5 mg, 43% yield). $^1$H NMR (CDCl$_3$) δ 8.67 (d, 2H), 7.68 (d, 2H), 7.33-7.08 (m, 10H), 6.68 (m, 1H), 6.55-6.40 (m, 2H), 5.93 (s, 2H), 5.53-4.90 (m, 6H), 3.99 (br s, 2H), 2.93-2.61 (m, 4H), 2.53-1.72 (m, 7H), 1.25 (t, 1H), 0.65 (m, 3H); MS (ESI+) m/z 742 (M+H)$^+$.

Example 56

N-(6-methoxy-6-oxohexyl)-N,N-bis[(2S)-2-(thiazol-5-ylmethoxycarbonylamino)-3-phenylpropyl]amine Methyl 6-oxohexanoate (15 µl, 0.106 mmol) was processed as described in general procedure A to provide the title compound (16.9 mg, 28% yield). $^1$H NMR (CDCl$_3$) δ 8.75 (s, 2H), 7.78 (s, 2H), 7.32-7.10 (m, 10H), 5.41-5.04 (m, 6H), 3.95 (br s, 2H), 2.84 (br s, 2H), 2.69 (dd, 2H), 2.49-2.08 (m, 8H), 1.62-1.43 (m, 5H), 1.33-1.05 (m, 4H); MS (ESI+) m/z 694 (M+H)$^+$.

Example 57

N-[4-ethoxy-2-(ethoxycarbonyl)-4-oxobutyl]-N,N-bis[(2S)-2-(thiazol-5-ylmethoxycarbonylamino)-3-phenylpropyl]amine Diethyl 2-formylsuccinate (30 µl, 0.106 mmol) was processed as described in general procedure A to provide the title compound (15.4 mg, 23% yield). $^1$H NMR (CDCl$_3$) δ 8.73 (s, 2H), 7.78 (m, 2H), 7.32-7.06 (m, 10H), 5.45-4.94 (m, 6H), 4.25-3.80 (m, 5H), 2.95-2.20 (m, 11H), 1.32-1.11 (m, 6H); MS (ESI+) m/z 752 (M+H)$^+$.

Example 58

N-(3,5-ditert-butyl-2-hydroxybenzyl)-N,N-bis[(2S)-2-(thiazol-5-ylmethoxycarbonylamino)-3-phenylpropyl]amine 3,5-Ditert-butyl-2-hydroxybenzaldehyde (25 mg, 0.106 mmol) was processed as described in general procedure A to provide the title compound (7.8 mg, 11% yield). $^1$H NMR (CDCl$_3$) δ 9.82 (s, 1H), 8.72 (s, 2H), 7.75 (s, 2H), 7.32-7.08 (m, 11H), 6.72 (d, 1H), 5.36 (d, 2H), 4.98 (d, 2H), 4.25 (br s, 2H), 4.15 (d, 2H), 2.98-2.59 (m, 5H), 2.18 (dd, 2H), 1.58-1.23 (m, 21H); MS (ESI+) m/z 784 (M+H)$^+$.

General Procedure B

Example 59 through Example 66 inclusive were prepared simultaneously on a Quest 210 synthesizer (Argonaut Technologies).

Eight vessels were each treated with 1,2-dichloroethane (1.0 mL), the product from Example 26 (50 mg, 0.088 mmol) and an aldehyde, listed below in Examples 59-66, at ambient temperature. After stirring form 15 minutes, each vessel was treated with acetic acid (6 µl, 0.106 mmol) and sodium triacetoxyborohydride (30 mg, 0.141 mmol) at ambient temperature. After stirring for 2 hours, each vessel was treated with aqueous 10% sodium bicarbonate (1.0 mL) and then extract with ethyl acetate (3×2.0 mL). The ethyl acetate extracts were combined, concentrated, and each residue was purified on a silica gel cartridge eluting with (chloroform:methanol, 99:1).

Example 59

N-(2-naphthylmethyl)-N-[(2R)-2-(thiazol-5-yl-methoxycarbonylamino)-3-phenylpropyl]-N-[(2S)-2-(thiazol-5-ylmethoxycarbonylamino)-3-phenylpropyl]amine 2-Naphthaldehyde (17 mg, 0.106 mmol) was processed as described in general procedure B to provide the title compound (36.5 mg, 59% yield). $^1$H NMR (CDCl$_3$) δ 8.71 (s, 2H), 7.81 (s, 2H), 7.86-6.93 (m, 17H), 5.21 (s, 4H), 4.66 (br s, 2H), 3.98 (br s, 2H), 3.71 (s, 2H), 2.78 (dd, 2H), 2.66 (br s, 2H), 2.49 (m, 4H); MS (ESI+) m/z 706 (M+H)$^+$.

Example 60

N-(3-phenoxybenzyl)-N-[(2R)-2-(thiazol-5-yl-methoxycarbonylamino)-3-phenylpropyl]-N-[(2S)-2-(thiazol-5-ylmethoxycarbonylamino)]amine 3-Phenoxybenzaldehyde (19 μl, 0.106 mmol) was processed as described in general procedure B to provide the title compound (29.7 mg, 45% yield). $^1$H NMR (CDCl$_3$) δ 8.69 (s, 2H), 7.78 (s, 2H), 7.48-6.84 (m, 19H), 5.21 (s, 4H), 4.65 (br s, 2H), 3.93 (br s, 2H), 3.52 (s, 2H), 2.78 (dd, 2H), 2.67 (br s, 2H), 2.45 (m, 4H); MS (ESI+) m/z 748 (M+H)$^+$.

Example 61

N-(3-quinolinylmethyl)-N-[(2R)-2-(thiazol-5-yl-methoxycarbonylamino)-3-phenylpropyl]-N-[(2S)-2-(thiazol-5-ylmethoxycarbonylamino)-3-phenylpropyl]amine 3-Quinolinecarbaldehyde (17 mg, 0.106 mmol) was processed as described in general procedure B to provide the title compound (15.0 mg, 24% yield). $^1$H NMR (CDCl$_3$) δ 8.95-6.97 (m, 18H), 5.21 (s, 4H), 4.94 (d, 2H), 4.67 (br s, 2H), 4.02 (br s, 2H), 3.78 (s, 2H), 2.80 (dd, 2H), 2.63 (br s, 2H), 2.52 (d, 4H); MS (ESI+) m/z 707 (M+H)$^+$.

Example 62

N-(3-methoxybenzyl)-N-[(2R)-2-(thiazol-5-yl-methoxycarbonylamino)-3-phenylpropyl]-N-[(2S)-2-(thiazol-5-ylmethoxycarbonylamino)-3-phenylpropyl]amine 3-Methoxybenzaldehyde (13 μl, 0.106 mmol) was processed as described in general procedure B to provide the title compound (24.9 mg, 41% yield). $^1$H NMR (CDCl$_3$) δ 8.72 (s, 2H), 7.79 (s, 2H), 7.28-6.99 (m, 11H), 6.85-6.75 (m, 3H), 5.20 (s, 4H), 4.66 (br s, 2H), 3.92 (br s, 2H), 3.73 (s, 3H), 3.54 (s, 2H), 2.79 (dd, 2H), 2.67 (m, 2H), 2.45 (d, 4H); MS (ESI+) m/z 686 (M+H)$^+$.

Example 63

N-(3,4-dimethoxybenzyl)-N-[(2R)-2-(thiazol-5-yl-methoxycarbonylamino)-3-phenylpropyl]-N-[(2S)-2-(thiazol-5-ylmethoxycarbonylamino)-3-phenylpropyl]amine 3,4-Dimethoxybenzaldehyde (18 mg, 0.106 mmol) was processed as described in general procedure B to provide the title compound (24.2 mg, 38% yield). $^1$H NMR (CDCl$_3$) δ 8.71 (s, 2H), 7.78 (s, 2H), 7.28-6.99 (m, 10H), 6.87-6.67 (m, 3H), 5.19 (s, 4H), 4.66 (br s, 2H), 3.93 (br s, 2H), 3.87 (s, 3H), 3.76 (s, 3H), 3.49 (s, 2H), 2.80 (dd, 2H), 2.66 (m, 2H), 2.44 (d, 4H); MS (ESI+) m/z 716 (M+H)$^+$.

Example 64

N-[4-(3-(dimethylamino)propoxy)benzyl]-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine 4-[3-(Dimethylamino)propoxy]benzaldehyde (22 μl, 0.106 mmol) was processed as described in general procedure B to provide the title compound (13.0 mg, 19% yield). $^1$H NMR (CDCl$_3$) δ 8.72 (s, 2H), 7.86-7.78 (m, 4H), 7.24-6.73 (m, 10H), 5.21 (s, 4H), 4.65 (br s, 2H), 4.05 (dt, 3H), 3.92 (br s, 2H), 3.48 (s, 2H), 2.77 (dd, 2H), 2.67 (m, 2H), 2.49-2.38 (m, 5H), 2.25 (s, 6H), 1.97 (m, 4H); MS (ESI+) m/z 757 (M+H)$^+$.

Example 65

N-(4-dimethylaminobenzyl)-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine 4-Dimethylaminobenzaldehyde (16 mg, 0.106 mmol) was processed as described in general procedure B to provide the title compound (15.0 mg, 24% yield). $^1$H NMR (CDCl$_3$) δ 8.72 (s, 2H), 7.80 (s, 2H), 7.28-6.98 (m, 12H), 6.61 (d, 2H), 5.22 (s, 2H), 4.68 (br s, 2H), 3.92 (br s, 2H), 3.46 (s, 2H), 2.92 (s, 6H), 2.78 (dd, 2H), 2.70 (m, 2H), 2.42 (d, 4H); MS (ESI+) m/z 699 (M+H)$^+$.

Example 66

N-[(6-methoxy-2-naphthyl)methyl]-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine 6-Methoxy-2-naphthaldehyde (20 mg, 0.106 mmol) was processed as described in general procedure B to provide the title compound (32.5 mg, 50% yield). $^1$H NMR (CDCl$_3$) δ 8.71 (s, 2H), 7.81 (s, 2H), 7.65-6.95 (m, 16H), 5.21 (s, 4H), 4.66 (br s, 2H), 3.97 (br s, 2H), 3.93 (s, 3H), 3.67 (s, 2H), 2.78 (dd, 2H), 2.68 (m, 2H), 2.48 (m, 4H); MS (ESI+) m/z 736 (M+H)$^+$.

General Procedure C

Example 67 through Example 69 inclusive were prepared simultaneously on a Quest 210 synthesizer (Argonaut Technologies).

Three reaction vessels were each treated with methanol (1.0 mL), the product from Example 1D (50 mg, 0.103 mmol, 1.0 eq) and an aldehyde, listed below in Examples 67-69. After stirring for 15 minutes, each vessel was treated with acetic acid (1 drop) and sodium cyanoborohydride (14 mg, 0.227 mmol, 2.2 eq) at ambient temperature. After stirring for 18 hours, each vessel was concentrated and the residue treated with ethyl acetate (3 mL). The ethyl acetate was wash with water (2×3 mL) and concentrated. Each residue was treated with methylene chloride (1.5 mL) and trifluoroacetic acid (1.5 mL). After stirring for 1 hour at ambient temperature, each mixture was concentrated, treated with ethyl acetate (3 mL) and wash with aqueous 5% $K_2CO_3$ (2×3 mL). The ethyl acetate mixtures were treated with 4-nitrophenyl 1,3-thiazol-5-ylmethyl carbonate [prepared from 4-nitrophenyl 1,3-thiazol-5-ylmethyl carbonate hydrochloride salt (72 mg, 0.227 mmol, 2.2 eq) by extraction with aqueous $NaHCO_3$], triethylamine (32 µl, 0.227 mmol, 2.2 eq) and N,N-dimethylaminopyridine (25 mg, 0.206 mmol, 2.0 eq) at ambient temperature. After stirring for 18 hours, each mixture was wash with aqueous 10% $K_2CO_3$ (6×5 mL) and concentrated. Each residue was purified using a silica gel cartridge eluting with chloroform.

Example 67

N-(3-methylbutyl)-N,N-bis[(2S)-2-(thiazol-5-ylmethoxycarbonylamino)-3-phenylpropyl]amine 3-Methylbutanal (11 µl, 0.103 mmol) was processed as described in general procedure C to provide the title compound (19 mg, 29% yield). $^1$H NMR ($CDCl_3$) δ 8.73 (s, 2H), 7.78 (s, 2H), 7.32-7.08 (m, 10H), 5.32-5.06 (m, 4H), 3.95 (br s, 2H), 2.92-2.58 (m, 4H), 2.48-2.23 (m, 4H), 2.23-2.09 (m, 1H), 1.49-0.81 (m, 6H), 0.77 (t, 6H); MS (ESI+) m/z 636 $(M+H)^+$.

Example 68

N-benzyl-N,N-bis[(2S)-2-(thiazol-5-ylmethoxycarbonylamino)-3-phenylpropyl]amine

Benzaldehyde (11 µl, 0.103 mmol) was processed as described in general procedure C to provide the title compound (14 mg, 21% yield). $^1$H NMR ($CDCl_3$) δ 8.74 (s, 2H), 7.78 (s, 2H), 7.30-7.01 (m, 15H), 5.39 (s, 2H), 5.34-5.12 (m, 4H), 4.06 (br s, 2H), 3.74 (d, 1H), 3.04 (d, 1H), 2.94-2.72 (m, 2H), 2.64 (dd, 2H), 2.53-2.37 (m, 2H), 2.28 (dd, 2H); MS (ESI+) m/z 656 $(M+H)^+$.

Example 69

N-(cyclohexylmethyl)-N,N-bis[(2S)-2-(thiazol-5-ylmethoxycarbonylamino)-3-phenylpropyl]amine Cyclohexylaldehyde (13 µl, 0.103 mmol) was processed as described in general procedure C to provide the title compound (26 mg, 38% yield). $^1$H NMR ($CDCl_3$) δ 8.73 (s, 2H), 7.76 (s, 2H), 7.32-7.11 (m, 10H), 5.39 (s, 2H), 5.34 (br s, 2H), 5.28-5.04 (m, 4H), 3.95 (br s, 2H), 2.85 (br s, 2H), 2.68 (dd, 2H), 2.38 (t, 2H), 2.22 (dd, 2H), 2.08 (dd, 1H), 1.91-1.81 (m, 1H), 1.75-1.57 (m, 2H), 1.50-1.37 (m, 2H), 1.21-0.95 (m, 4H); MS (ESI+) m/z 662 $(M+H)^+$.

Example 70

N-ethyl-N,N-bis[(2R)-2-(thiazol-5-ylmethoxycarbonylamino)-3-phenylpropyl]amine

Example 70A (2R)—N-tert-butoxycarbonyl-2-phenylmethylaziridine (2R)-2-(tert-Butoxycarbonylamino)-3-phenyl-1-propanol was processed as described in Example 1C to provide the title compound.

Example 70B tert-butyl (1R)-1-benzyl-2-(benzylamino)ethylcarbamate

The product from Example 70A (1.77 g, 7.6 mmol) in toluene (15 mL) was treated with benzylamine (8.4 mL, 76 mmol) in a sealed tube. After heating at 100° C. for 4 days, the mixture was allowed to cool to ambient temperature and was concentrated. The residue was dissolved in ethyl acetate (50 mL) and the ethyl acetate was washed with 10% citric acid (2×50 mL) and brine (50 mL). A precipitate fell out of the brine. The brine wash was filtered and the filter cake dissolved in ethyl acetate. All the ethyl acetate solutions were combined, wash with aqueous 10% $NaHCO_3$ (2×100 mL), brine, (100 mL), dried over magnesium sulfate, filtered, and the filtrate was concentrated to provide the title compound as a white solid (2.58 g). $^1$H NMR ($CDCl_3$) δ 7.49-7.12 (m, 10H), 4.98 (m, 1H), 4.00 (br s, 1H), 3.87 (q, 2H), 2.94-2.73 (m, 5H); MS (ESI+) m/z 341 $(M+H)^+$.

Example 70C tert-butyl (1R)-2-amino-1-benzylethylcarbamate

The product from Example 70B (3.36 g, 9.9 mmol) in methanol (10 mL) was treated with 20% $Pd(OH)_2/C$ (wet) (335 mg) under a hydrogen atmosphere (4 atmospheres) at 50° C. After 3.25 hours, the solution was filtered and the filtrate was concentrated. The residue was dried under reduced pressure to provide the title compound as a white solid (2.46 g). $^1$H NMR (DMSO-$d_6$) δ 7.32-7.12 (m, 5H), 6.54 (d, 1H), 3.53 (m, 1H), 2.79-2.69 (dd, 2H), 2.66-2.50 (m, 4H), 1.31 (s, 9H); MS (ESI+) m/z 251 $(M+H)^+$.

Example 70D

N,N-bis[(2R)-2-(tert-butoxycarbonylamino)-3-phenylpropyl]amine

The product from Example 70C and the product from Example 70A were processed as described in Example 1D to provide the title compound.

Example 70E

N,N-bis[(2R)-2-(tert-butoxycarbonylamino)-3-phenylpropyl]-N-ethylamine

The product from Example 70D was processed as described in Example 1E to provide the title compound.

Example 70F

N-ethyl-N,N-bis[(2S)-2-(thiazol-5-ylmethoxycarbonylamino)-3-phenylpropyl]amine

The product from Example 70E (87 mg, 0.17 mmol) in dichloromethane (1.8 mL) was treated with trifluoroacetic acid (1.0 mL) at ambient temperature. After stirring for 2 hours, the mixture was concentrated and treated with aqueous 10% $K_2CO_3$ (2.4 mL). The aqueous solution was extracted with ethyl acetate (3×3 mL). The ethyl acetate extracts were combined and treated with 4-nitrophenyl 1,3-thiazol-5-ylmethyl carbonate [prepared from 4-nitrophenyl 1,3-thiazol-5-ylmethyl carbonate hydrochloride salt (100 mg, 0.36 mmol) by extraction with aqueous $NaHCO_3$] in ethyl acetate (6 mL). After heating at 60° C. for 18 hours, the mixture was allowed to cool to ambient temperature and concentrated. The residue was purified by flash column chromatography on silica gel eluting with (chloroform:methanol, 98:2) to provide the title compound (33.5 mg, 31%). $^1$H NMR ($CDCl_3$) δ 8.76 (s, 2H), 7.85 (s, 2H), 7.32-7.09 (m, 10H), 5.37-5.17 (m, 6H), 4.15 (br s, 2H), 3.61-2.65 (m, 10H), 1.24 (t, 3H); MS (ESI+) m/z 594 (M+H)$^+$.

Example 71

N-ethyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine

Example 71A

N-[(2R)-2-(tert-butoxycarbonylamino)-3-phenylpropyl]-N-[(2S)-2-(tert-butoxycarbonylamino)-3-phenylpropyl]amine The product from Example 70C and the product from Example 1C were processed as described in Example 1D to provide the title compound.

Example 71B

N-[(2R)-2-(tert-butoxycarbonylamino)-3-phenylpropyl]-N-[(2S)-2-(tert-butoxycarbonylamino)-3-phenylpropyl]-N-ethylamine The product from Example 71A was processed as described in Example 1E to provide the title compound.

Example 71C

N-ethyl-N-[(2R)-2-(thiazol-5-ylmethoxycarbonylamino)-3-phenylpropyl]-N-[(2S)-2-(thiazol-5-ylmethoxycarbonylamino)-3-phenylpropyl]amine The product from Example 71B (86 mg, 0.17 mmol) in dichloromethane (1.8 mL) was treated with trifluoroacetic acid (1.0 mL) at ambient temperature. After stirring for 2 hours, the mixture was concentrated and treated with aqueous 10% $K_2CO_3$ (2.4 mL). The aqueous mixture was extracted with ethyl acetate (3×3 mL). The ethyl acetate extracts were combined and treated with 4-nitrophenyl 1,3-thiazol-5-ylmethyl carbonate [prepared from 4-nitrophenyl 1,3-thiazol-5-ylmethyl carbonate hydrochloride salt (99 mg, 0.35 mmol) by extraction with aqueous $NaHCO_3$] in ethyl acetate (6 mL). After heat at 60° C. for 18 hours, the mixture was allowed to cool to ambient temperature and was concentrated. The residue was purified by flash column chromatography on silica gel eluting with (chloroform:methanol, 98:2) to provide the title compound (34.1 mg, 32%). $^1$H NMR ($CDCl_3$) δ 8.78 (s, 2H), 7.85 (s, 2H), 7.32-7.05 (m, 10H), 5.40-5.17 (m, 6H), 4.20 (br s, 2H), 3.49-2.55 (m, 10H), 0.85 (t, 3H); MS (ESI+) m/z 594 (M+H)$^+$.

The term "therapeutically acceptable salt" or "pharmaceutically acceptable salt" is intended to describe a zwitterions or a salt derived from pharmaceutically acceptable inorganic and organic acids and bases, and retains the biological effectiveness of the free acid or base of the specified compound without undue toxicity, irritation, and allergic response, commensurate with a reasonable benefit/risk ratio, effective for their intended use and is not biologically or otherwise undesirable; and as used herein, the term "therapeutically acceptable salt" or "pharmaceutically acceptable salt" refers to salts that are well known in the art. For example, S. M Berge et al. describe pharmaceutically acceptable salts in detail in *J. Pharmaceutical Sciences*, 66:p1-19, 1977).

Accordingly, the compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethane-sulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as sodium, potassium, calcium or magnesium or with organic bases.

The administration of a compound or combination of compounds of the present invention, a pharmaceutically acceptable salt, prodrug, salt of a prodrug, or combination thereof and a compound or a pharmaceutically acceptable salt thereof, which is metabolized by cytochrome P450 monooxygenase is useful for improving in humans the pharmacokinetics (i.e. increasing half-life, increase the time to peak plasma concentration, increase blood levels) of the compound which is metabolized by cytochrome P450 monooxygenase.

When administered in combination, the compound or combination of compounds of the present invention (or a pharmaceutically acceptable salt, prodrug, salt of a prodrug, or combination thereof) and a compound (or a pharmaceutically acceptable salt thereof) which is metabolized by cytochrome P450 monooxygenase can be formulated as separate compositions which are administered at the same time or different times, or can be administered as a single composition.

The total daily dose of a compound of formula I, II or III to be administered to a human or other mammal host in single or divided doses may be in amounts, for example, from 0.001 to 300 mg/kg body weight daily and more usually 0.1 to 50 mg/kg and even more usually 0.1 to 25 mg/kg. Dosage unit compositions may contain such amounts of submultiples thereof to make up the daily dose.

The total daily dose of the drug which is metabolized by cytochrome P450 monooxygenase to be administered to a human or other mammal is well known and can be readily determined by one of ordinary skill in the art. Dosage unit compositions may contain such amounts of submultiples thereof to make up the daily dose.

The amount of active ingredient that may be combined with the carrier materials to produce a single dosage form of each drug, individually or in combination, will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

It will be understood that the combination (as individual compositions or as a single composition) of a drug (or a pharmaceutically acceptable salt) which is metabolized by cytochrome P450 monooxygenase, and a compound or combination of compounds of the present invention (or a pharmaceutically acceptable salt, prodrug, salt of a prodrug, or combination thereof), can be administered alone or be administered in the form of a pharmaceutical composition in which the agents (as individual compositions or as a single composition) are administered in combination with a pharmaceutically acceptable carriers, adjuvants, diluents, vehicles, or combinations thereof.

The term "pharmaceutically acceptable carrier, adjuvants, diluents or vehicles" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be formulated in a conventional manner using one or more of the aforementioned pharmaceutically acceptable carriers.

Such pharmaceutical compositions of the present invention (as individual compositions or as a single composition) may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The combination of therapeutic agents of the present invention (as individual compositions or as a single composition) can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:
1. A compound of formula I or a pharmaceutically acceptable salt, prodrug, salt of a prodrug, or a combination thereof, wherein
$R_1$ is selected from the group consisting of aryl, heteroaryl and heterocycle;
$R_2$ and $R_3$ are each independently selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_CR_D)$alkyl;
$R_4$ is selected from the group consisting of aryl, heteroaryl, and heterocycle;
$R_5$ and $R_6$ are each independently selected from the group consisting of hydrogen, lower alkyl and arylalkyl;
m is 0-3;
n is 0-3;
$A_1$ is selected from the group consisting of O and $NR_{A1}$ wherein $R_{A1}$ is selected from the group consisting of hydrogen and lower alkyl;
$A_2$ is absent or selected from the group consisting of O and $NR_{A2}$ wherein $R_{A2}$ is selected from the group consisting of hydrogen and lower alkyl;
$X_1$ and $X_2$ are each independently selected from the group consisting of O and S;
L is selected from the group consisting of p is 1-5;
$R_8$ and $R_9$ are each independently selected from the group consisting of hydrogen, alkenyl, alkenylcarbonyl, alkoxyalkyl, alkoxycarbonyl, alkoxycarbonylalkyl, alkyl, alkylcarbonyl, alkylcarbonylalkyl, alkylcarbonyloxyalkyl, alkynyl, alkynylcarbonyl, arylalkoxycarbonyl, arylalkyl, arylalkylcarbonyl, arylcarbonyl, aryloxyalkyl, arylthioalkoxyalkyl, arylthioalkyl, carboxyalkyl, cyanoalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocyclethioalkoxyalkyl, heterocyclethioalkyl, hydroxyalkyl, $(NR_CR_D)$alkyl and $R_{10}$ is selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_AR_B)$alkyl;
$R_{11}$ is selected from the group consisting of hydrogen, lower alkyl and arylalkyl;
$R_{12}$ is selected from the group consisting of aryl, heteroaryl and heterocycle;
q is 0-3;
$X_3$ is selected from the group consisting of O and S; and
$A_3$ is absent or selected from the group consisting of O and $NR_{A3}$ wherein $R_A3$ is selected from the group consisting of hydrogen and lower alkyl;
$R_C$ and $R_D$ are each independently selected from the group consisting of hydrogen, alkoxycarbonyl, alkyl, alkylcarbonyl, alkylsulfonyl, arylalkoxycarbonyl, arylsulfonyl, formyl, $(NR_ER_F)$carbonyl and $(NR_ER_F)$sulfonyl;
$R_E$ and $R_F$ are each independently selected from the group consisting of hydrogen and lower alkyl; and
wherein any one of said aryl, heteroaryl, heterocycle, cycloalkyl, cycloalkyl moiety of said cycloalkylalkyl, aryl moieties of said arylalkoxyalkyl, arylalkoxycarbonyl, arylalkyl, arylalkylcarbonyl, arylcarbonyl, aryloxyalkyl, aryloxycarbonyl, arylthioalkoxyalkyl and arylthioalkyl, heteroaryl moieties of said heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl and heteroarylthioalkyl, and heterocycle moieties of said heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, and heterocyclethioalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ are independently selected from the group consisting of hydrogen and lower alkyl.

2. The compound according to claim 1, wherein

R$_2$ and R$_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl;

R$_8$ and R$_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, (NR$_C$R$_D$)alkyl and

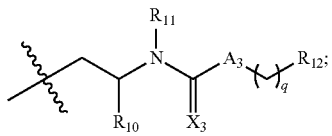

R$_{10}$ is selected from the group consisting of hydrogen, alkoxycarbonylalkyl, alkyl, arylalkoxyalkyl, arylalkyl and cycloalkylalkyl;

R$_C$ and R$_D$ are each independently selected from the group consisting of hydrogen, alkyl and alkoxycarbonyl.

3. The compound according to claim 1, wherein

R$_1$ is heteroaryl;

R$_2$ and R$_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl;

R$_4$ is heteroaryl;

R$_8$ and R$_9$ are each independently selected from the group consisting of hydrogen, alkenyl, alkoxycarbonylalkyl, alkyl, alkylcarbonyl, arylalkyl, arylcarbonyl, carboxyalkyl, cycloalkylalkyl, di(alkoxycarbonyl)alkyl, heteroarylalkoxycarbonyl, heterocyclealkoxycarbonyl, heteroarylalkyl, heterocyclealkyl, (NR$_C$R$_D$)alkyl and

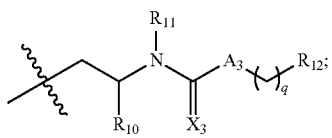

R$_{10}$ is selected from the group consisting of hydrogen, alkyl and arylalkyl;

R$_{12}$ is heteroaryl; and

R$_C$ and R$_D$ are each independently selected from the group consisting of hydrogen, alkyl and alkoxycarbonyl.

4. The compound according to claim 1, wherein

R$_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl;

R$_2$ and R$_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl;

R$_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl;

R$_C$ and R$_D$ are independently selected from the group consisting of hydrogen, alkyl and alkoxycarbonyl;

R$_8$ and R$_9$ are independently selected from the group consisting of hydrogen, alkyl, heteroarylalkoxycarbonyl and heterocyclealkoxycarbonyl;

R$_{10}$ is selected from the group consisting of hydrogen and arylalkyl; and

R$_{12}$ is heteroaryl.

5. The compound according to claim 1, wherein

R$_1$ is heteroaryl wherein said heteroaryl is selected from the group consisting of imidazolyl, oxazolyl, pyrazolyl, pyridinyl, thiazolyl, and thienyl;

R$_2$ and R$_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl;

R$_4$ is heteroaryl wherein said heteroaryl is selected from the group consisting of imidazolyl, oxazolyl, pyrazolyl, pyridinyl, thiazolyl, and thienyl;

R$_C$ and R$_D$ are independently selected from the group consisting of hydrogen, alkyl and alkoxycarbonyl;

R$_8$ and R$_9$ are independently selected from the group consisting of hydrogen, alkyl and heteroarylalkoxycarbonyl wherein the heteroaryl portion of heteroarylalkoxycarbonyl is selected from the group consisting of imidazolyl, oxazolyl, pyrazolyl, pyridinyl, thiazolyl, and thienyl;

R$_{10}$ is selected from the group consisting of hydrogen and arylalkyl wherein the arylalkyl is phenylmethyl; and R$_{12}$ is heteroaryl wherein said heteroaryl is selected from the group consisting of imidazolyl, oxazolyl, pyrazolyl, pyridinyl, thiazolyl, and thienyl.

6. The compound according to claim 1 of formula III

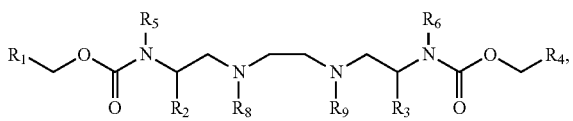

or a pharmaceutically acceptable salt, prodrug, salt of a prodrug, or a combination thereof, wherein R$_1$ is selected from the group consisting of aryl, heteroaryl and heterocycle;

R$_2$ and R$_3$ are each independently selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_C R_D)$alkyl;

$R_4$ is selected from the group consisting of aryl, heteroaryl, and heterocycle;

$R_5$ and $R_6$ are each independently selected from the group consisting of hydrogen, lower alkyl and arylalkyl;

$R_8$ and $R_9$ are each independently selected from the group consisting of hydrogen, alkenyl, alkenylcarbonyl, alkoxyalkyl, alkoxycarbonyl, alkoxycarbonylalkyl, alkyl, alkylcarbonyl, alkylcarbonylalkyl, alkylcarbonyloxyalkyl, alkynyl, alkynylcarbonyl, arylalkoxycarbonyl, arylalkyl, arylalkylcarbonyl, arylcarbonyl, aryloxyalkyl, arylthioalkoxyalkyl, arylthioalkyl, carboxyalkyl, cyanoalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocyclethioalkoxyalkyl, heterocyclethioalkyl, hydroxyalkyl, $(NR_C R_D)$alkyl and

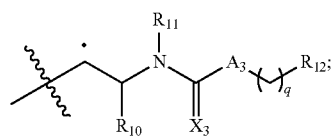

$R_{10}$ is selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_A R_B)$alkyl;

$R_{11}$ is selected from the group consisting of hydrogen, lower alkyl and arylalkyl;

$R_{12}$ is selected from the group consisting of aryl, heteroaryl and heterocycle;

q is 0-3;

$X_3$ is selected from the group consisting of O and S; and $A_3$ is absent or selected from the group consisting of O and $NR_{A3}$ wherein $R_{A3}$ is selected from the group consisting of hydrogen and lower alkyl;

$R_C$ and $R_D$ are each independently selected from the group consisting of hydrogen, alkoxycarbonyl, alkyl, alkylcarbonyl, alkylsulfonyl, arylalkoxycarbonyl, arylsulfonyl, formyl, $(NR_E R_F)$carbonyl and $(NR_E R_F)$sulfonyl; and $R_E$ and $R_F$ are each independently selected from the group consisting of hydrogen and lower alkyl;

wherein any one of said aryl, heteroaryl, heterocycle, cycloalkyl, cycloalkyl moiety of said cycloalkylalkyl, aryl moieties of said arylalkoxyalkyl, arylalkoxycarbonyl, arylalkyl, arylalkylcarbonyl, arylcarbonyl, aryloxyalkyl, aryloxycarbonyl, arylthioalkoxyalkyl and arylthioalkyl, heteroaryl moieties of said heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl and heteroarylthioalkyl, and heterocycle moieties of said heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, and heterocyclethioalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, $-NR_A R_B$, $(NR_A R_B)$alkoxy and $(NR_A R_B)$alkyl; and $R_A$ and $R_B$ are independently selected from the group consisting of hydrogen and lower alkyl.

7. The compound according to claim 6, wherein $R_1$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl;

$R_2$ and $R_3$ are independently selected from the group consisting of hydrogen, alkoxycarbonylalkyl, alkyl, arylalkoxyalkyl, arylalkyl, heteroarylalkyl, heterocyclealkyl and cycloalkylalkyl;

$R_4$ is heteroaryl wherein said heteroaryl is selected from the group consisting of furyl, imidazolyl, isothiazolyl, isoxazolyl, oxadiazolyl, oxazolyl, pyrazinyl, pyrazolyl, pyridinyl, pyrimidinyl, pyridazinyl, pyrrolyl, tetrazinyl, tetrazolyl, thiadiazolyl, thiazolyl, thienyl, triazinyl and triazolyl; and $R_8$ and $R_9$ are independently selected from the group consisting of hydrogen, alkyl, heteroarylalkoxycarbonyl, and heterocyclealkoxycarbonyl.

8. The compound according to claim 6, wherein $R_1$ is heteroaryl wherein said heteroaryl is selected from the group consisting of imidazolyl, oxazolyl, pyrazolyl, pyridinyl, thiazolyl, and thienyl;

$R_2$ and $R_3$ are independently selected from the group consisting of hydrogen, alkoxycarbonylalkyl, alkyl, arylalkoxyalkyl wherein the aryl portion of arylalkoxyalkyl is phenyl or naphthyl, arylalkyl wherein the aryl portion of arylalkyl is phenyl or naphthyl, and cycloalkylalkyl wherein the cycloalkyl portion of cycloalkylalkyl is cyclopropyl, cyclobutyl, cyclopentyl or cyclohexyl;

$R_4$ is heteroaryl wherein said heteroaryl is selected from the group consisting of imidazolyl, oxazolyl, pyrazolyl, pyridinyl, thiazolyl, and thienyl;

$R_8$ and $R_9$ are independently selected from the group consisting of hydrogen, alkyl, heteroarylalkoxycarbonyl, and heterocyclealkoxycarbonyl.

9. The compound according to claim 6, wherein
$R_1$ is heteroaryl wherein said heteroaryl is thiazol-5-yl;
$R_2$ is arylalkyl wherein the aryl portion of arylalkyl is phenyl or naphthyl;
$R_3$ is arylalkyl wherein the aryl portion of arylalkyl is phenyl or naphthyl;
$R_4$ is heteroaryl wherein said heteroaryl is thiazol-5-yl;
$R_5$ is hydrogen;
$R_6$ is hydrogen;
$R_9$ is alkyl; and
$R_9$ is alkyl.

10. The compound according to claim 6, wherein
$R_1$ is heteroaryl wherein said heteroaryl is thiazol-5-yl;
$R_2$ is arylalkyl wherein the aryl portion of arylalkyl is phenyl or naphthyl;
$R_3$ is arylalkyl wherein the aryl portion of arylalkyl is phenyl or naphthyl;
$R_4$ is heteroaryl wherein said heteroaryl is thiazol-5-yl;
$R_5$ is hydrogen;
$R_6$ is hydrogen; and
$R_8$ and $R_9$ are independently selected from the group consisting of hydrogen and heteroarylalkoxycarbonyl wherein the heteroaryl portion of heteroarylalkoxycarbonyl is thiazol-5-yl.

11. The compound according to claim 1, selected from the group consisting of
N,N'-diethyl-N,N'-bis[2-(thiazol-5-ylmethoxycarbonylamino)-3-phenylpropyl]ethylenediamine;
N,N'-diisopropyl-N,N'-bis[2-(thiazol-5-ylmethoxycarbonylamino)-3-phenylpropyl]ethylenediamine; and
N,N'-bis-[2-(thiazol-5-ylmethoxycarbonylamino)-3-phenylpropyl]-N-(thiazol-5-ylmethoxycarbonyl)ethylenediamine; or a pharmaceutically acceptable salt, prodrug, salt of a prodrug, or a combination thereof.

12. The compound according to claim 11 that is N,N'-bis-[2-(thiazol-5-ylmethoxycarbonylamino)-3-phenylpropyl]-N-(thiazol-5-ylmethoxycarbonyl)ethylenediamine; or a pharmaceutically acceptable salt, prodrug, salt of a prodrug, or a combination thereof.

13. A method for inhibiting cytochrome P450 monooxygenase comprising contacting the cytochrome P450 monooxygenase with an amount of a compound or combination of compounds of formula I

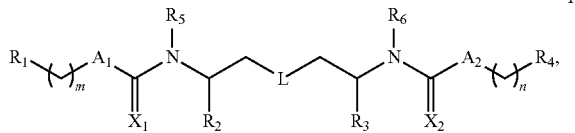

I wherein
$R_1$ is selected from the group consisting of aryl, heteroaryl and heterocycle;
$R_2$ and $R_3$ are each independently selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkenyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_CR_D)$alkyl;
$R_4$ is selected from the group consisting of aryl, heteroaryl, and heterocycle;
$R_5$ and $R_6$ are each independently selected from the group consisting of hydrogen, lower alkyl and arylalkyl;
m is 0-3;
n is 0-3;
$A_1$ is absent or selected from the group consisting of O and $NR_{A1}$ wherein $R_{A1}$ is selected from the group consisting of hydrogen and lower alkyl;
$A_2$ is absent or selected from the group consisting of O and $NR_{A2}$ wherein $R_{A2}$ is selected from the group consisting of hydrogen and lower alkyl;
$X_1$ and $X_2$ are each independently selected from the group consisting of O and S;
L is selected from the group consisting of

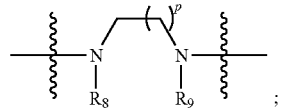

;

p is 1-5;
$R_8$ and $R_9$ are each independently selected from the group consisting of hydrogen, alkenyl, alkenylcarbonyl, alkoxyalkyl, alkoxycarbonyl, alkoxycarbonylalkyl, alkyl, alkylcarbonyl, alkylcarbonylalkyl, alkylcarbonyloxyalkyl, alkenyl, alkenylcarbonyl, arylalkoxyalkyl, arylalkyl, arylalkylcarbonyl, arylcarbonyl, aryloxyalkyl, arylthioalkoxyalkyl, arylthioalkyl, carboxyalkyl, cyanoalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocyclethioalkoxyalkyl, heterocyclethioalkyl, hydroxyalkyl, $(NR_CR_D)$alkyl and

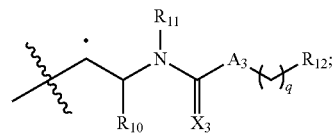

;

$R_{10}$ is selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkenyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and (NR$_A$R$_B$)alkyl;

R$_{11}$ is selected from the group consisting of hydrogen, lower alkyl and arylalkyl;

R$_{12}$ is selected from the group consisting of aryl, heteroaryl and heterocycle;

q is 0-3;

X$_3$ is selected from the group consisting of O and S; and

A$_3$ is absent or selected from the group consisting of O and NR$^{43}$ wherein R$_A$3 is selected from the group consisting of hydrogen and lower alkyl;

R$_C$ and R$_D$ are each independently selected from the group consisting of hydrogen, alkoxycarbonyl, alkyl, alkylcarbonyl, alkylsulfonyl, arylalkoxycarbonyl, arylsulfonyl, formyl, (NR$_E$R$_F$)carbonyl and (NR$_E$R$_F$)sulfonyl;

R$_E$ and R$_F$ are each independently selected from the group consisting of hydrogen and lower alkyl; and wherein any one of said aryl, heteroaryl, heterocycle, cycloalkyl, cycloalkyl moiety of said cycloalkylalkyl, aryl moieties of said arylalkoxyalkyl, arylalkoxycarbonyl, arylalkyl, arylalkylcarbonyl, arylcarbonyl, aryloxyalkyl, aryloxycarbonyl, arylthioalkoxyalkyl and arylthioalkyl, heteroaryl moieties of said heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl and heteroarylthioalkyl, and heterocycle moieties of said heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, and heterocyclethioalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkynyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —NR$_A$R$_B$, (NR$_A$R$_B$)alkoxy and (NR$_A$R$_B$)alkyl; and R$_A$ and R$_B$ independently selected from the group consisting of hydrogen and lower alkyl;

or a pharmaceutically acceptable salt, prodrug, salt of a prodrug, or combination thereof effective to inhibit cytochrome P450 monooxygenase.

14. The method of claim 13, wherein contacting the cytochrome P450 monooxygenase with an amount of the compound or combination of compounds of formula I or a pharmaceutically acceptable salt, prodrug, salt of a prodrug, or combination thereof effective to inhibit cytochrome P450 monooxygenase includes administering the compound or combination of compounds of formula I or a pharmaceutically acceptable salt, prodrug, salt of a prodrug, or combination thereof effective to inhibit cytochrome P450 monooxygenase to a human in need thereof.

15. The method of claim 13, wherein the compound of formula I is selected from the group consisting of N,N'-diethyl-N,N'-bis[2-(thiazol-5-ylmethoxycarbonylamino)-3-phenylpropyl]ethylenediamine;

N,N'-diisopropyl-N,N'-bis[2-(thiazol-5-ylmethoxycarbonylamino)-3-phenylpropyl]ethylenediamine; and N,N'-bis-[2-(thiazol-5-ylmethoxycarbonylamino)-3-phenylpropyl]-N-(thiazol-5-ylmethoxycarbonyl)ethylenediamine; or a pharmaceutically acceptable salt, prodrug, salt of a prodrug, or a combination thereof.

16. The method of claim 13, wherein the method further comprises co-administering a combination of a therapeutically effective amount of a drug which is metabolized by cytochrome P450 monooxygenase or a pharmaceutically acceptable salt thereof, and an amount of the compound or combination of compounds of formula I or a pharmaceutically acceptable salt, prodrug, salt of a prodrug, or combination thereof effective to inhibit cytochrome P450 monooxygenase.

17. A method for increasing human blood levels of a drug which is metabolized by cytochrome P450 monooxygenase comprising co-administering to a human in need of such treatment a combination of a therapeutically effective amount of said drug or a pharmaceutically acceptable salt thereof, and an amount of a compound or combination of compounds of formula I

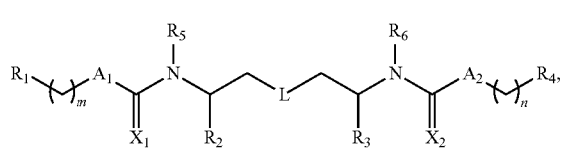

wherein

R$_1$ is selected from the group consisting of aryl, heteroaryl and heterocycle;

R$_2$ and R$_3$ are each independently selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and (NR$_C$R$_D$)alkyl;

R$_4$ is selected from the group consisting of aryl, heteroaryl, and heterocycle;

R$_5$ and R$_6$ are each independently selected from the group consisting of hydrogen, lower alkyl and arylalkyl;

m is 0-3;

n is 0-3;

A$_1$ is absent or selected from the group consisting of O and NR$_{A1}$ wherein R$_{A1}$ is selected from the group consisting of hydrogen and lower alkyl;

A$_2$ is absent or selected consisting of O and NR$_{A2}$ wherein R$_{A2}$ is selected from the group consisting of hydrogen and lower alkyl;

X$_1$ and X$_2$ are each independently selected from the group consisting of O and S;

L is selected from the group consisting of

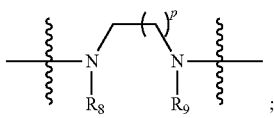

p is 1-5;
$R_8$ and $R_9$ are each independently selected from the group consisting of hydrogen, alkenyl, alkenylcarbonyl, alkoxyalkyl, alkoxycarbonyl, alkoxycarbonylalkyl, alkyl, alkylcarbonyl, alkylcarbonylalkyl, alkylcarbonyloxyalkyl, alkynyl, alkynylcarbonyl, arylalkoxycarbonyl, arylalkyl, arylalkylcarbonyl, arylcarbonyl, aryloxyalkyl, arylthioalkoxyalkyl, arylthioalkyl, carboxyalkyl, cyanoalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocyeoxyalkyl, heterocyclethioalkoxyalkyl, heterocyclethioalkyl, hydroxyalkyl, $(NR_CR_D)$alkyl and

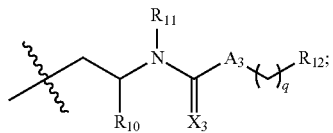

$R_{10}$ is selected from the group consisting of hydrogen, alkenyl, alkoxyalkyl, alkoxycarbonyl, alkoxycarbonylalkyl, alkyl, alkylcarbonyl, alkylcarbonylalkyl, alkylcarbonyloxyalkyl, alkynyl, arylalkoxyalkyl, arylalkoxycarbonyl, arylalkyl, arylalkylcarbonyl, arylcarbonyl, aryloxyalkyl, aryloxycarbonyl, arylthioalkoxyalkyl, arylthioalkyl, carboxyalkyl, cycloalkyl, cycloalkylalkyl, di(alkoxycarbonyl)alkyl, heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl, heteroarylthioalkyl, heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, heterocyclethioalkyl, hydroxyalkyl and $(NR_AR_B)$alkyl;
$R_{11}$ is selected from the group consisting of hydrogen, lower alkyl and arylalkyl;
$R_{12}$ is selected from the group consisting of aryl, heteroaryl and heterocycle;
q is 0-3;
$X_3$ is selected from the group consisting of O and S; and
$A_3$ is absent or selected from the group consisting of O and $NR_{A3}$ wherein $R_{A3}$ is selected from the group consisting of hydrogen and lower alkyl;

$R_C$ and $R_D$ are each independently selected from the group consisting of hydrogen, alkoxycarbonyl, alkyl, alkylcarbonyl, alkylsulfonyl, arylalkoxycarbonyl, arylsulfonyl, formyl, $(NR_ER_F)$carbonyl and $(NR_ER_F)$sulfonyl;
$R_E$ and $R_F$ are each independently selected from the group consisting of hydrogen and lower alkyl; and
wherein any one of said aryl, heteroaryl, heterocycle, cycloalkyl, cycloalkyl moiety of said cycloalkylalkyl, aryl moieties of said arylalkoxyalkyl, arylalkoxycarbonyl, arylalkyl, arylalkylcarbonyl, arylcarbonyl, aryloxyalkyl, aryloxycarbonyl, arylthioalkoxyalkyl and arylthioalkyl, heteroaryl moieties of said heteroarylalkoxyalkyl, heteroarylalkoxycarbonyl, heteroarylalkyl, heteroarylalkylcarbonyl, heteroarylcarbonyl, heteroaryloxyalkyl, heteroaryloxycarbonyl, heteroarylthioalkoxyalkyl and heteroarylthioalkyl, and heterocycle moieties of said heterocyclealkoxyalkyl, heterocyclealkoxycarbonyl, heterocyclealkyl, heterocyclealkylcarbonyl, heterocyclecarbonyl, heterocycleoxyalkyl, heterocycleoxycarbonyl, heterocyclethioalkoxyalkyl, and heterocyclethioalkyl, at each occurrence, is independently unsubstituted or substituted with 1, 2, 3, or 4 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkenyl, benzyloxy, carboxy, carboxyalkyl, cyano, cyanoalkyl, ethylenedioxy, formyl, halogen, haloalkyl, hydroxy, hydroxyalkyl, methylenedioxy, mercapto, nitro, phenoxy, thioalkoxy, thioalkoxyalkyl, —$NR_AR_B$, $(NR_AR_B)$alkoxy and $(NR_AR_B)$alkyl; and
$R_A$ and $R_B$ independently selected from the group consisting of hydrogen and lower alkyl;
or a pharmaceutically acceptable salt, prodrug, salt of a prodrug, or combination thereof effective to inhibit cytochrome P450 monooxygenase.

18. The method of claim 17, wherein the compound of formula I is selected from the group consisting of
N,N'-diethyl-N,N'-bis[2-(thiazol-5-ylmethoxycarbonylamino)-3-phenylpropyl]ethylenediamine;
N,N'-diisopropyl-N,N'-bis[2-(thiazol-5-ylmethoxycarbonylamino)-3-phenylpropyl]ethylenediamine; and
N,N'-bis-[2-(thiazol-5-ylmethoxycarbonylamino)-3-phenylpropyl]-N-(thiazol-5-ylmethoxycarbonyl)ethylenediamine; or a pharmaceutically acceptable salt, prodrug, salt of a prodrug, or a combination thereof.

19. A compound selected from the group consisting of
N,N'-diethyl-N,N'-bis[2-(thiazol-5-ylmethoxycarbonylamino)-3-phenylpropyl]ethylenediamine;
N,N'-diisopropyl-N,N'-bis[2-(thiazol-5-ylmethoxycarbonylamino)-3-phenylpropyl]ethylenediamine; and
N,N'-bis-[2-(thiazol-5-ylmethoxycarbonylamino)-3-phenylpropyl]-N-(thiazol-5-ylmethoxycarbonyl)ethylenediamine; or a pharmaceutically acceptable salt, prodrug, salt of a prodrug, or a combination thereof.

20. N,N'-bis-[2-(thiazol-5-ylmethoxycarbonylamino)-3-phenylpropyl]-N-(thiazol-5-ylmethoxycarbonyl)ethylenediamine.

* * * * *